US007321828B2

(12) United States Patent
Cowsert et al.

(10) Patent No.: US 7,321,828 B2
(45) Date of Patent: *Jan. 22, 2008

(54) SYSTEM OF COMPONENTS FOR PREPARING OLIGONUCLEOTIDES

(75) Inventors: Lex M. Cowsert, Carlsbad, CA (US); Brenda F. Baker, Carlsbad, CA (US); John McNeil, La Jolla, CA (US); Susan M. Freier, San Diego, CA (US); Henri M. Sasmor, Oceanside, CA (US); Douglas G. Brooks, San Marcos, CA (US); Cara Ohashi, San Francisco, CA (US); Jacqueline R. Wyatt, Encinitas, CA (US); Alexander H. Borchers, Encinitas, CA (US); Timothy A. Vickers, Oceanside, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/067,638

(22) Filed: Apr. 28, 1998

(65) Prior Publication Data
US 2002/0028923 A1    Mar. 7, 2002

Related U.S. Application Data

(60) Provisional application No. 60/081,483, filed on Apr. 13, 1998.

(51) Int. Cl.
C12P 19/34 (2006.01)
G06F 19/00 (2006.01)
C12Q 1/68 (2006.01)

(52) U.S. Cl. ............................. 702/19; 435/6; 435/91.1

(58) Field of Classification Search .................... 435/6, 435/69.1, 810, 283.1, 286.1, 286.2, 286.5, 435/286.7, 287.1, 257.2, 287.3, 287.7, 287.9, 435/288.3, 288.4, 288.5, 288.7, 289.1, 303.1, 435/305.1, 91.1, 7.92; 436/501; 536/25.3; 422/50, 68.1; 935/77, 78; 702/19
See application file for complete search history.

(56) References Cited

U.S. PATENT DOCUMENTS

| 3,687,808 A | 8/1972 | Merigan ..................... 195/28 |
| 4,469,863 A | 9/1984 | Ts'o et al. ..................... 536/27 |
| 4,476,301 A | 10/1984 | Imbach et al. .................. 536/27 |
| 4,587,044 A | 5/1986 | Miller et al. ................. 530/211 |
| 4,605,735 A | 8/1986 | Miyoshi et al. ............... 536/27 |
| 4,667,025 A | 5/1987 | Miyoshi et al. ............... 536/27 |
| 4,762,779 A | 8/1988 | Snitman ......................... 435/6 |
| 4,789,737 A | 12/1988 | Miyoshi et al. ............... 536/27 |
| 4,800,159 A * | 1/1989 | Mullis et al. ............. 435/172.3 |
| 4,806,463 A | 2/1989 | Goodchild et al. .............. 435/5 |
| 4,824,941 A | 4/1989 | Gordon et al. ............... 530/403 |
| 4,828,979 A | 5/1989 | Klevan et al. .................. 435/6 |
| 4,835,263 A | 5/1989 | Nguyen et al. ................ 536/27 |
| 4,845,205 A | 7/1989 | Huynh Dinh et al. ......... 536/28 |
| 4,876,335 A | 10/1989 | Yammane et al. ............. 536/27 |
| 4,904,582 A | 2/1990 | Tullis ............................. 435/6 |
| 4,948,882 A | 8/1990 | Ruth ........................... 536/27 |
| 4,958,013 A | 9/1990 | Letsinger ..................... 536/27 |
| 4,981,957 A | 1/1991 | Lebleu et al. ................. 536/27 |
| 5,013,830 A | 5/1991 | Ohtsuka et al. ............... 536/27 |
| 5,023,243 A | 6/1991 | Tullis .......................... 514/44 |
| 5,034,506 A | 7/1991 | Summerton et al. ......... 528/391 |
| 5,082,830 A | 1/1992 | Brakel et al. ................. 514/44 |
| 5,109,124 A | 4/1992 | Ramachandran et al. ..... 536/27 |
| 5,112,963 A | 5/1992 | Pieles et al. .................. 536/27 |
| 5,118,800 A | 6/1992 | Smith et al. .................. 536/23 |
| 5,118,802 A | 6/1992 | Smith et al. .................. 536/27 |
| 5,130,302 A | 7/1992 | Spielvogel et al. ........... 514/45 |
| 5,134,066 A | 7/1992 | Rogers et al. ................ 435/91 |
| 5,138,045 A | 8/1992 | Cook et al. ................... 536/27 |
| 5,149,797 A | 9/1992 | Pederson et al. .............. 536/27 |
| 5,166,315 A | 11/1992 | Summerton et al. ......... 528/406 |
| 5,175,273 A | 12/1992 | Bischofberger et al. ....... 536/27 |
| 5,177,196 A | 1/1993 | Meyer, Jr. et al. ......... 536/22.1 |

(Continued)

FOREIGN PATENT DOCUMENTS

EP    0514927    *  5/1992

(Continued)

OTHER PUBLICATIONS

Albelda et al., "Adhesion molecules and inflammatory injury", *FASEB J.*, 1994, 8, 504-512.

(Continued)

Primary Examiner—Marjorie A. Moran

(57) ABSTRACT

Interative, preferably computer based iterative processes for generating synthetic compounds with desired physical, chemical and/or bioactive properties, i.e., active compounds, are provided. During iterations of the processes, a target nucleic acid sequence is provided or selected, and a library of candidate nucleobase sequences is generated in silico according to defined criteria. A "virtual" oligonucleotide chemistry is chosen and a library of virtual oligonucleotide compounds having the selected nucleobase sequences is generated. These virtual compounds are reviewed and compounds predicted to have particular properties are selected. The selected compounds are robotically synthesized and are preferably robotically assayed for a desired physical, chemical or biological activity. Active compounds are thus generated and, at the same time, preferred sequences and regions of the target nucleic acid that are amenable to oligonucleotide or sequence-based modulation are identified.

4 Claims, 24 Drawing Sheets

U.S. PATENT DOCUMENTS

| | | | |
|---|---|---|---|
| 5,177,198 A | 1/1993 | Spielvogel et al. | 536/25.33 |
| 5,185,444 A | 2/1993 | Summerton et al. | 544/81 |
| 5,188,897 A | 2/1993 | Suhadolnik et al. | 428/402.2 |
| 5,214,134 A | 5/1993 | Weis et al. | 536/25.3 |
| 5,214,136 A | 5/1993 | Lin et al. | 514/44 |
| 5,216,141 A | 6/1993 | Benner | 536/27.13 |
| 5,218,105 A | 6/1993 | Cook et al. | 536/25.31 |
| 5,220,007 A | 6/1993 | Pederson et al. | 536/23.1 |
| 5,223,618 A | 6/1993 | Cook et al. | 544/276 |
| 5,235,033 A | 8/1993 | Summerton et al. | 528/391 |
| 5,245,022 A | 9/1993 | Weis et al. | 536/24.5 |
| 5,254,469 A | 10/1993 | Warren, III et al. | 435/188 |
| 5,256,775 A | 10/1993 | Froehler | 536/25.6 |
| 5,258,506 A | 11/1993 | Urdea et al. | 536/23.1 |
| 5,262,536 A | 11/1993 | Hobbs, Jr. | 546/25 |
| 5,264,423 A | 11/1993 | Cohen et al. | 514/44 |
| 5,264,562 A | 11/1993 | Matteucci | 536/23.1 |
| 5,264,564 A | 11/1993 | Matteucci | 536/23.1 |
| 5,272,250 A | 12/1993 | Spielvogel et al. | 530/300 |
| 5,276,019 A | 1/1994 | Cohen et al. | 514/44 |
| 5,278,302 A | 1/1994 | Caruthers et al. | 536/24.5 |
| 5,286,717 A | 2/1994 | Cohen et al. | 514/44 |
| 5,292,873 A | 3/1994 | Rokita et al. | 536/24.3 |
| 5,317,098 A | 5/1994 | Shizuya et al. | 536/23.1 |
| 5,319,080 A | 6/1994 | Leumann | 536/27.1 |
| 5,321,131 A | 6/1994 | Agrawal et al. | 536/25.34 |
| 5,352,775 A * | 10/1994 | Albertsen et al. | 536/23.1 |
| 5,359,044 A | 10/1994 | Cook et al. | 536/23.1 |
| 5,366,878 A | 11/1994 | Pederson et al. | 435/91.3 |
| 5,367,066 A | 11/1994 | Urdea et al. | 536/24.3 |
| 5,371,241 A | 12/1994 | Brush | 549/220 |
| 5,378,825 A | 1/1995 | Cook et al. | 536/25.34 |
| 5,386,023 A | 1/1995 | Sanghvi et al. | 536/25.3 |
| 5,391,723 A | 2/1995 | Priest | 536/23.1 |
| 5,393,878 A | 2/1995 | Leumann | 536/28.2 |
| 5,399,676 A | 3/1995 | Froehler | 536/23.1 |
| 5,403,711 A | 4/1995 | Walder et al. | 435/6 |
| 5,405,938 A | 4/1995 | Summerton et al. | 528/406 |
| 5,405,939 A | 4/1995 | Suhadolnik et al. | 530/322 |
| 5,407,796 A * | 4/1995 | Cutting et al. | 435/6 |
| 5,414,077 A | 5/1995 | Lin et al. | 536/24.3 |
| 5,416,203 A | 5/1995 | Letsinger | 536/25.34 |
| 5,432,272 A | 7/1995 | Benner | 536/25.3 |
| 5,434,257 A | 7/1995 | Matteucci et al. | 536/24.3 |
| 5,436,327 A | 7/1995 | Southern et al. | 536/25.34 |
| 5,446,137 A | 8/1995 | Maag et al. | 536/23.1 |
| 5,451,463 A | 9/1995 | Nelson et al. | 428/402 |
| 5,453,496 A | 9/1995 | Caruthers et al. | 536/24.5 |
| 5,455,233 A | 10/1995 | Spielvogel et al. | 514/44 |
| 5,457,187 A | 10/1995 | Gmeiner et al. | 536/25.5 |
| 5,459,255 A | 10/1995 | Cook et al. | 536/27.13 |
| 5,463,564 A | 10/1995 | Agrafiotis et al. | 364/496 |
| 5,463,657 A | 10/1995 | Rice | 375/200 |
| 5,466,677 A | 11/1995 | Baxter et al. | 514/44 |
| 5,466,786 A | 11/1995 | Buhr et al. | 536/26.26 |
| 5,470,967 A | 11/1995 | Huie et al. | 536/24.3 |
| 5,472,672 A | 12/1995 | Brennan | 422/131 |
| 5,476,925 A | 12/1995 | Letsinger et al. | 536/23.1 |
| 5,484,908 A | 1/1996 | Froehler et al. | 536/24.31 |
| 5,486,603 A | 1/1996 | Buhr | 536/24.3 |
| 5,489,677 A | 2/1996 | Sanghvi et al. | 536/22.1 |
| 5,491,133 A | 2/1996 | Walder et al. | 514/44 |
| 5,502,177 A | 3/1996 | Matteucci et al. | 536/26.6 |
| 5,507,796 A | 4/1996 | Hasson | 606/148 |
| 5,508,270 A | 4/1996 | Baxter et al. | 514/47 |
| 5,510,475 A | 4/1996 | Agrawal et al. | 536/24.3 |
| 5,512,439 A | 4/1996 | Hornes et al. | 435/6 |
| 5,512,667 A | 4/1996 | Reed et al. | 536/24.31 |
| 5,514,785 A | 5/1996 | Van Ness et al. | 536/22.1 |
| 5,519,126 A | 5/1996 | Hecht | 536/24.3 |
| 5,519,134 A | 5/1996 | Acevedo et al. | 544/243 |
| 5,523,389 A | 6/1996 | Ecker et al. | 536/23.1 |
| 5,525,465 A | 6/1996 | Haralambidis et al. | 435/6 |
| 5,525,711 A | 6/1996 | Hawkins et al. | 536/22.1 |
| 5,529,756 A | 6/1996 | Brennan | 422/131 |
| 5,536,821 A | 7/1996 | Agrawal et al. | 536/22.1 |
| 5,539,082 A | 7/1996 | Nielsen et al. | 530/300 |
| 5,541,306 A | 7/1996 | Agrawal et al. | 536/22.1 |
| 5,541,307 A | 7/1996 | Cook et al. | 536/23.1 |
| 5,541,313 A | 7/1996 | Ruth | 536/24.3 |
| 5,543,508 A | 8/1996 | Haseloff et al. | 536/23.2 |
| 5,545,730 A | 8/1996 | Urdea et al. | 536/28.51 |
| 5,550,111 A | 8/1996 | Suhadolnik et al. | 514/44 |
| 5,552,538 A | 9/1996 | Urdea et al. | 536/24.3 |
| 5,552,540 A | 9/1996 | Haralambidis | 536/25.34 |
| 5,554,613 A | 9/1996 | Mallion | 514/253 |
| 5,561,225 A | 10/1996 | Maddry et al. | 536/23.1 |
| 5,563,036 A | 10/1996 | Peterson et al. | 435/6 |
| 5,563,253 A | 10/1996 | Agrawal et al. | 536/22.1 |
| 5,565,350 A | 10/1996 | Kmiec | 435/172.3 |
| 5,565,552 A | 10/1996 | Magda et al. | 534/11 |
| 5,567,810 A | 10/1996 | Weis et al. | 536/25.3 |
| 5,567,811 A | 10/1996 | Misiura et al. | 536/25.34 |
| 5,571,639 A * | 11/1996 | Hubbell et al. | 430/5 |
| 5,571,799 A | 11/1996 | Tkachuk et al. | 514/47 |
| 5,574,142 A | 11/1996 | Meyer, Jr. et al. | 536/23.1 |
| 5,574,656 A | 11/1996 | Agrafiotis et al. | 364/500 |
| 5,576,427 A | 11/1996 | Cook et al. | 536/23.1 |
| 5,578,717 A | 11/1996 | Urdea et al. | 536/26.1 |
| 5,578,718 A | 11/1996 | Cook et al. | 536/27.21 |
| 5,580,731 A | 12/1996 | Chang et al. | 435/6 |
| 5,585,481 A | 12/1996 | Arnold, Jr. et al. | 536/25.33 |
| 5,587,361 A | 12/1996 | Cook et al. | 514/44 |
| 5,587,371 A | 12/1996 | Sessler et al. | 514/185 |
| 5,587,469 A | 12/1996 | Cook et al. | 536/23.1 |
| 5,591,584 A | 1/1997 | Chang et al. | 435/6 |
| 5,591,722 A | 1/1997 | Montgomery et al. | 514/45 |
| 5,594,121 A | 1/1997 | Froehler et al. | 536/23.5 |
| 5,595,726 A | 1/1997 | Magda et al. | 424/9.61 |
| 5,596,086 A | 1/1997 | Matteucci et al. | 536/22.1 |
| 5,596,091 A | 1/1997 | Switzer | 536/24.5 |
| 5,597,696 A | 1/1997 | Linn et al. | 435/6 |
| 5,597,909 A | 1/1997 | Urdea et al. | 536/24.3 |
| 5,599,923 A | 2/1997 | Sessler et al. | 540/145 |
| 5,599,928 A | 2/1997 | Hemmi et al. | 540/474 |
| 5,602,240 A | 2/1997 | De Mesmaeker et al. | 536/23.1 |
| 5,608,046 A | 3/1997 | Cook et al. | 536/23.1 |
| 5,610,289 A | 3/1997 | Cook et al. | 536/25.34 |
| 5,610,300 A | 3/1997 | Altmann et al. | 544/244 |
| 5,612,455 A | 3/1997 | Hoey | 530/350 |
| 5,614,617 A | 3/1997 | Cook et al. | 536/23.1 |
| 5,618,704 A | 4/1997 | Sanghvi et al. | 435/91.5 |
| 5,623,065 A | 4/1997 | Cook et al. | 536/23.1 |
| 5,623,070 A | 4/1997 | Cook et al. | 536/27.6 |
| 5,625,050 A | 4/1997 | Beaton et al. | 536/24.1 |
| 5,627,053 A | 5/1997 | Usman et al. | 435/91.1 |
| 5,633,360 A | 5/1997 | Bischofberger et al. | 536/22.1 |
| 5,639,603 A | 6/1997 | Dower et al. | 435/6 |
| 5,639,873 A | 6/1997 | Barascut et al. | 536/25.3 |
| 5,646,265 A | 7/1997 | McGee | 536/25.34 |
| 5,650,122 A | 7/1997 | Harris et al. | 422/81 |
| 5,652,355 A | 7/1997 | Metelev et al. | 536/24.5 |
| 5,652,356 A | 7/1997 | Agrawal | 536/24.5 |
| 5,658,873 A | 8/1997 | Bertsch-Frank et al. | 510/375 |
| 5,663,312 A | 9/1997 | Chaturvedula | 536/22.1 |
| 5,670,633 A | 9/1997 | Cook et al. | 536/23.1 |
| 5,677,437 A | 10/1997 | Teng et al. | 536/23.1 |
| 5,677,439 A | 10/1997 | Weis et al. | 536/23.1 |
| 5,681,941 A | 10/1997 | Cook et al. | 536/23.1 |
| 5,684,711 A | 11/1997 | Agrafiotis et al. | 364/500 |
| 5,688,941 A | 11/1997 | Cook et al. | 536/25.3 |
| 5,693,463 A | 12/1997 | Edwards et al. | 435/6 |
| 5,696,248 A | 12/1997 | Peyman et al. | 536/22.1 |
| 5,697,248 A | 12/1997 | Brown | 73/290 |

| | | | |
|---|---|---|---|
| 5,700,637 A | 12/1997 | Southern | 435/6 |
| 5,700,920 A | 12/1997 | Altmann et al. | 536/221 |
| 5,700,922 A | 12/1997 | Cook | 536/23.1 |
| 5,708,158 A | 1/1998 | Hoey | 536/23.5 |
| 5,714,331 A | 2/1998 | Buchardt et al. | 435/6 |
| 5,716,780 A | 2/1998 | Edwards et al. | 435/6 |
| 5,719,262 A | 2/1998 | Buchardt et al. | 530/300 |
| 5,720,923 A | 2/1998 | Haff et al. | 422/68.1 |
| 5,783,431 A * | 7/1998 | Peterson et al. | 435/172.3 |
| 5,824,485 A | 10/1998 | Thompson et al. | 435/6 |
| 5,856,101 A * | 1/1999 | Hubbell et al. | 435/6 |
| 5,859,221 A * | 1/1999 | Cook et al. | 536/23.1 |
| 5,901,069 A | 5/1999 | Agrafiotis et al. | 364/528.03 |
| 5,955,589 A * | 9/1999 | Cook et al. | 536/23.1 |
| 6,016,348 A | 1/2000 | Blatter et al. | 380/5 |
| 6,127,191 A * | 10/2000 | Graybill et al. | 436/518 |
| 6,295,514 B1 | 9/2001 | Agrafiotis et al. | 703/12 |
| 6,421,612 B1 | 7/2002 | Agrafiotis et al. | 702/19 |
| 6,434,490 B1 | 8/2002 | Agrafiotis et al. | 702/27 |
| 6,453,246 B1 | 9/2002 | Agrafiotis et al. | 702/27 |
| 6,506,784 B1 | 1/2003 | Dhanoa et al. | 514/407 |
| 6,518,266 B1 | 2/2003 | Dhanoa et al. | 514/229.2 |
| 6,571,227 B1 | 5/2003 | Agrafiotis et al. | 706/15 |

FOREIGN PATENT DOCUMENTS

| | | |
|---|---|---|
| EP | 0 514 927 | 11/1992 |
| EP | 0514927 * | 11/1992 |
| WO | WO 86/07363 | 12/1986 |
| WO | WO 89/10977 | 11/1989 |
| WO | WO 93/04204 | 3/1993 |
| WO | WO 94/02499 | 2/1994 |
| WO | WO 94/17093 | 8/1994 |
| WO | WO 95/28640 | 10/1995 |
| WO | WO 98/03533 | 1/1998 |
| WO | WO 98/37242 | 8/1998 |

OTHER PUBLICATIONS

Albert et al., "Antisense knockouts: molecular scalpels for the dissection of signal transduction", *TiPS*, 1994, 15, 250-254.
Altschul et al., "Basic Local Alignment Search Tool", *J. Mol. Biol.*, 1990, 215, 403-410.
Altschul et al., "Gapped Blast and PSI-BLAST: a new generation of protein database search programs", *Nucl. Acids Res.*, 1997, 25(17), 3389-3402.
Ausubel et al., *Short Protocols in Molecular Biology*, 2nd Edition, Greene Publishing Associates and John Wiley & Sons, New York, 1992, pp. 4-1 to 4-29, 10-33 to 10-35, 10-57 to 10-63, 11-3 to 11-54.
Baker et al., "Cleavage of the 5' Cap Structure of mRNA by a Europium(III) Macrocyclic Complex with Pendant Alcohol Groups", *J. Am. Chem. Soc.*, 1997, 119(38), 8749-8755.
Buhlmann et al., "Therapeutic Potential for Blockade of the CD40 Ligand, gp39", *J. Clin. Immunol.*, 1996, 16(2), 83-89.
Chiang et al., "Antisense Oligonucleotides Inhibit Intercellular Adhesion Molecule 1 Expression by Two Distinct Mechanisms", *J. Biol. Chem.*, 1991, 266, 18162-18171.
Crooke et al., "Pharmacokinetic Properties of Several Novel Oligonucleotide Analogs in mice", *J. Pharmacol. Exp. Therapeutics*, 1996, 277, 923-937.
DeMesmaeker et al., "Antisense Oligonucleotides", *Acc. Chem. Res.*, 1995, 28(9), 366-374.
Englisch et al., "Chemically Modified Oligonucleotides as Probes and Inhibitors", *Angewandte Chemie, International Edition*, 1991, 30(6), 613-629.
Forster et al., "External Guide Swquences for an RNA Enzyme", *Science*, 1990, 249, 783-786.
Freier et al., "The ups and downs of nucleic acid duplex stability: structure-stability studies on chemically-modified DNA:RNA duplexes", *Nucl. Acids Res.*, 1997, 25, 4429-4443.
Glasser, "ISIS Pharmaceuticals Demonstrates Efficacy in Crohn's Disease with its Antisense Drug", *Genetic Engin. News*, 1997, 17, 1.

Gruss et al. "CD40/CD40 Ligand Interactions in Normal, Reactive and Malignant Lympho-Hematopoietic Tissues", *Leuk. Lymphoma*, 1997, 24, 393-422.
Haseloff et al., "Simple RNA enzymes with new and highly specific endoribonuclease activities", *Nature*, 1988, 334, 585-591.
Hyrup, B. et al., "Peptide Nucleic Acids (PNA): Synthesis, Properties and Potential Applications", *Bioorg. Med. Chem.*, 1996, 4(1), 5-23.
Janeway, "How the Immune System Recognizes Invaders", *Sci. Amer.*, 1993, 269, 73-79.
Kabanov et al., "A new class of antivirals: antisense olgonucleotides combined with a hydrophobic substituent effectively inhibit influenza virus reproduction and synthesis of virus-specific proteins in MDCK cells", *FEBS Letts.*, 1990, 259(2), 327-330.
Kahn, "From Genome to Preteome: Looking at a Cell's Proteins", *Science*, 1995, 270, 369-370.
Kluth et al., "Endothelial Expression of CD40 in Renal Cell Carcinoma", *Cancer Res.*, 1997, 57, 891-899.
Kroschwitz, J.I. (ed.), "Polynucleotides", *Concise Encyclopedia of Polymer Science and Engineering*, John Wiley & Sons, 1990, 858-859.
Letsinger et al., "Cholesteryl-conjugated oligonucleotides: Synthesis, properties and activity as inhibitors of replication of human immunodeficiency virus in cell culture", *Proc. Natl. Acad. Sci.*, 1989, 86, 6553-6556.
Lima et al., "Implication of RNA Structure on Antisense Oligonucleotide Hybridization Kinetics", *Biochem.*, 1993, 31, 12055-12061.
Makgoba et al., "The CD2-LFA-3 and LFA-1-ICAM pathways: relevance to T-cell recognition", *Immunol. Today*, 1989, 10(12), 417-422.
Manoharan et al., "Cholic Acid-Oligonucliotide Conjugates for Antisense Applications", *Bioorganic Med. Chem. Letts.*, 1994, 4(8), 1053-1060.
Manoharan et al., "Chemical Modifications to Improve Uptake and Bioavailability of Antisense Oligonucleotides", *Ann. N.Y. Acad. Sci.*, 1992, 660, 306-309.
Manoharan et al., "Introduction of a Lipophilic Thioether Tether in the Minor Groove of Nucleic Acids for Antisense Applications", *Bioorg. Med. Chem. Letts.*, 1993, 3(12), 2765-2770.
Manoharan et al., "Lipidic Nucleic Acids", *Tetrahedron Letts.*, 1995, 36(21), 3651-3654.
Manoharan et al., "Oligonucleotide Conjugates: Alteration of the Pharmacokinetic Properties of Antisense Agents", *Nucleosides & Nucleotides*, 1995, 14(3-5), 969-973.
Martin et al., "Ein neuer Zugang zu 2'-O-Alkytribonucleosiden und Eigenschaften deren Oligonucleotide", *Helv. Chim. Acta*, 1995, 78, 486-504 (English summary included).
Mishra et al., "Improved leishmanicidal effect of phosphorotioate antisense oligonucleotides by LDL-medicated delivery", *Biochem. Biophys. Acta*, 1995, 1264, 229-237.
Miura et al., "Fluorometric determination of total mRNA with oligo(dT) immobized on microtiter plates", *Clin. Chem.*, 1996, 42(11), 1758-1764.
Nielsen et al., "Sequence-Selective Recognition of DNA by Strand Displacement with a Thymine-Substituted Polyamide", *Science*, 1991, 254, 1497-1500.
Nowak, "Entering the Postgenome Era", *Science*, 1995, 270, 368-371.
Oberhauser et al., "Effective incorporation of 2'-O-methyl-oligonucleotides into liposomes and enhanced cell association through modification with thiocholesterol", *Nucl. Acids Res.*, 1992, 20(3), 533-538.
Saison-Behmoaras et al., "Short modified antisense oligonucleotides directed against Ha-*ras* point mutation induce selective cleavage of the mRNA and inhibit T24 cells proliferation", *EMBO J.*, 1991, 10(5), 1111-1118.
Sanghvi, Y.S. et al., "Heterocyclic Base Modifications in Nucleic acids and their Applications in Antisense Oligonucleotides", *Antisense Research and Applications*, CRC Press, Boca Raton, Chapter 15, 1993, 273-288.
SantaLucia et al., "Improved Nearest-Neighbor Parameters for Predicting DNA Duplex Stability", *Biochem.*, 1996, 35, 3555-3562.

Shea et al., "Synthesis, hybridization properties and antiviral activity of lipid-oligodeoxynucletide conjugates", *Nucl. Acids Res.*, 1990, 18(13), 3777-3783.

Serra et al., "Predicting Thermodynamic Properties of RNA", *Meth. Enzymol.*, 1995, 259, 242-261.

Sugimoto et al., "Thermodynamic Parameters to Predict Stability of RNA/DNA Hybrid Duplexes", *Biochem.*, 1995, 34, 11211-11216.

Svinarchuk et al., "Inhibition of HIV proliferation in MT-4 cells by antisense oligonucleotide conjugated to lipophilic groups", *Biochimie*, 1993, 79, 49-54.

Szoka, "Many are probed, but few are chosen", *Nature Biotech.*, 1997, 15, 509.

Ghosh, M.K. et al., "Evaluation of some properties of a phosphorodithioate oligodeoxyribonucleotide for antisense application," *Nucl. Acid Res.*, 1993, 21(24), 5761-5766.

Mirabelli, C.K. et al., "In vitro and in vivo pharmacologic activities of antisense oligonucleotides," *Anti-Cancer Drug Des.*, 1991, 6, 647-661.

Uhlmann, E. et al., "Antisense Oligonucleotides: A New Therapeutic Principle," *Chem. Reviews*, 1990, 90(4), 544-584.

Cooper, H.D., et al., Software of determine optimal oligonucleotide sequences based on hybridization simulation data, *Biotechniques*, Jun. 1996, 20(6), 1096-1097 (Abstract only).

DeCamp, D., et al., "Site-directed drug design," *Protein Engineering, Principles and Practice*, Cleland, J.L., et al. (Ed.), 1996, Chapter 17, 467-472.

Genome Analysis—A Laboratory Manual, "Analyzing DNA," 1997, vol. 1, 574-578.

Lomakin, A., et al., "A theoretical analysis of specificity of nucleic acid interactions with oligonucleotides and peptide nucleic acids (PNAs)," *J. Molecular Biology*, Feb. 13, 1998, 276(1), 1-24.

Parzel, V., et al., "Theoretical design of antisense RNA structures substantially improves annealing kinetics and efficacy in human cells," *Nat. Biotechnol*, Jan. 1998, 16(1), 24 (Abstract only).

Ghosh, M.K., et al., "Phosphorothioate-phosphodiester oligonucleotide co-polymers: assessment for antisense application," *Anti-Cancer Drug Design*, XP-002110959, 1993, 8, 15-32.

Hyndman, D., et al., "Software to determine optimal oligonucleotide sequences based on hybridization simulation data," *BioTechniques*, XP002932984, Jun. 1996, 20, 1090-1097.

Mitsuhashi, M., "Strategy for designing specific antisense oligonucleotide sequences of the human immunodeficiency virus type 1," *Antisense Res. & Dev.*, 1993, 3, 45-52.

Sczakiel, G., et al., "Computer-aided search for effective antisense RNA target sequences of the human immunodeficiency virus type 1," *Antisense Res. & Dev.*, 1993, 3, 45-52.

Stull, R.A., et al., "Predicting antisense oligonucleotide inhibitory efficacy: a computational approach using histograms and thermodynamic indices," *Nucleic Acids Res.*, 1992, 20(13), 3501-3508.

Lomakin, A., "A theoretical analysis of specificity of nucleic acid interactions with oligonucleotides and peptide nucleic acids (PNA's)," *J. Mol. Biol.*, Feb. 13, 1998, 276(1), 57-70.

Nickerson, et al., *Proceedings of the National Academy of Sciences, USA*, 1990, 87, 8923-8927.

Rao, et al., "*elk* tissue-specific *ets*-related genes on chromosomes X and 14 near translocation breakpoints," *Science*, 1989, 244, 66-70.

Sharrocks, et al., "The ETS-domain transcription factor family," *Int. J. Biochem. Cell Biol.*, 1997, 29(12), 1371-1387.

Xia, et al., "Thermodynamic parameters for an expanded nearest-neighbor model for formation of RNA duplexes with Watson-crick base pairs," *Biochem*, 1998, 37, 14719-14735.

Nielsen, P.E., Egholm, P.E. et. al., "Sequence-Selective Recognition of DNA by Strand Displacement with a Thymine-Substituted Polyamide", *Science*, 1991, 254, 1497-1500.

* cited by examiner

US 7,321,828 B2

SYSTEM OF COMPONENTS FOR PREPARING OLIGONUCLEOTIDES

CROSS-REFERENCE TO RELATED APPLICATIONS

The present application claims priority to provisional Application No. 60/081,483 filed Apr. 13, 1998.

FIELD OF THE INVENTION

The present invention relates generally to the generation of synthetic compounds having defined physical, chemical or bioactive properties. More particularly, the present invention relates to the automated generation of oligonucleotide compounds targeted to a given nucleic acid sequence via computer-based, iterative robotic synthesis of synthetic oligonucleotide compounds and robotic or robot-assisted analysis of the activities of such compounds. Information gathered from assays of such compounds is used to identify nucleic acid sequences that are tractable to a variety of nucleotide sequence-based technologies, for example, antisense drug discovery and target validation.

BACKGROUND OF THE INVENTION

1. Oligonucleotide Technology

Synthetic oligonucleotides of complementarity to targets are known to hybridize with particular, target nucleic acids. In one example, compounds complementary to the 'sense' strand of nucleic acids that encode polypeptides, are referred to as "antisense oligonucleotides." A subset of such compounds may be capable of modulating the expression of target nucleic acid in vivo; such synthetic compounds are described herein as "active oligonucleotide compounds."

Oligonucleotide compounds are also commonly used in vitro as research reagents and diagnostic aids, and in vivo as therapeutic and bioactive agents. Oligonucleotide compounds can exert their effect by a variety of means. One such means is the antisense-mediated use of an endogenous nuclease, such as RNase H in eukaryotes or RNase P in prokaryotes, to the target nucleic acid (Chiang et al., *J. Biol. Chem.*, 1991, 266, 18162; Forster et al., *Science*, 1990, 249, 783). Another means involves covalently linking of a synthetic moiety having nuclease activity to an oligonucleotide having an antisense sequence. This does not rely upon recruitment of an endogenous nuclease to modulate target activity. Synthetic moieties having nuclease activity include, but are not limited to, enzymatic RNAs, lanthanide ion complexes, and other reactions species. (Haseloff et al., Nature, 1988, 334, 585; Baker et al., *J. Am. Chem. Soc.*, 1997, 119, 8749).

Despite the advances made in utilizing antisense technology to date, it is still common to identify sequences amenable to antisense technologies through an empirical approach (Szoka, *Nature Biotechnology*, 1997, 15, 509). Accordingly, the need exists for systems and methods for efficiently and effectively identifying target nucleotide sequences that are suitable for antisense modulation. The present disclosure answers this need by providing systems and methods for automatically identifying such sequences via in silico, robotic or other automated means.

2. Identification of Active Oligonucleotide Compounds

Traditionally, new chemical entities with useful properties are generated by (1) identifying a chemical compound (called a 'lead compound') with some desirable property or activity, (2) creating variants of the lead compound, and (3) evaluating the property and activity of such variant compounds. The process has been called 'SAR', i.e., structure activity relationship. Although 'SAR' and its handmaiden, rational drug design, has been utilized with some degree of success, there are a number of limitations to these approaches to lead compound generation, particularly as it pertains to the discovery of bioactive oligonucleotide compounds. In attempting to use SAR with oligonucleotides, it has been recognized that RNA structure can inhibit duplex formation with antisense compounds, so much so that "moving" the target nucleotide sequence even a few bases can drastically decrease the activity of such compounds (Lima et al., *Biochemistry*, 1992, 31, 12055).

Heretofore, the search for lead antisense compounds has been limited to the manual synthesis and analysis of such compounds. Consequently, a fundamental limitation of the conventional approach is its dependence upon the availability, number and cost of antisense compounds produced by manual, or at best semi-automated, means. Moreover, the assaying of such compounds has traditionally been performed by tedious manual techniques. Thus, the traditional approach to generating active antisense compounds is limited by the relatively high cost and long time required to synthesize and screen a relatively small number of candidate antisense compounds.

Accordingly, the need exists for systems and methods for efficiently and effectively generating new active antisense and other olgonucleotide compounds targeted to specific nucleic acid sequences. The present disclosure answers this need by providing systems and methods for automatically generating active antisense compounds via robotic and other automated means.

3. Gene Function Analysis

Efforts such as the Human Genome Project are making an enormous amount of nucleotide sequence information available in a variety of forms, e.g., genomic sequences, cDNAs, expressed sequence tags (ESTs) and the like. This explosion of information has led one commentator to state that 'genome scientists are producing more genes than they can put a function to' (Kahn, *Science,* 1995, 270, 369). Although some approaches to this problem have been suggested, no solution has yet emerged. For example, methods of looking at gene expression in different disease states or stages of development only provide, at best, an association between a gene and a disease or stage of development (Nowak, *Science,* 1995, 270, 368). Another approach, looking at the proteins encoded by genes, is developing but 'this approach is more complex and big obstacles remain' (Kahn, *Science,* 1995, 270, 369). Furthermore, neither of these approaches allows one to directly utilize nucleotide sequence information to perform gene function analysis.

In contrast, antisense technology does allow for the direct utilization of nucleotide sequence information for gene function analysis. Once a target nucleic acid sequence has been selected, antisense sequences hybridizable to the sequence can be generated using techniques known in the art. Typically, a large number of candidate antisense oligonucleotides (ASOs) are synthesized having sequences that are more-or-less randomly spaced across the length of the target nucleic acid sequence (e.g., a 'gene walk') and their ability to modulate the expression of the target nucleic acid is assayed. Cells or animals can then be treated with one or more active antisense oligonucleotides, and the resulting effects determined in order to determine the function(s) of the target gene. Although the practicality and value of this empirical approach to developing active antisense compounds has been acknowledged in the art, it has also been stated that this approach 'is beyond the means of most laboratories and is not feasible when a new gene sequence is identified, but whose function and therapeutic potential are unknown' (Szoka, *Nature Biotechnology*, 1997, 15, 509).

Accordingly, the need exists for systems and methods for efficiently and effectively determining the function of a gene that is uncharacterized except that its nucleotide sequence, or a portion thereof, is known. The present disclosure answers this need by providing systems and methods for automatically generating active antisense compounds to a target nucleotide sequence via robotic means. Such active antisense compounds are contacted with cells, cell-free extracts, tissues or animals capable of expressing the gene of interest and subsequent biochemical or biological parameters are measured. The results are compared to those obtained from a control cell culture, cell-free extract, tissue or animal which has not been contacted with an active antisense compound in order to determine the function of the gene of interest.

4. Target Validation

Determining the nucleotide sequence of a gene is no longer an end unto itself; rather, it is 'merely a means to an end. The critical next step is to validate the gene and its [gene] product as a potential drug target' (Glasser, *Genetic Engineering News*, 1997, 17, 1). This process, i.e., confirming that modulation of a gene that is suspected of being involved in a disease or disorder actually results in an effect that is consistent with a causal relationship between the gene and the disease or disorder, is known as target validation.

Efforts such as the Human Genome Project are yielding a vast number of complete or partial nucleotide sequences, many of which might correspond to or encode targets useful for new drug discovery efforts. The challenge represented by this plethora of information is how to use such nucleotide sequences to identify and rank valid targets for drug discovery. Antisense technology provides one means by which this might be accomplished; however, the many manual, labor-intensive and costly steps involved in traditional methods of developing active antisense compounds has limited their use in target validation (Szoka, *Nature Biotechnology*, 1997, 15, 509). Nevertheless, the great target specificity that is characteristic of antisense compounds makes them ideal choices for target validation, especially when the functional roles of proteins that are highly related are being investigated (Albert et al., *Trends in Pharm. Sci.*, 1994, 15, 250).

Accordingly, the need exists for systems and methods for developing compounds efficiently and effectively that modulate a gene, wherein such compounds can be directly developed from nucleotide sequence information. Such compounds are needed to confirm that modulation of a gene that is thought to be involved in a disease or disorder will in fact cause an in vitro or in vivo effect indicative of the origin, development, spread or growth of the disease or disorder.

The present disclosure answers this need by providing systems and methods for automatically generating active oligonucleotide and other compounds, especially antisense compounds, to a target nucleotide sequence via robotic or other automated means. Such active compounds are contacted with a cell culture, cell-free extract, tissue or animal capable of expressing the gene of interest, and subsequent biochemical or biological parameters indicative of the origin, development, spread or growth of the disease or disorder are measured. These results are compared to those obtained with a control cell system, cell-free extract, tissue or animal which has not been contacted with an active antisense compound in order to determine whether or not modulation of the gene of interest will have a therapeutic benefit or not. The resulting active antisense compounds may be used as positive controls when other, non antisense-based agents directed to the same target nucleic acid, or to its gene product, are screened.

It should be noted that embodiments of the invention drawn to gene function analysis and target validation have parameters that are shared with other embodiments of the invention, but also have unique parameters. For example, antisense drug discovery naturally requires that the toxicity of the antisense compounds be manageable, whereas, for gene function analysis or target validation, overt toxicity resulting from the antisense compounds is acceptable unless it interferes with the assay being used to evaluate the effects of treatment with such compounds.

U.S. Pat. No. 5,563,036 to Peterson et al. describes systems and methods of screening for compounds that inhibit the binding of a transcription factor to a nucleic acid. In a preferred embodiment, an assay portion of the process is stated to be performed by a computer controlled robot.

U.S. Pat. No. 5,708,158 to Hoey describes systems and methods for identifying pharmacological agents stated to be useful for diagnosing or treating a disease associated with a gene the expression of which is modulated by a human nuclear factor of activated T cells. The methods are stated to be particularly suited to high-thoughput screening wherein one or more steps of the process are performed by a computer controlled robot.

U.S. Pat. Nos. 5,693,463 and 5,716,780 to Edwards et al. describe systems and methods for identifying non-oligo-nucleotide molecules that specifically bind to a DNA molecule based on their ability to compete with a DNA-binding protein that recognizes the DNA molecule.

SUMMARY OF THE INVENTION

The present invention is directed to automated systems and methods for generating active oligonucleotide compounds, i.e., those having desired physical, chemical and/or biological properties. The present invention is also directed to oligonucleotide-sensitive target sequences identified, by the systems and methods. For purposes of illustration, the present invention is described herein with respect to the production of antisense oligonucleotides; however, the present invention is not limited to this embodiment.

The present invention is directed to iterative processes for generating new chemical compounds with prescribed sets of physical, chemical and/or biological properties, and to systems for implementing these processes. During each iteration of a process as contemplated herein, a target nucleic acid sequence is provided or selected, and a library of (candidate) nucleobase sequences is generated in silico (that is in a computer manipulatible and reliable form) according to defined criteria a virtual oligonucleotide chemistry is chosen. A library of virtual oligonucleotide compounds having the desired nucleobase sequences is generated. These virtual compounds are reviewed and compounds predicted to have particular desired properties are selected. The selected compounds are synthesized, preferably in a robotic, batchwise manner; and then they are robotically assayed for a desired physical, chemical or biological activity in order to identify compounds with the desired properties. Active compounds are, thus, generated and, at the same time, preferred sequences and regions of the target nucleic acid that are amenable to modulation are identified.

In subsequent iterations of the process, second libraries of candidate nucleobase sequences are generated and/or selected to give rise to a second virtual oligonucleotide library. Through multiple iterations of the process, a library of target nucleic acid sequences that are tractable to oligonucleotide technologies are identified. Such modulation includes, but is not limited to, antisense technology, gene function analysis and target validation.

Further features and advantages of the present invention, as well as the structure and operation of various embodiments of the present invention, are described in detail below with reference to the accompanying drawings. In the drawings, like reference numbers indicate identical or functionally similar elements.

BRIEF DESCRIPTION OF THE DRAWINGS

The present invention will be described with reference to the accompanying drawings, wherein.

Figure 1:
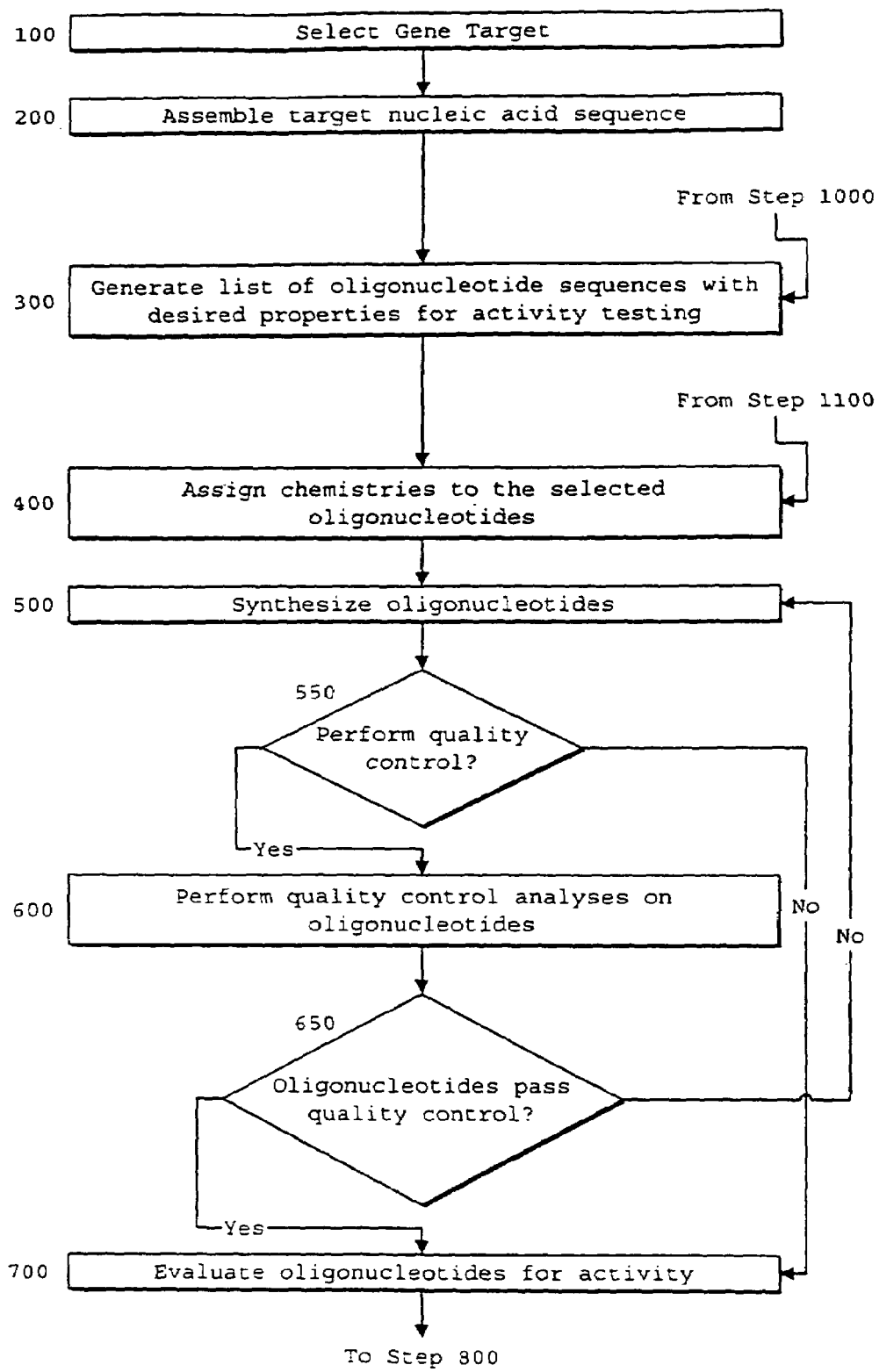
FIGS. 1 and 2 are a flow diagram of one method according to the present invention depicting the overall flow of data and materials among various elements of the invention.

Certain preferred methods of this invention are now described with reference to the flow diagram of FIGS. 1 and 2.

1. Target Nucleic Acid Selection

The target selection process, process step 100, provides a target nucleotide sequence that is used to help guide subsequent steps of the process. It is generally desired to modulate the expression of the target nucleic acid for any of a variety of purposes, such as, e.g., drug discovery, target validation and/or gene function analysis.

One of the primary objectives of the target selection process, step 100, is to identify molecular targets that represent significant therapeutic opportunities, provide new medicines to the medical community to fill therapeutic voids or improve upon existing therapies, to provide new and efficacious means of drug discovery and to determine the function of genes that are uncharacterized except for nucleotide sequence. To meet these objectives, genes are classified based upon specific sets of selection criteria.

One such set of selection criteria concerns the quantity and quality of target nucleotide sequence. There must be sufficient target nucleic acid sequence information available for oligonucleotide design. Moreover, such information must be of sufficient quality to give rise to an acceptable level of confidence in the data to perform the methods described herein. Thus, the data must not containing too many missing or incorrect base entries. In the case of a target sequence that encodes a polypeptide, such errors can be detected by virtually translating all three reading frames of the sense strand of the target sequence and confirming the presence of a continuous polypeptide sequence having predictable attributes, e.g., encoding a polypeptide of known size, or encoding a polypeptide that is about the same length as a homologous protein. In any event, only a very high frequency of sequence errors will frustrate the methods of the invention; most oligonucleotides to the target sequence will avoid such errors unless such errors occur frequently throughout the entire target sequence.

Another preferred criterion is that appropriate culturable cell lines or other source of reproducible genetic expression should be available. Such cell lines express, or can be induced to express, the gene comprising the target nucleic acid sequence. The oligonucleotide compounds generated by the process of the invention are assayed using such cell lines and, if such assaying is performed robotically, the cell line is preferably tractable to robotic manipulation such as by growth in 96 well plates. Those skilled in the art will recognize that if an appropriate cell line does not exist, it will nevertheless be possible to construct an appropriate cell line. For example, a cell line can be transfected with an expression vector comprising the target gene in order to generate an appropriate cell line for assay purposes.

For gene function analysis, it is I-ossible to operate upon a genetic system having a lack of information regarding, or incomplete characterization of, the biological function(s) of the target nucleic acid or its gene product(s). This is a powerful agent of the invention. A target nucleic acid for gene function analysis might be absolutely uncharacterized, or might be thought to have a function based on minimal data or homology to another gene. By application of the process of the invention to such a target, active compounds that modulate the expression of the gene can be developed and applied to cells. The resulting cellular, biochemical or molecular biological responses are observed, and this information is used by those skilled in the art to elucidate the function of the target gene.

For target validation and drug discovery, another selection criterion is disease association. Candidate target genes are placed into one of several broad categories of known or deduced disease association. Level 1 Targets are target nucleic acids for which there is a strong correlation with disease. This correlation can come from multiple scientific disciplines including, but not limited to, epidemiology, wherein frequencies of gene abnormalities are associated with disease incidence; molecular biology, wherein gene expression and function are associated with cellular events correlated with a disease; and biochemistry, wherein the in vitro activities of a gene product are associated with disease parameters. Because there is a strong therapeutic rationale for focusing on Level 1 Targets, these targets are most preferred for drug discovery and/or target validation.

Level 2 Targets are nucleic acid targets for which the combined epidemiological, molecular biological, and/or biochemical correlation with disease is not so clear as for Level 1. Level 3 Targets are targets for which there is little or no data to directly link the target with a disease process, but there is indirect evidence for such a link, i.e., homology with a Level 1 or Level 2 target nucleic acid sequence or with the gene product thereof. In order not to prejudice the target selection process, and to ensure that the maximum number of nucleic acids actually involved in the causation, potentiation, aggravation, spread, continuance or after-effects of disease states are investigated, it is preferred to examine a balanced mix of Level 1, 2 and 3 target nucleic acids.

In order to carry out drug discovery, experimental systems and reagents shall be available in order for one to evaluate the therapeutic potential of active compounds generated by the process of the invention. Such systems may be operable in vitro (e.g., in vitro models of cell:cell association) or in vivo (e.g., animal models of disease states). It is also desirable, but not obligatory, to have available animal model systems which can be used to evaluate drug pharmacology.

Candidate targets nucleic acids can also classified by biological processes. For example, programmed cell death ('apoptosis') has recently emerged as an important biological process that is perturbed in a wide variety of diseases. Accordingly, nucleic acids that encode factors that play a role in the apoptotic process are identified as candidate targets. Similarly, potential target nucleic acids can be classified as being involved in inflammation, autoimmune disorders, cancer, or other pathological or dysfunctional processes.

Moreover, genes can often be grouped into families based on sequence homology and biological function. Individual family members can act redundantly, or can provide specificity through diversity of interactions with downstream effectors, or through expression being restricted to specific cell types. When one member of a gene family is associated with a disease process then the rationale for targeting other members of the same family is reasonably strong. Therefore, members of such gene families are preferred target nucleic acids to which the methods and systems of the invention may be applied. Indeed, the potent specificity of antisense compounds for different gene family members makes the invention particularly suited for such targets (Albert et al., *Trends Pharm. Sci.*, 1994, 15, 250). Those skilled in the art will recognize that a partial or complete nucleotide sequence of such family members can be obtained using the polymerase chain reaction (PCR) and 'universal' primers, i.e., primers designed to be common to all members of a given gene family.

PCR products generated from universal primers can be cloned and sequenced or directly sequenced using techniques known in the art. Thus, although nucleotide sequences from cloned DNAs, or from complementary DNAs (cDNAs) derived from mRNAs, may be used in the process of the invention, there is no requirement that the target nucleotide sequence be isolated from a cloned nucleic acid. Any nucleotide sequence, no matter how determined, of any nucleic acid, isolated or prepared in any fashion, may be used as a target nucleic acid in the process of the invention.

Furthermore, although polypeptide-encoding nucleic acids provide the target nucleotide sequences in one embodiment of the invention, other nucleic acids may be targeted as well. Thus, for example, the nucleotide sequences of structural or enzymatic RNAs may be utilized for drug discovery and/or target validation when such RNAs are associated with a disease state, or for gene function analysis when their biological role is not known.

2. Assembly of Target Nucleotide Sequence.

Figure 3:
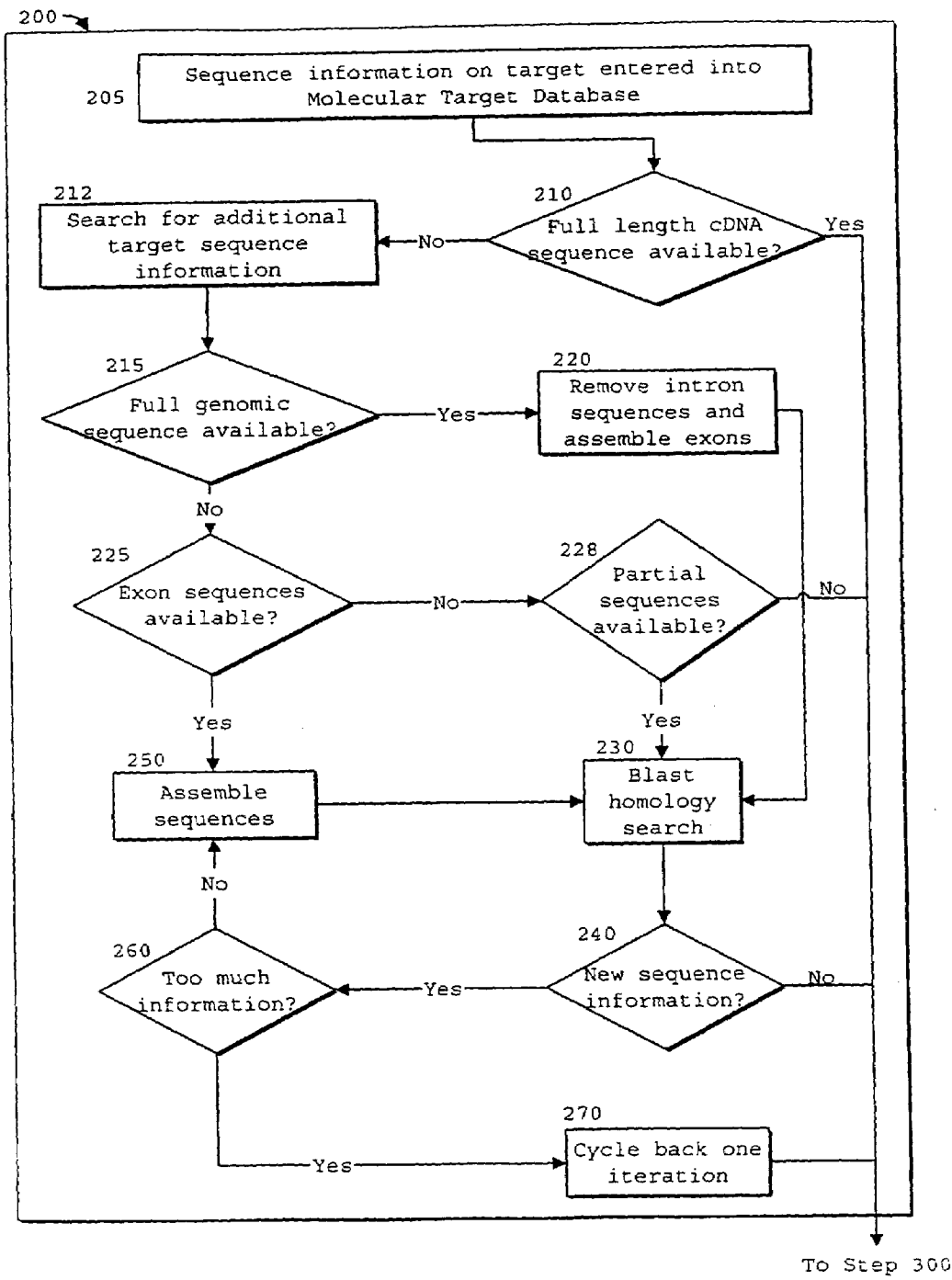
FIG. 3 is a flow diagram depicting the flow of data and materials among elements of step 200 of FIG. 1.

FIG. 3 is a block diagram detailing the steps of the target nucleotide sequence assembly process, process step 200 in accordance with one embodiment of the invention. The oligonucleotide design process, process step 300, is facilitated by the availability of accurate target sequence information. Because of limitations of automated genome sequencing technology, gene sequences are often accumulated in fragments. Further, because individual genes are often being sequenced by independent laboratories using different sequencing strategies, sequence information corresponding to different fragments is often deposited in different databases. The target nucleic acid assembly process take advantage of computerized homology search algorithms and sequence fragment assembly algorithms to search available databases for related sequence information and incorporate available sequence information into the best possible representation of the target nucleic acid molecule, for example a RNA transcript. This representation is then used to design oligonucleotides, process step 300, which can be tested for biological activity in process step 700.

In the case of genes directing the synthesis of multiple transcripts, i.e. by alternative splicing, each distinct transcript is a unique target nucleic acid for purposes of step 300. In one embodiment of the invention, if active compounds specific for a given transcript isoform are desired, the target nucleotide sequence is limited to those sequences that are unique to that transcript isoform. In another embodiment of the invention, if it is desired to modulate two or more transcript isoforms in concert, the target nucleotide sequence is limited to sequences that are shared between the two or more transcripts.

In the case of a polypeptide-encoding nucleic acid, it is generally preferred that full-length cDNA be used in the oligonucleotide design process step 300 (with full-length cDNA being defined a reading from the 5' cap to the poly A tail). Although full-length cDNA is preferred, it is possible to design oligonucleotides using partial sequence information. Therefore it is not necessary for the assembly process to generate a complete cDNA sequence. Further in some cases it may be desirable to design oligonucleotides targeting introns. In this case the process can be used to identify individual introns at process step 220.

The process can be initiated by entering initial sequence information on a selected molecular target at process step 205. In the case of a polypeptide-encoding nucleic acid, the full-length cDNA sequence is generally preferred for use in oligonucleotide design strategies at process step 300. The first step is to determine if the initial sequence information represents the full-length cDNA, decision step 210. In the case where the full-length cDNA sequence is available the process advances directly to the oligonucleotide design step 300. When the full-length cDNA sequence is not available, databases are searched at process step 212 for additional sequence information.

The algorithm preferably used in process steps 212 and 230 is BLAST (Altschul, et al., *J. Mol. Biol.*, 1990, 215, 403), or 'Gapped BLAST' (Altschul et al., *Nucl. Acids Res.*, 1997, 25, 3389). These are database search tools based on sequence homology used to identify related sequences in a sequence database. The BLAST search parameters are set to only identify closely related sequences. Some preferred databases searched by BLAST are a combination of public domain and proprietary databases. The databases, their contents, and sources are listed in Table 1.

TABLE 1

Database Sources of Target Sequences

| Database | Contents | Source |
| --- | --- | --- |
| NR | All non-redundant GenBank, EMBL, DDBJ and PDB sequences | National Center for Biotechnology Information at the National Institutes of Health |
| Month | All new or revised GenBank, EMBL, DDBJ and PDB sequences released in the last 30 days | National Center for Biotechnology Information at the National Institutes of Health |
| Dbest | Non-redundant database of GenBank, EMBL, DDBJ and EST divisions | National Center for Biotechnology Information at the National Institutes of Health |
| Dbsts | Non-redundant database of GenBank, EMBL, DDBJ and STS divisions | National Center for Biotechnology Information at the National Institutes of Health |
| Htgs | High throughput genomic sequences | National Center for Biotechnology Information at the National Institutes of Health |

When genomic sequence information is available at decision step 215, introns are removed and exons are assembled into continuous sequence representing the cDNA sequence in process step 220. Exon assembly occurs using the Phragment Assembly Program 'Phrap' (Copyright University of Washington Genome Center, Seattle, Wash.). The Phrap algorithm analyzes sets of overlapping sequences and assembles them into one continuous sequence referred to as a 'contig'. The resulting contig is preferably used to search databases for additional sequence information at process step 230. When genomic information is not available, the results of process step 212 are analyzed for individual exons at decision step 225. Exons are frequently recorded individually in databases. If multiple complete exons are identified, they are preferably assembled into a contig using Phrap at process step 250. If multiple complete exons are not identified at decision step 225, then sequences can be analyzed for partial sequence information in decision step 228. ESTs identified in the database dbEST are examples of such partial sequence information. If additional partial information is not found, then the process is advanced to process step 230 at decision step 228. If partial sequence information is found in process 212 then that information is advanced to process step 230 via decision step 228.

Process steps 230, decision steps 240, decision steps 260 and process steps 250 define a loop designed to extend iteratively the amount of sequence information available for targeting. At the end of each iteration of this loop, the results are analyzed in decision steps 240 and 260. If no new information is found then the process advances at decision steps 240 to process step 300. If there is an unexpectedly large amount of sequence information identified, then the process is preferably cycled back one iteration and that sequence is advanced at decision steps 240 to process step 300. If a small amount of new sequence information is identified, then the loop is iterated such as by taking the 100 most 5-prime (5') and 100 most 3-prime (3') bases and interating them through the BLAST homology search at process step 230. New sequence information is added to the existing contig at process step 250.

This loop is iterated until either no new sequence information is identified at decision steps 240, or an unexpectedly large amount of new information is found at decision step 260, suggesting that the process moved outside the boundary of the gene into repetitive genomic sequence. In either of these cases, iteration of this loop is preferably stopped and the process advanced to the oligonucleotide design at process step 300.

3. In Silico Generation of a Set of Nucleobase Sequences and Virtual Oligonucleotides For the following steps 300 and 400, they may be performed in the order described below, i.e., step 300 before step 400, or, in an alternative embodiment of the invention, step 400 before step 300. In this alternate embodiment, each oligonucleotide chemistry is first assigned to each oligonucleotide sequence. Then, each combination of oligonucleotide chemistry and sequence is evaluated according to the parameters of step 300. This embodiment has the desirable feature of taking into account the effect of alternative oligonucleotide chemistries on such parameters. For example, substitution of 5-methyl cytosine (5MeC or m5c) for cytosine in an antisense compound may enhance the stability of a duplex formed between that compound and its target nucleic acid. Other oligonucleotide chemistries that enhance oligonucleotide:[target nucleic acid] duplexes are known in the art (see for example, Freier et al., *Nucleic Acids Research*, 1997, 25, 4429). As will be appreciated by those skilled in the art, different oligonucleotide chemistries may be preferred for different target nucleic acids. That is, the optimal oligonucleotide chemistry for binding to a target DNA might be suboptimal for binding to a target RNA having the same nucleotide sequence.

Figure 2:
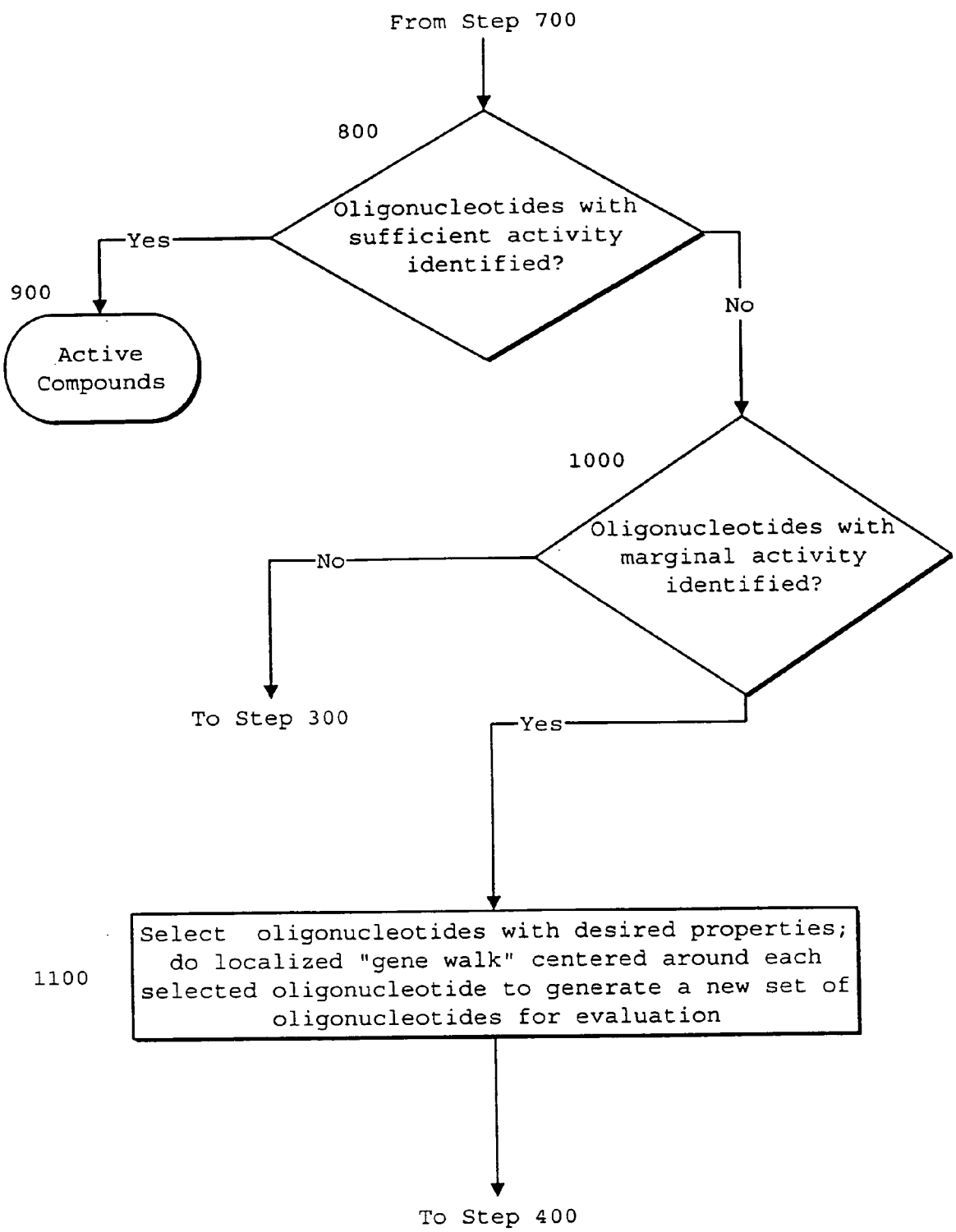
Figure 4:
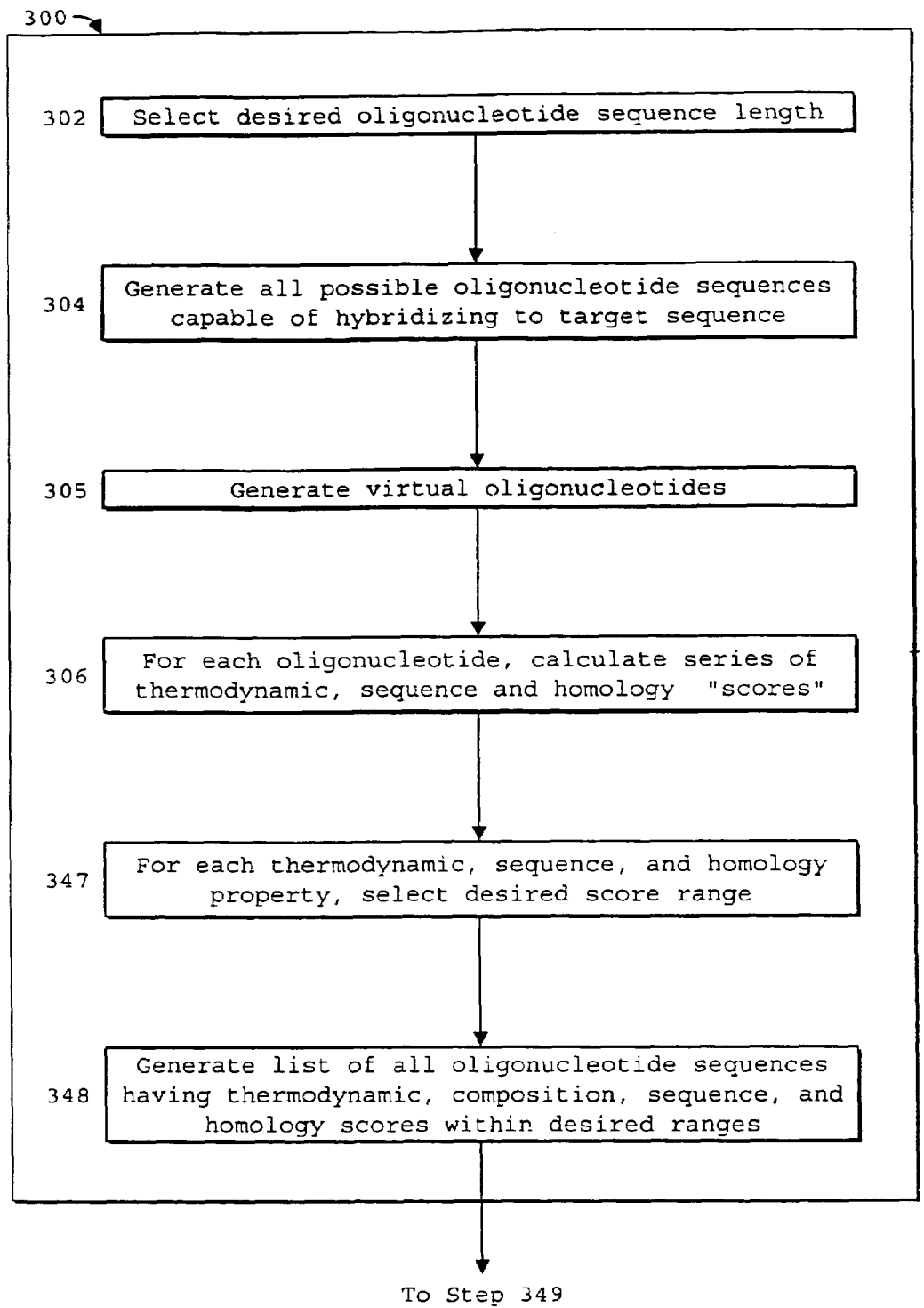
FIGS. 4 and 5 are a flow diagram depicting the flow of data and materials among elements of step 300 of FIG. 1.
Figure 5:
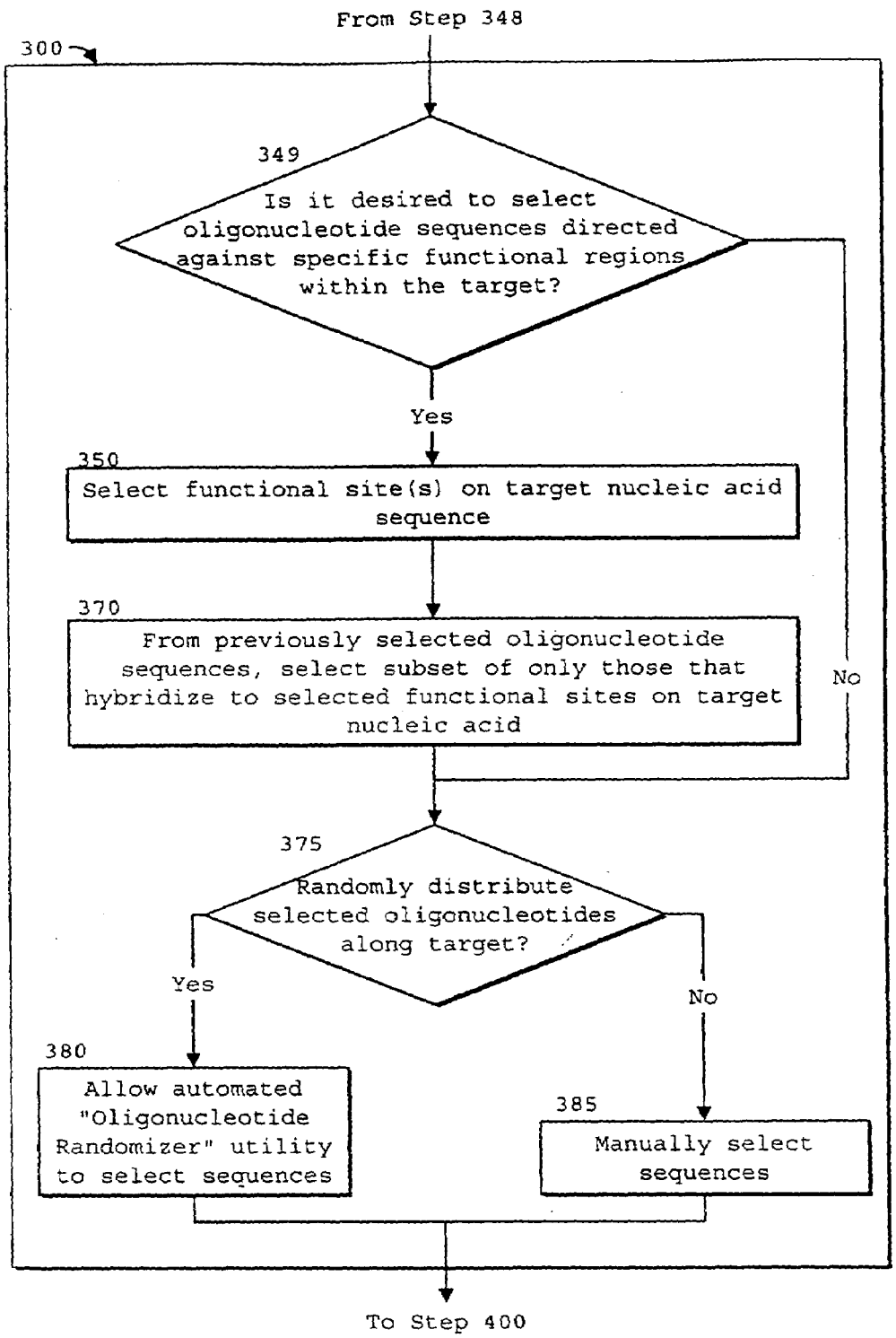

In effecting the process of the invention in the order step 300 before step 400 as seen in FIG. 1, from a target nucleic acid sequence assembled at step 200, a list of oligonucleotide sequences is generated as represented in the flowchart shown in FIGS. 4 and 5. In step 302, the desired oligonucleotide length is chosen. In a preferred embodiment, oligonucleotide length is between from about 8 to about 30, more preferably from about 12 to about 25, nucleotides. In step 304, all possible oligonucleotide sequences of the desired length capable of hybridizing to the target sequence obtained in step 200 are generated. In this step, a series of oligonucleotide sequences are generated, simply by determining the most 5' oligonucleotide possible and 'walking' the target sequence in increments of one base until the 3' most oligonucleotide possible is reached.

In step 305, a virtual oligonucleotide chemistry is applied to the nucleobase sequences of step 304 in order to yield a set of virtual oligonucleotides that can be evaluated in silico. Default virtual oligonucleotide chemistries include those that are well-characterized in terms of their physical and chemical properties, e.g., 2'-deoxyribonucleic acid having naturally occurring bases (A, T, C and G), unmodified sugar residues and a phosphodiester backbone.

Figure 6:
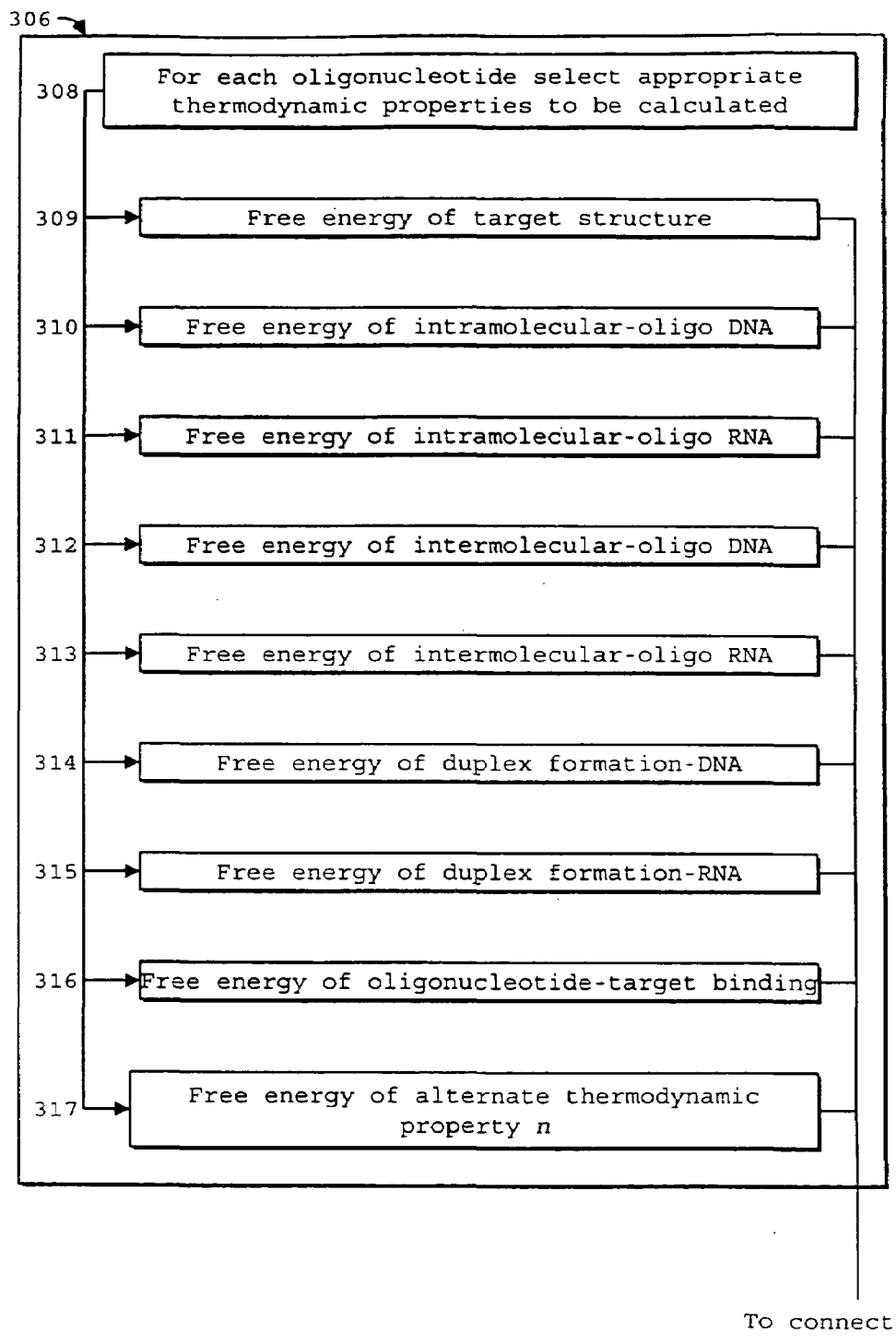
FIG. 6 is a flow diagram depicting the flow of data and materials among elements of step 306 of FIG. 4.
Figure 7:
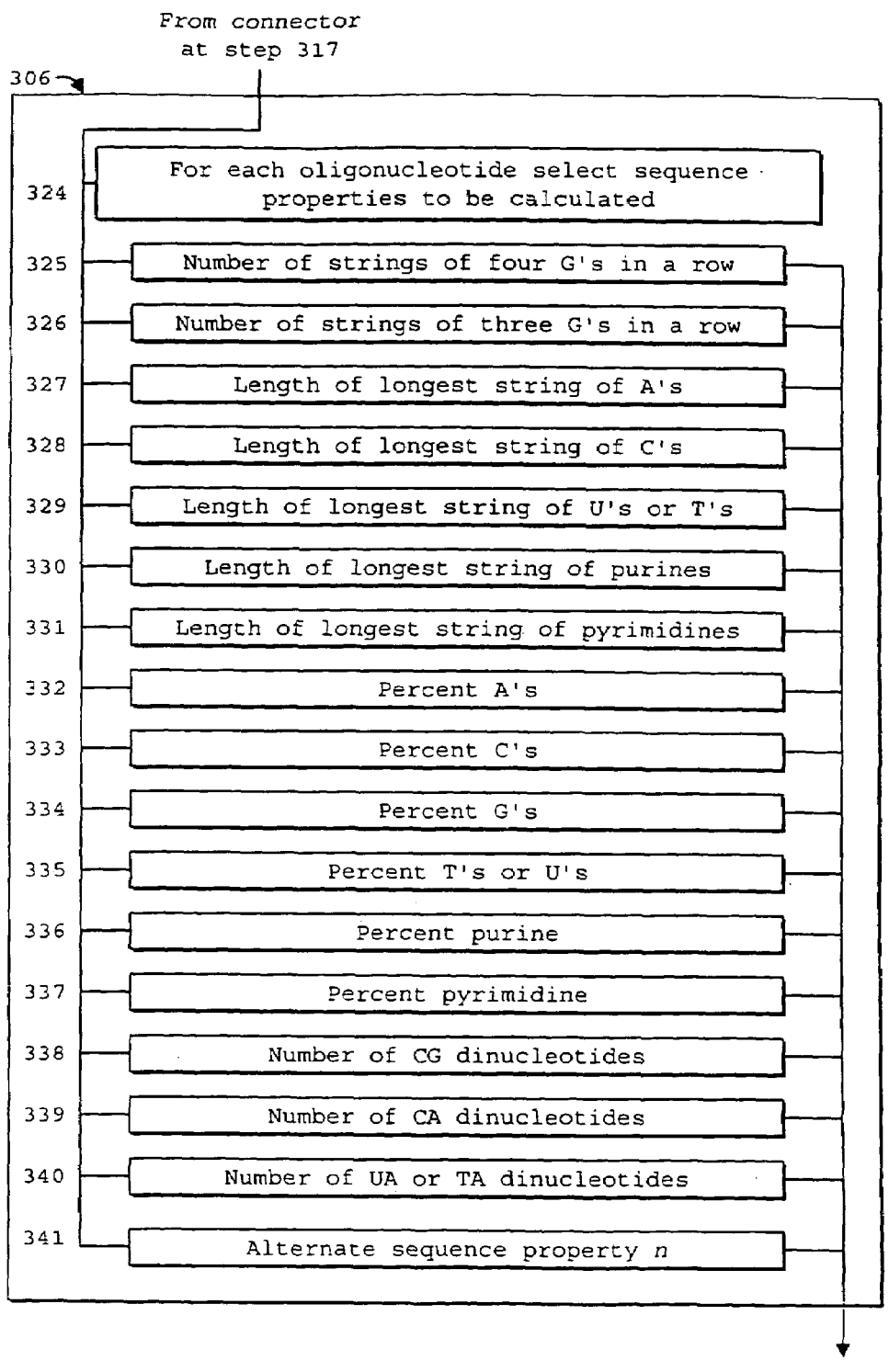
FIG. 7 is another flow diagram depicting the flow of data and materials among elements of step 306 of FIG. 4.
Figure 8:
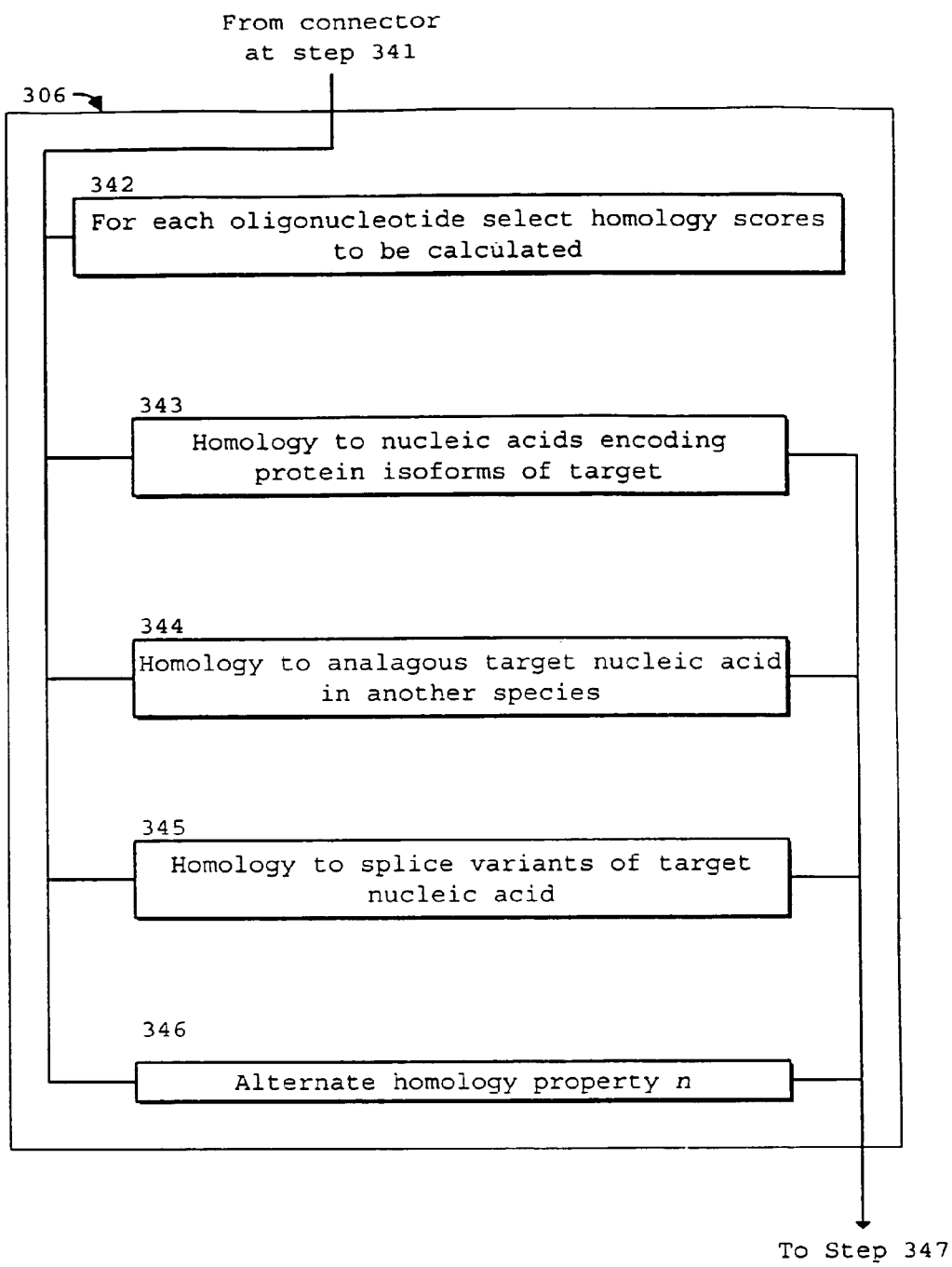
FIG. 8 is a another flow diagram depicting the flow of data and materials among elements of step 306 of FIG. 4.

4. In Silico Evaluation of Thermodynamic Properties of Virtual Oligonucleotides In step 306, a series of thermodynamic, sequence, and homology scores are preferably calculated for each virtual oligonucleotide obtained from step 305. Thermodynamic properties are calculated as represented in FIG. 6. In step 308, the desired thermodynamic properties are selected. This will typically include step 309, calculation of the free energy of the target structure. If the oligonucleotide is a DNA molecule, then steps 310, 312, and 314 are performed. If the oligonucleotide is an RNA molecule, then steps 311, 313 and 315 are performed. In both cases, these steps correspond to calculation of the free energy of intramolecular oligonucleotide interactions, intermolecular interactions and duplex formation. In addition, a free energy of oligonucleotide-target binding is preferably calculated at step 316.

Other thermodynamic and kinetic properties may be calculated for oligonucleotides as represented at step 317. Such other thermodynamic and kinetic properties may include melting temperatures, association rates, dissociation rates, or any other physical property that may be predictive of oligonucleotide activity.

The free energy of the target structure is defined as the free energy needed to disrupt any secondary structure in the target binding site of the targeted nucleic acid. This region includes any intra-target nucleotide base pairs that need to be disrupted in order for an oligonucleotide to bind to its complementary sequence. The effect of this localized disruption of secondary structure is to provide accessibility by the oligonucleotide. Such structures will include double helices, terminal unpaired and mismatched nucleotides, loops, including hairpin loops, bulge loops, internal loops and multibranch loops (Serra et al., *Methods in Enzymology*, 1995, 259, 242).

The intermolecular free energies refer to inherent energy due to the most stable structure formed by two oligonucleotides; such structures include dimer formation. Intermolecular free energies should also be taken into account when, for example, two or more oligonucleotides, of different sequence are to be administered to the same cell in an assay.

The intramolecular free energies refer to the energy needed to disrupt the most stable secondary structure within a single oligonucleotide. Such structures include, for example, hairpin loops, bulges and internal loops. The degree of intramolecular base pairing is indicative of the energy needed to disrupt such base pairing.

The free energy of duplex formation is the free energy of denatured oligonucleotide binding to its denatured target sequence. The oligonucleotide-target binding is the total binding involved, and includes the energies involved in opening up intra- and inter-molecular oligonucleotide structures, opening up target structure, and duplex formation.

The most stable RNA structure is predicted based on nearest neighbor analysis (Serra et al., *Methods in Enzymology*, 1995, 259, 242). This analysis is based on the assumption that stability of a given base pair is determined by the adjacent base pairs. For each possible nearest neighbor combination, thermodynamic properties have been determined and are provided. For double helical regions, two additional factors need to be considered, an entropy change required to initiate a helix and a entropy change associated with self-complementary strands only. Thus, the free energy of a duplex can be calculated using the equation:

$$\Delta G\degree_T = \Delta H\degree - T\Delta S\degree$$

where:
- $\Delta G$ is the free energy of duplex formation,
- $\Delta H$ is the enthalpy change for each nearest neighbor,
- $\Delta S$ is the entropy change for each nearest neighbor, and T is temperature.

The $\Delta H$ and $\Delta S$ for each possible nearest neighbor combination have been experimentally determined. These letter values are often available in published tables. For terminal unpaired and mismatched nucleotides, enthalpy and entropy measurements for each possible nucleotide combination are also available in published tables. Such results are added directly to values determined for duplex formation. For loops, while the available data is not as complete or accurate as for base pairing, one known model determines the free energy of loop formation as the sum of free energy based on loop size, the closing base pair, the interactions between the first mismatch of the loop with the closing base pair, and additional factors including being closed by AU or UA or a first mismatch of GA or UU. Such equations may also be used for oligoribonucleotide-target RNA interactions.

The stability of DNA duplexes is used in the case of intra- or intermolecular oligodeoxyribonucleotide interactions. DNA duplex stability is calculated using similar equations as RNA stability, except experimentally determined values differ between nearest neighbors in DNA and RNA and helix initiation tends to be more favorable in DNA than in RNA (SantaLucia et al., *Biochemistry*, 1996, 35, 3555).

Additional thermodynamic parameters are used in the case of RNA/DNA hybrid duplexes. This would be the case for an RNA target and oligodeoxynucleotide. Such parameters were determined by Sugimoto et al. (*Biochemistry*, 1995, 34, 11211). In addition to values for nearest neighbors, differences were seen for values for enthalpy of helix initiation.

5. In Silico Evaluation of Target Accessibility

Target accessibility is believed to be an important consideration in selecting oligonucleotides. Such a target site will possess minimal secondary structure and thus, will require minimal energy to disrupt such structure. In addition, secondary structure in oligonucleotides, whether inter- or intra-molecular, is undesirable due to the energy required to disrupt such structures. Oligonucleotide-target binding is dependent on both these factors. It is desirable to minimize the contributions of secondary structure based on these factors. The other contribution to oligonucleotide-target binding is binding affinity. Favorable binding affinities based on tighter base pairing at the target site is desirable.

Following the calculation of thermodynamic properties ending at step 317, the desired sequence properties to be scored are selected at step 324. These properties include the number of strings of four guanosine residues in a row at step 325) or three guanosines in a row at step 326), the length of the longest string of adenosines at step 327), cytidines at step 328) or uridines or thymidines at step 329), the length of the longest string of purines at step 330) or pyrimidines at step 331), the percent composition of adenosine at step 332), cytidine at step 333), guanosine at step 334) or uridines or thymidines at step 335, the percent composition of purines at step 336) or pyrimidines at step 337), the number of CG dinucleotide repeats at step 338), CA dinucleotide repeats at step 339) or UA or TA dinucleotide repeats at step 340). In addition, other sequence properties may be used as found to be relevant and predictive of antisense efficacy, as represented at step 341.

These sequence properties may be important in predicting oligonucleotide activity, or lack thereof. For example, U.S. Pat. No. 5,523,389 discloses oligonucleotides containing stretches of three or four guanosine residues in a row. Oligonucleotides having such sequences may act in a sequence-independent manner. For an antisense approach, such a mechanism is not usually desired. In addition, high numbers of dinucleotide repeats may be indicative of low complexity regions which may be present in large numbers of unrelated genes. Unequal base composition, for example, 90% adenosine, can also give non-specific effects. From a practical standpoint, it may be desirable to remove oligonucleotides that possess long stretches of other nucleotides due to synthesis considerations. Other sequences properties, either listed above or later found to be of predictive value may be used to select oligonucleotide sequences.

Following step 341, the homology scores to be calculated are selected in step 342. Homology to nucleic acids encoding protein isoforms of the target, as represented at step 343, may be desired. For example, oligonucleotides specific for an isoform of protein kinase C can be selected. Also, oligonucleotides can be selected to target multiple isoforms of such genes. Homology to analogous target sequences, as represented at step 344, may also be desired. For example, an oligonucleotide can be selected to a region common to both humans and mice to facilitate testing of the oligonucleotide in both species. Homology to splice variants of the target nucleic acid, as represented at step 345, may be desired. In addition, it may be desirable to determine homology to other sequence variants as necessary, as represented in step 346.

Following step 346, from which scores were obtained in each selected parameter, a desired range is selected to select the most promising oligonucleotides, as represented at step 347. Typically, only several parameters will be used to select oligonucleotide sequences. As structure prediction improves, additional parameters may be used. Once the desired score ranges are chosen, a list of all oligonucleotides having parameters falling within those ranges will be generated, as represented at step 348.

6. Targeting Oligonucleotides to Functional Regions of a Nucleic Acid

It may be desirable to target oligonucleotide sequences to specific functional regions of the target nucleic acid. A decision is made whether to target such regions, as represented in decision step 349. If it is desired to target functional regions then process step 350 occurs as seen in greater detail in FIG. 9. If it is not desired then the process proceeds to step 375.

Figure 9:
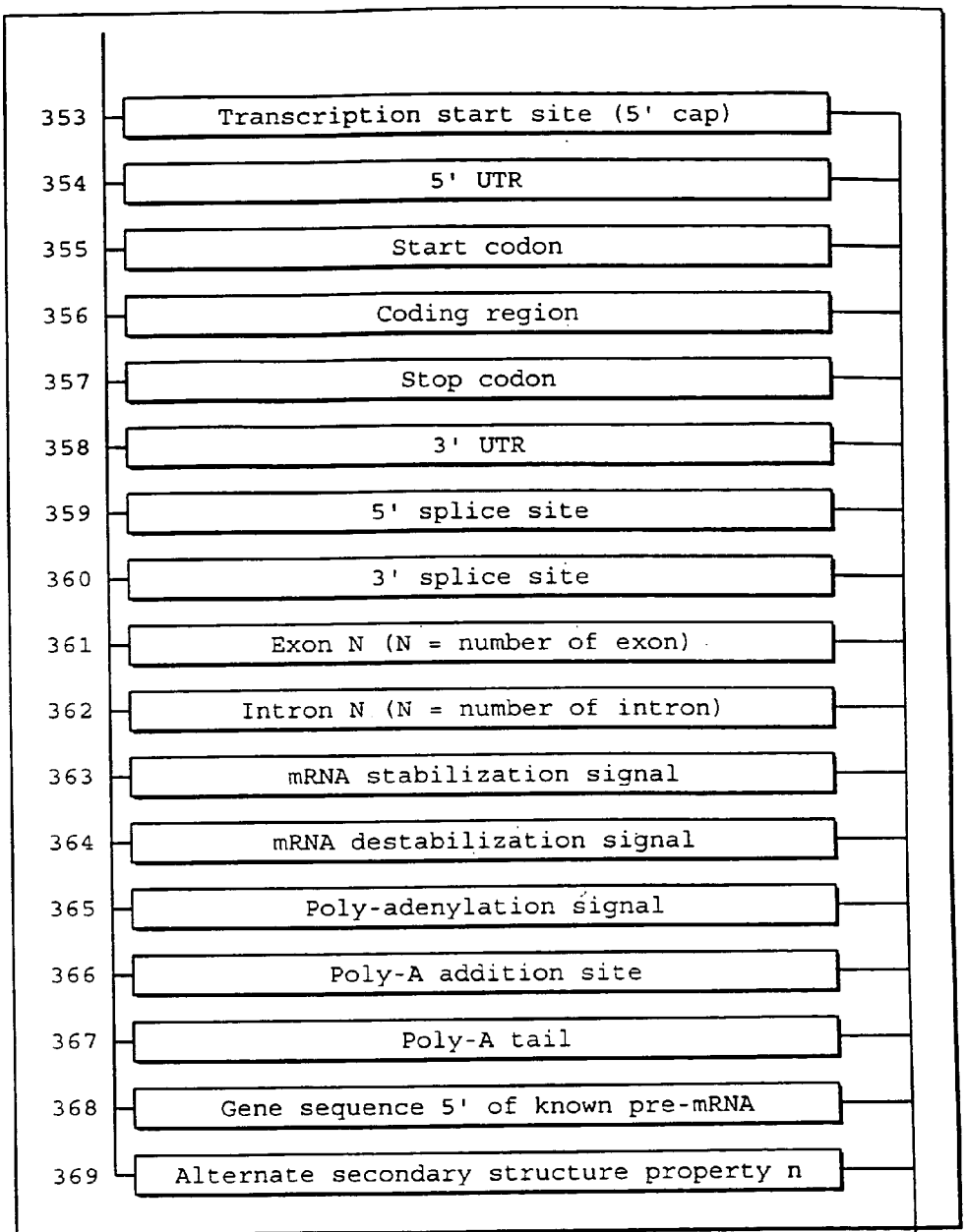
FIG. 9 is a flow diagram depicting the flow of data and materials among elements of step 350 of FIG. 5.

In step 350, as seen in FIG. 9, the desired functional regions are selected. Such regions include the transcription start site or 5' cap at step 353), the 5' untranslated region at step 354), the start codon at step 355, the coding region at step 356), the stop codon at step 357), the 3' untranslated region at step 358), 5' splice sites at step 359 or 3' splice sites at step 360, specific exons at step 361) or specific introns at step 362), mRNA stabilization signal at step 363), mRNA destabilization signal at step 364), poly-adenylation signal at step 365), poly-A addition site at step 366), poly-A tail at step 367), or the gene sequence 5' of known pre-mRNA at step 368). In addition, additional functional sites may be selected, as represented at step 369.

Many functional regions are important to the proper processing of the gene and are attractive targets for antisense approaches. For example, the AUG start codon is commonly targeted because it is necessary to initiate translation. In addition, splice sites are thought to be attractive targets because these regions are important for processing of the mRNA. Other known sites may be more accessible because of interactions with protein factors or other regulatory molecules.

After the desired functional regions are selected and determined, then a subset of all previously selected oligonucleotides are selected based on hybridization to only those desired functional regions, as represented by step 370.

7. Uniform Distribution of Oligonucleotides

Whether or not targeting functional sites is desired, a large number of oligonucleotide sequences may result from the process thus far. In order to reduce the number of oligonucleotide sequences to a manageable number, a decision is made whether to uniformly distribute selected oligonucleotides along the target, as represented in step 375. A uniform distribution of oligonucleotide sequences will aim to provide complete coverage throughout the complete target nucleic acid or the selected functional regions. A utility is used to automate the distribution of sequences, as represented in step 380. Such a utility factors in parameters such as length of the target nucleic acid, total number of oligonucleotide sequences desired, oligonucleotide sequences per unit length, number of oligonucleotide sequences per functional region. Manual selection of oligonucleotide sequences is also provided for by step 385. In some cases, it may be desirable to manually select oligonucleotide sequences. For example, it may be useful to determine the effect of small base shifts on activity. Once the desired number of oligonucleotide sequences is obtained either from step 380 or step 385, then these oligonucleotide sequences are passed onto step 400 of the process, where oligonucleotide chemistries are assigned.

8. Assignment of Actual Oligonucleotide Chemistry

Once a set of select nucleobase sequences has been generated according to the preceding process and decision steps, actual oligonucleotide chemistry is assigned to the sequences. An 'actual oligonucleotide chemistry' or simply 'chemistry' is a chemical motif that is common to a particular set of robotically synthesized oligonucleotide compounds. Preferred chemistries include, but are not limited to, oligonucleotides in which every linkage is a phosphorothioate linkage, and chimeric oligonucleotides in which a defined number of 5' and/or 3' terminal residues have a 2'-methoxyethoxy modification.

Figure 10:
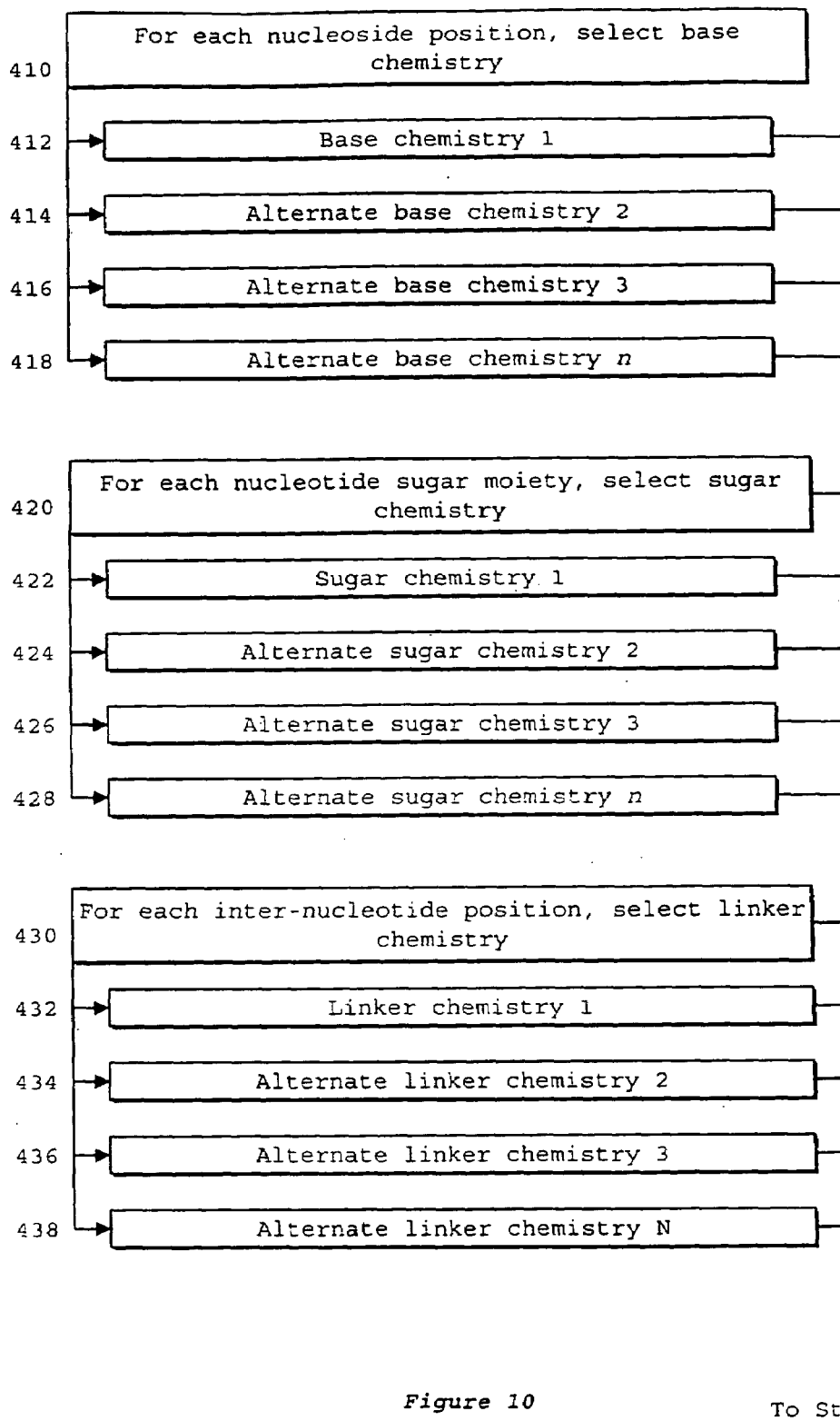
FIGS. 10 and 11 are flow diagrams depicting a logical analysis of data and materials among elements of step 400 of FIG. 1.
Figure 11:
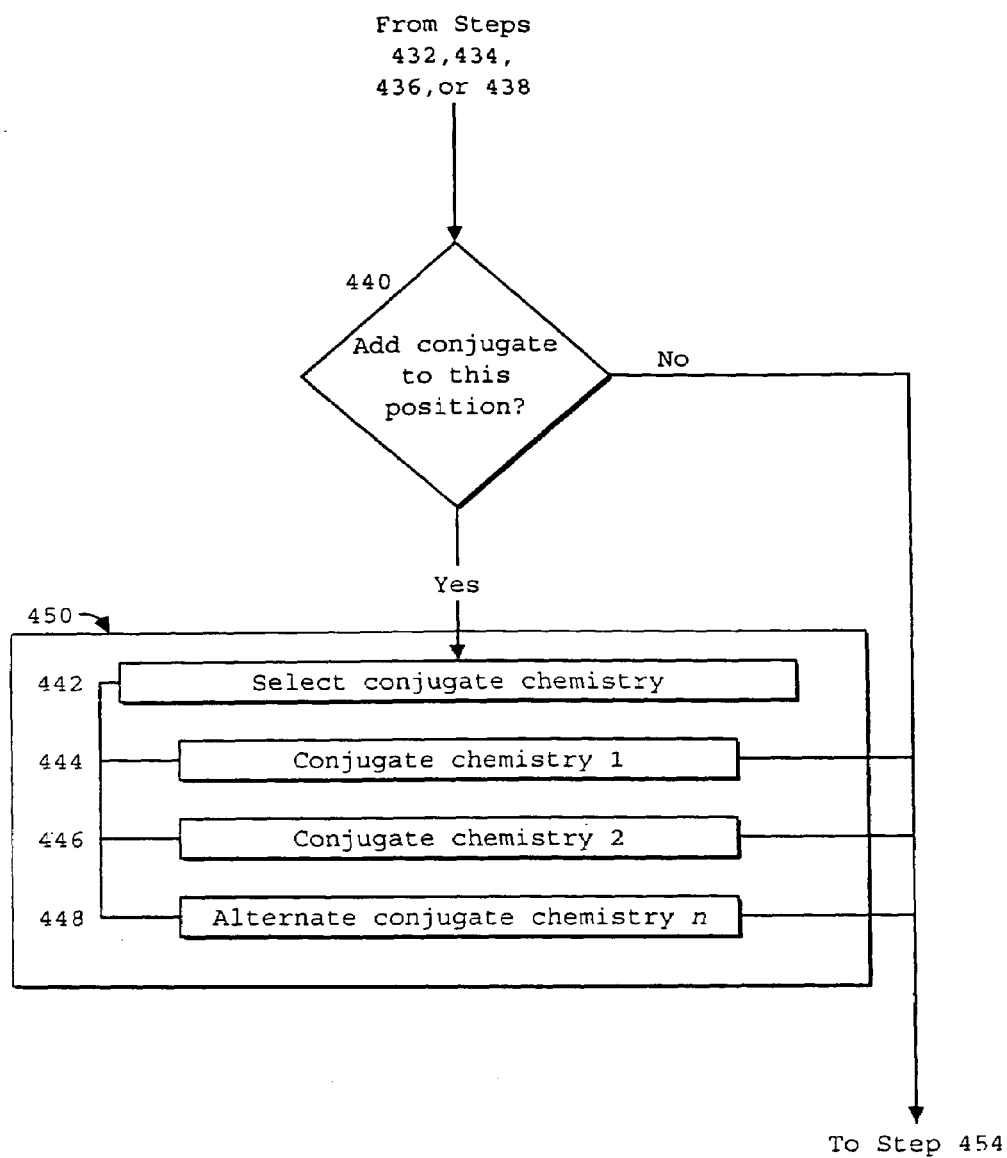
Figure 12:
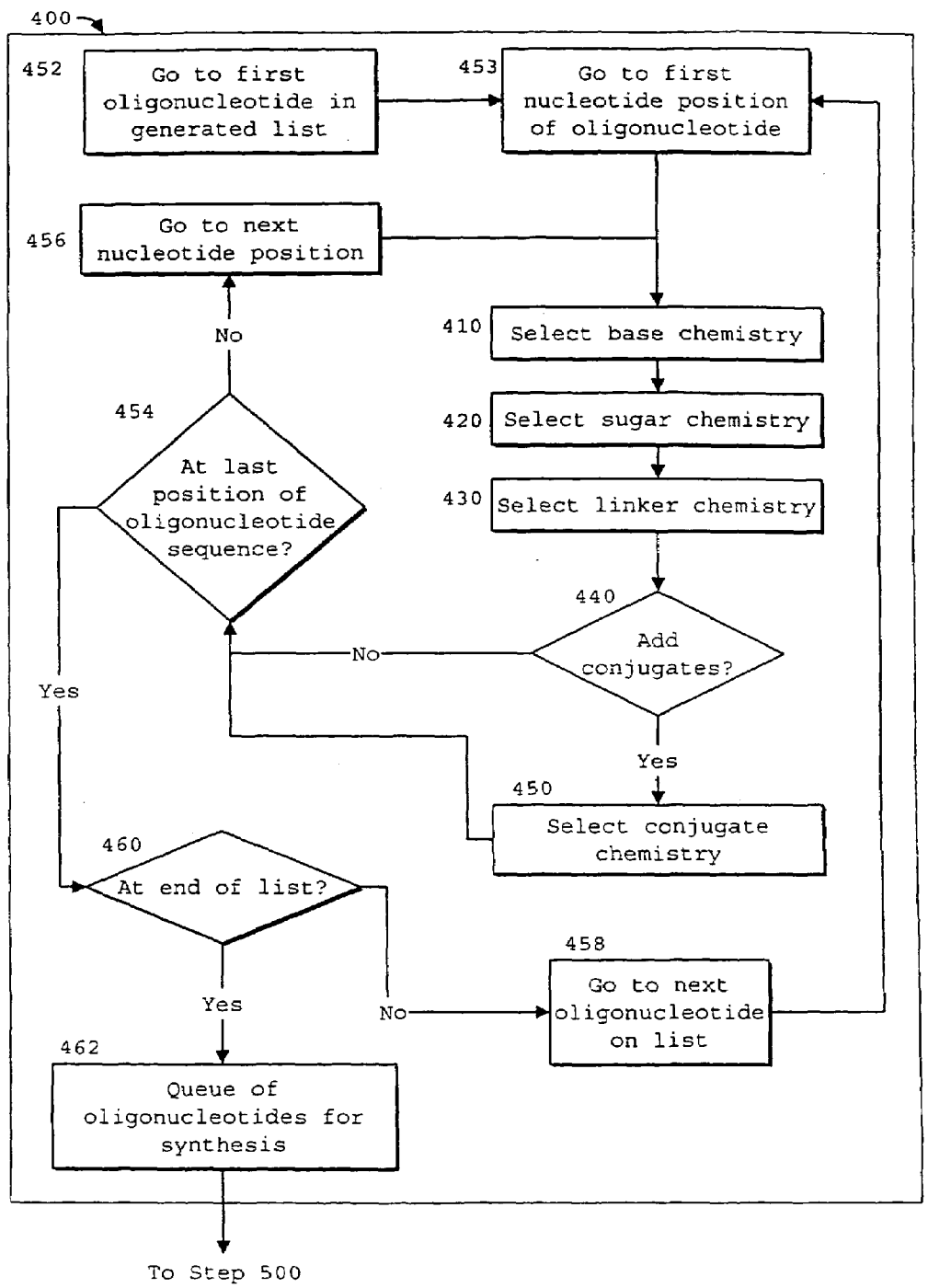
FIG. 12 is a flow diagram depicting the flow of data and materials among the elements of step 400 of FIG. 1.

Chemistries can be assigned to the nucleobase sequences during general procedure step 400 (FIG. 1). The logical basis for chemistry assignment is illustrated in FIGS. 10 and 11 and an iterative routine for stepping through an oligonucleotide nucleoside by nucleoside is illustrated in FIG. 12. Chemistry assignment can be effected by assignment directly into a word processing program, via an interactive word processing program or via automated programs and devices. In each of these instances, the output file is selected to be in a format that can serve as an input file to automated synthesis devices.

9. Oligonucleotide Compounds

In the context of this invention, in reference to oligonucleotides, the term 'oligonucleotide' is used to refer to an oligomer or polymer of ribonucleic acid (RNA) or deoxyribonucleic acid (DNA) or mimetics thereof. Thus this term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms, i.e., phosphodiester linked A, C, G, T and U nucleosides, because of desirable properties such as, for example, enhanced cellular uptake, enhanced affinity for nucleic acid target and increased stability in the presence of nucleases.

The oligonucleotide compounds in accordance with this invention can be of various lengths depending on various parameters, including but not limited to those discussed above in reference to the selection criteria of general procedure 300. For use as antisense oligonucleotides compounds of the invention preferably are from about 8 to about 30 nucleobases in length. Particularly preferred are antisense oligonucleotides comprising from about 12 to about 25 nucleobases (i.e. from about 8 to about 30 linked nucleosides). A discussion of antisense oligonucleotides and some desirable modifications can be found in De Mesmaeker et al., Acc. Chem. Res., 1995, 28, 366. Other lengths of oligonucleotides might be selected for non-antisense targeting strategies, for instance using the oligonucleotides as ribozymes. Such ribozymes normally require oligonucleotides of longer length as is known in the art.

A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a normal (where normal is defined as being found in RNA and DNA) pentofuranosyl sugar, the phosphate group can be linked to either the 2',3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred oligonucleotides useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

10. Selection of Oligonucleotide Chemistries

In a general logic scheme as illustrated in FIGS. 10 and 11, for each nucleoside position, the user or automated device is interrogated first for a base assignment, followed by a sugar assignment, a linker assignment and finally a conjugate assignment. Thus for each nucleoside, at process step 410 a base is selected. In selecting the base, base chemistry 1 can be selected at process step 412 or one or more alternative bases are selected at process steps 414, 416 and 418. After base selection is effected, the sugar portion of the nucleoside is selected. Thus for each nucleoside, at process step 420 a sugar is selected that together with the select base will complete the nucleoside. In selecting the sugar, sugar chemistry 1 can be selected at process 422 or one or more alternative sugars are selected at process steps 424, 426 and 428. For each two adjacent nucleoside units, at process step 430, the internucleoside linker is selected. The linker chemistry for the internucleoside linker can be linker chemistry 1 selected at process step 432 or one or more alternative internucleoside linker chemistries are selected at process steps 434, 436 and 438.

In addition to the base, sugar and internucleoside linkage, at each nucleoside position, one or more conjugate groups can be attached to the oligonucleotide via attachment to the nucleoside or attachment to the internucleoside linkage. The addition of a conjugate group is integrated at process step 440 and the assignment of the conjugate group is effected at process step 450.

For illustrative purposes in FIGS. 10 and 11, for each of the base, the sugar, the internucleoside linkers, or the conjugate, chemistries 1 though n are illustrated. As described in this specification, it is understood that the number of alternate chemistries between chemistry 1 and alternative chemistry n, for each of the base, the sugar, the internucleoside linkage and the conjugate, is variable and includes, but is not limited to, each of the specific alternative bases, sugar, internucleoside linkers and conjugates identified in this specification as well as equivalents known in the art.

Utilizing the logic as described in conjunction with FIGS. 10 and 11, chemistry is assigned, as is shown in FIG. 12, to the list of oligonucleotides from general procedure 300. In assigning chemistries to the oligonucleotides in this list, a pointer can be set at process step 452 to the first oligonucleotide in the list and at step 453 to the first nucleotide of that first oligonucleotide. The base chemistry is selected at step 410, as described above, the sugar chemistry is selected at step 420, also as described above, followed by selection of the internucleoside linkage at step 430, also as described above. At decision 440, the process branches depending on whether a conjugate will be added at the current nucleotide position. If a conjugate is desired, the conjugate is selected at step 450, also as described above.

Whether or not a conjugate was added at decision step 440, an inquiry is made at decision step 454. This inquiry asks if the pointer resides at the last nucleotide in the current oligonucleotide. If the result at decision step 454 is 'No', the pointer is moved to the next nucleotide in the current oligonucleotide and the loop including steps 410, 420, 430, 440 and 454 is repeated. This loop is reiterated until the result at decision step 454 is 'Yes.'

When the result at decision step 454 is 'Yes', a query is made at decision step 460 concerning the location of the pointer in the list of oligonucleotides. If the pointer is not at the last oligonucleotide of the list, the 'No' path of the decision step 460 is followed and the pointer is moved to the next oligonucleotide in the list at process step 458. With the pointer set to the next oligonucleotide in the list, the loop that starts at process steps 453 is reiterated. When the result at decision step 460 is 'Yes', chemistry has been assigned to all of the nucleotides in the list of oligonucleotides.

11. Description of Oligonucleotide Chemistries

As is illustrated in FIG. 10, for each nucleoside of an oligonucleotide, chemistry selection includes selection of the base forming the nucleoside from a large palette of different base units available. These may be 'modified' or 'natural' bases (also reference herein as nucleobases) including the natural purine bases adenine (A) and guanine (G), and the natural pyrimidine bases thymine (T), cytosine (C) and uracil (U). They further can include modified nucleobases including other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo uracils and cytosines particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering*, pages 858-859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred for selection as the base. These are particularly useful when combined with a 2'-methoxyethyl sugar modifications, described below.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, Reference is also made to allowed U.S. patent application Ser. No. 08/762,488, filed on Dec. 10, 1996, commonly owned with the present application and herein incorporated by reference.

In selecting the base for any particular nucleoside of an oligonucleotide, consideration is first given to the need of a base for a particular specificity for hybridization to an opposing strand of a particular target. Thus if an 'A' base is required, adenine might be selected however other alternative bases that can effect hybridization in a manner mimicking an 'A' base such as 2,6-diaminopurine might be selected should other considersation, e.g., stronger hybridization (relative to hybridization achieved with adenine), be desired.

As is illustrated in FIG. 10, for each nucleoside of an oligonucleotide, chemistry selection includes selection of the sugar forming the nucleoside from a large palette of different sugar or sugar surrogate units available. These may be modified sugar groups, for instance sugars containing one or more substituent groups. Preferred substituent groups comprise the following at the 2' position: OH; F; O—, S—, or N-alkyl, O—, S—, or N-alkenyl, or O, S— or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred substituent groups comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, poly-alkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486) i.e., an alkoxyalkoxy group. A further preferred modification includes 2'-dimethylamino oxyethoxy, i.e., a $O(CH_2)_2ON(CH_3)_2$ group, also known as 2'-DMAOE, as described in co-owned U.S. patent application Ser. No. 09/016,520, filed on Jan. 30, 1998, the contents of which are herein incorporated by reference.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the sugar group, particularly the 3' position of the sugar on the 3' terminal nucleotide or in 2'-5' linked oligonucleotides and the 5' position of 5' terminal nucleotide. The nucleosides of the oligonucleotides may also have sugar mimetics such as cyclobutyl moieties in place of the pentofuranosyl sugar.

Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053 5,639,873; 5,646,265; 5,658,873; 5,670,633; and 5,700,920, certain of which are commonly owned with the present application, each of which is herein incorporated by reference, together with allowed U.S. patent application Ser. No. 08/468,037, filed on Jun. 5, 1995, which is commonly owned with the present application and is herein incorporated by reference.

As is illustrated in FIG. 10, for each adjacent pair of nucleosides of an oligonucleotide, chemistry selection includes selection of the internucleoside linkage. These internucleoside linkages are also referred to as linkers, backbones or oligonucleotide backbones. For forming these nucleoside linkages, a palette of different internucleoside linkages or backbones is available. These include modified oligonucleotide backbones, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalklyphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, certain of which are commonly owned with this application, and each of which is herein incorporated by reference.

Preferred internucleoside linkages for oligonucleotides that do not include a phosphorus atom therein, i.e., for oligonucleosides, have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, certain of which are commonly owned with this application, and each of which is herein incorporated by reference.

In other preferred oligonucleotides, i.e., oligonucleotide mimetics, both the sugar and the intersugar linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-phosphate backbone of an oligonucleotide is replaced with an amide-containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497.

For the internucleoside linkages, the most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. Nos. 5,489,677, and the amide backbones of the above referenced U.S. Pat. No. 5,602,240. Also preferred are oligonucleotides having morpholino backbone structures of the above-referenced U.S. Pat. No. 5,034,506.

In attaching a conjugate group to one or more nucleosides or internucleoside linkages of an oligo-nucleotide, various properties of the oligonucleotide are modified. Thus modification of the oligonucleotides of the invention to chemically link one or more moieties or conjugates to the oligonucleotide are intended to enhance the activity, cellular distribution or cellular uptake of the oligonucleotide. Such moieties include but are not limited to lipid moieties such as a cholesterol moiety (Letsinger et al., *Proc. Natl. Acad. Sci. USA,* 1989, 86, 6553), cholic acid (Manoharan et al., *Bioorg. Med. Chem. Let.,* 1994, 4, 1053), a thioether, e.g., hexyl-S-tritylthiol (Manoharan et al., *Ann. N.Y. Acad. Sci.,* 1992, 660, 306; Manoharan et al., *Bioorg. Med. Chem. Let.,* 1993, 3, 2765), a thiocholesterol (Oberhauser et al., *Nucl. Acids Res.,* 1992, 20, 533), an aliphatic chain, e.g., dodecandiol or undecyl residues (Saison-Behmoaras et al., *EMBO J.,* 1991, 10, 111; Kabanov et al., *FEBS Lett.,* 1990, 259, 327; Svinarchuk et al., *Biochimie,* 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651; Shea et al., *Nucl. Acids Res.,* 1990, 18, 3777), a polyamine or a polyethylene glycol chain (Manoharan et al., *Nucleosides & Nucleotides,* 1995, 14, 969), or adamantane acetic acid (Manoharan et al., *Tetrahedron Lett.,* 1995, 36, 3651), a palmityl moiety (Mishra et al., *Biochim. Biophys. Acta,* 1995, 1264, 229), or an octadecylamine or hexylamino-carbonyl-oxycholesterol moiety (Crooke et al., *J. Pharmacol. Exp. Ther.,* 1996, 277, 923).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the present application, and each of which is herein incorporated by reference.

12. Chimeric Compounds

It is not necessary for all positions in a given compound to be uniformly modified. In fact, more than one of the aforementioned modifications may be incorporated in a single compound or even at a single nucleoside within an oligonucleotide. The present invention also includes compounds which are chimeric compounds. 'Chimeric' compounds or 'chimeras,' in the context of this invention, are compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids.

By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures representing the union of two or more oligonucleotides, modified oligonucleotides, oligonucleosides and/or oligonucleotide mimetics as described above. Such compounds have also been referred to in the art as "hybrids" or "gapmers". Representative United States patents that teach the preparation of such hybrid structures include, but are not limited to, U.S. Pat. Nos. 5,013,830; 5,149,797; 5,220,007; 5,256,775; 5,366, 878; 5,403,711; 5,491,133; 5,565,350; 5,623,065; 5,652, 355; 5,652,356; and 5,700,922, certain of which are commonly owned with the present application and each of which is herein incorporated by reference, together with commonly owned and allowed U.S. patent application Ser. No. 08/465, 880, filed on Jun. 6, 1995, also herein incorporated by reference.

13. Description of Automated Oligonucleotide Synthesis

In the next step of the overall process (illustrated in FIGS. 1 and 2), oligonucleotides are synthesized on an automated synthesizer. Although many devices may be employed, the synthesizer is preferably a variation of the synthesizer described in U.S. Pat. Nos. 5,472,672 and 5,529,756, the entire contents of which are herein incorporated by reference. The synthesizer described in those patents is modified to include movement in along the Y axis in addition to movement along the X axis. As so modified, a 96-well array of compounds can be synthesized by the synthesizer. The synthesizer further includes temperature control and the ability to maintain an inert atmosphere during all phases of synthesis. The reagent array delivery format employs orthogonal X-axis motion of a matrix of reaction vessels and Y-axis motion of an array of reagents. Each reagent has its own dedicated plumbing system to eliminate the possibility of cross-contamination of reagents and line flushing and/or pipette washing. This in combined with a high delivery speed obtained with a reagent mapping system allows for the extremely rapid delivery of reagents. This further allows long and complex reaction sequences to be performed in an efficient and facile manner.

The software that operates the synthesizer allows the straightforward programming of the parallel synthesis of a large number of compounds. The software utilizes a general synthetic procedure in the form of a command (.cmd) file, which calls upon certain reagents to be added to certain wells via lookup in a sequence (.seq) file. The bottle position, flow rate, and concentration of each reagent is stored in a lookup table (.tab) file. Thus, once any synthetic method has been outlined, a plate of compounds is made by permutating a set of reagents, and writing the resulting output to a text file. The text file is input directly into the synthesizer and used for the synthesis of the plate of compounds. The synthesizer is interfaced with a relational database allowing data output related to the synthesized compounds to be registered in a highly efficient manner.

Figure 13:
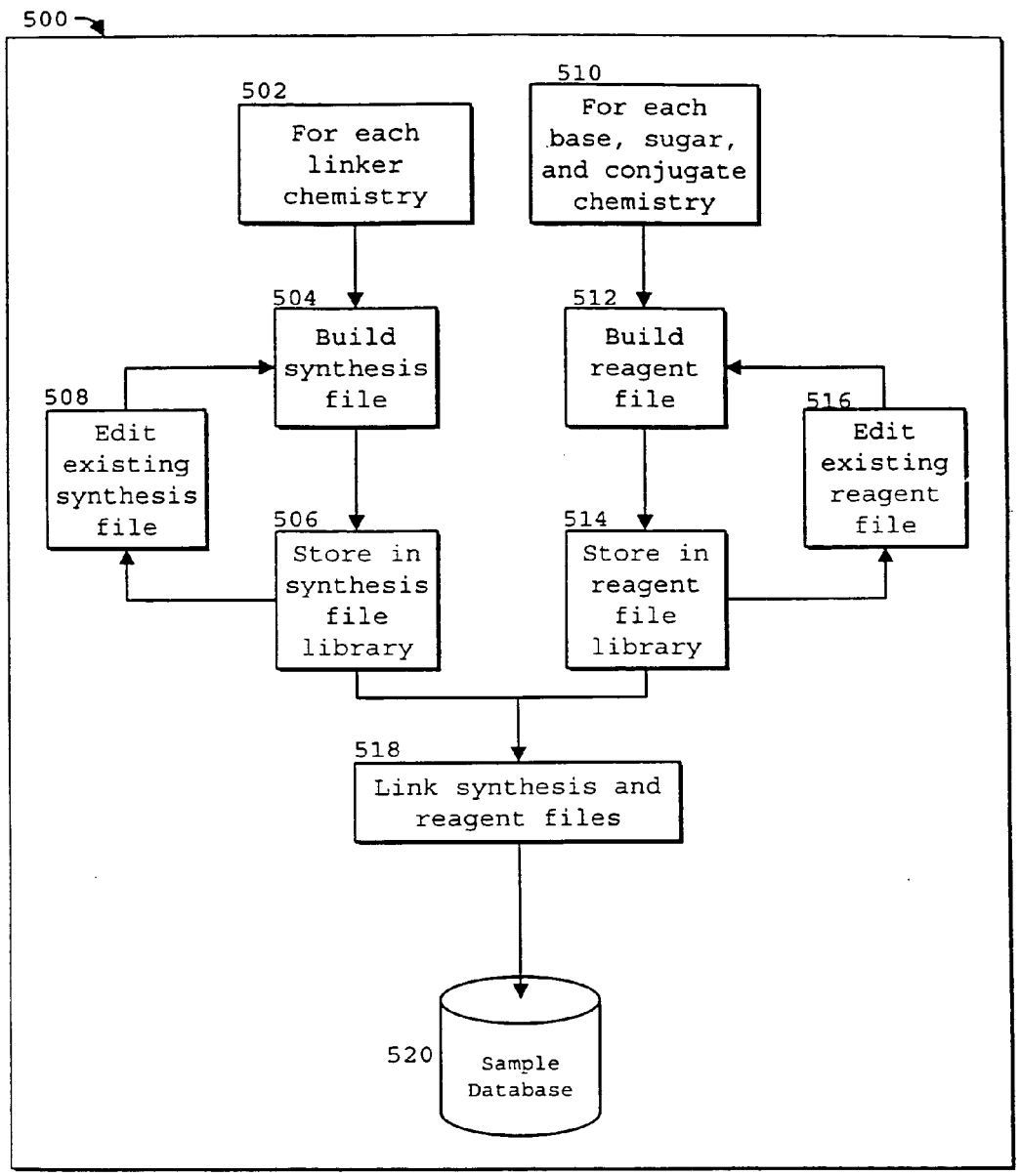
FIGS. 13 and 14 are flow diagrams depicting the flow of data and materials among elements of step 500 of FIG. 1.

Building of the .seq, .cmd and .tab files is illustrated in FIG. 13. Thus as a part of the general oligonucleotide synthesis procedure 500, for each linker chemistry at process step 502, a synthesis file, i.e., a .cmd file, is built at process step 504. This file can be built fresh to reflect a completely new set of machine commands reflecting a set of chemical synthesis steps or it can modify an existing file stored at process step 504 by editing that stored file in process step 508. The .cmd files are built using a word processor and a command set of instructions as outlined below.

It will be appreciated that the preparation of control software and data files is within the routine skill of persons skilled in anotated nucleotide synthesis. The same will depend upon the hardware employed, the chemistries adopted and the design paradigm selected by the operator.

In a like manner to the building the .cmd files, .tab files are built to reflect the necessary reagents used in the automatic synthesizer for the particular chemistries that have been selected for the linkages, bases, sugars and conjugate chemistries. Thus for each of a set of these chemistries at process step 510, a .tab file is built at process step 512 and stored at process step 514. As with the .cmd files, an existing tab file can be edited at process step 516.

Both the .cmd files and the .tab files are linked together at process step 518 and stored for later retrieval in an appropriate sample database 520. Linking can be as simple as using like file names to associate a .cmd file to its appropriate .tab file, e.g., synthesis 1.cmd is linked to synthesis_ 1.tab by use of the same preamble in their names.

Figure 23:
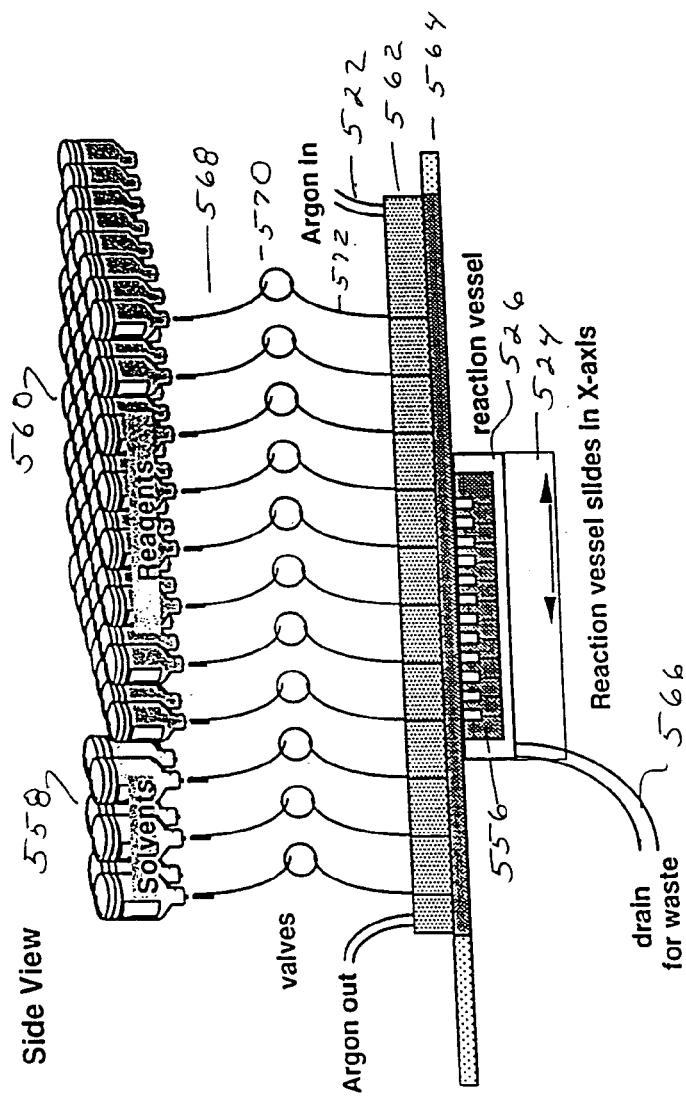
FIG. 23 is a pictorial elevation view of a preferred apparatus used to robotically synthesize oligonucleotides.
Figure 24:
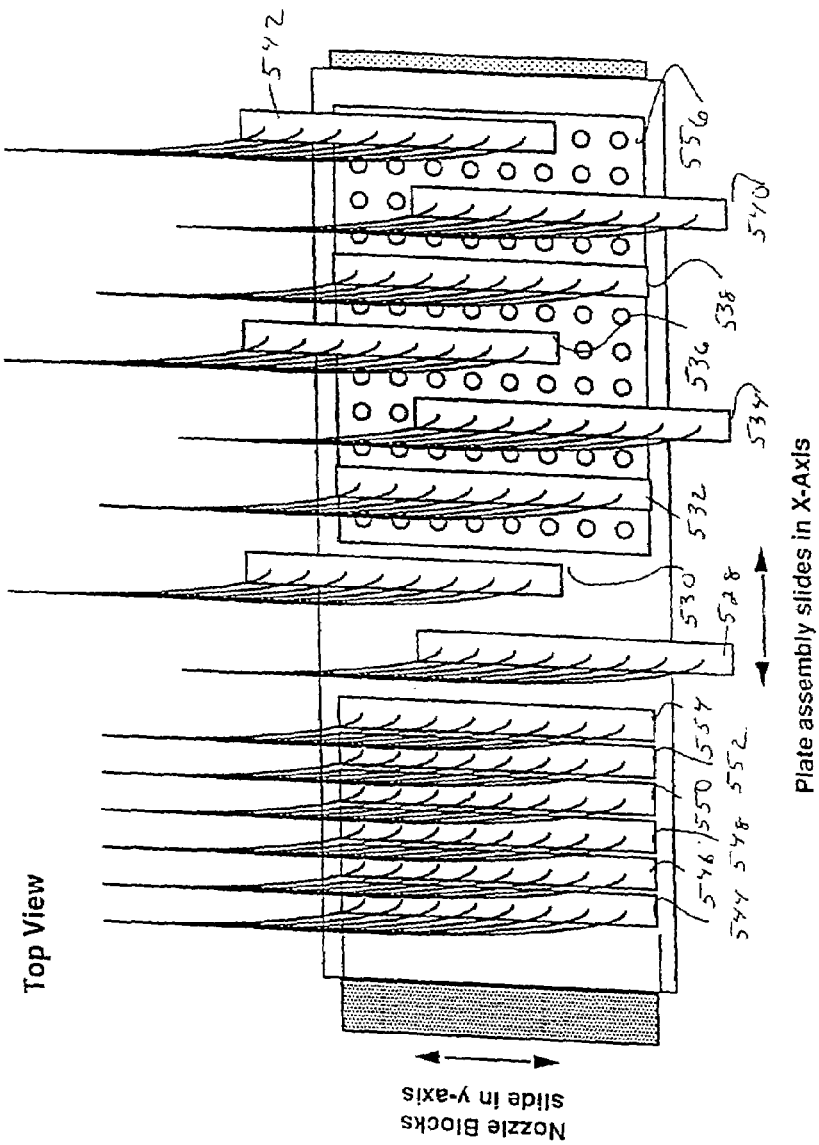
FIG. 24 is a pictorial plan view of an apparatus used to robotically synthesize oligonucleotides.

The automated, multi-well parallel array synthesizer employs a reagent array delivery format, in which each reagent utilized has a dedicated plumbing system. As seen in FIGS. 23 and 24, an inert atmosphere 522 is maintained during all phases of a synthesis. Temperature is controlled via a thermal transfer plate 524, which holds an injection molded reaction block 526. The reaction plate assembly slides in the X-axis direction, while for example eight nozzle blocks (528, 530, 532, 534, 536, 538, 540 and 542) holding the reagent lines slide in the Y-axis direction, allowing for the extremely rapid delivery of any of 64 reagents to 96 wells. In addition, there are for example, six banks of fixed nozzle blocks (544, 546, 548, 550, 552 and 554) which deliver the same reagent or solvent to eight wells at once, for a total of 72 possible reagents.

In synthesizing oligonucleotides for screening, the target reaction vessels, a 96 well plate 556 (a 2-dimensional array), moves in one direction along the X axis, while the series of independently controlled reagent delivery nozzles (528, 530, 532, 534, 536, 538, 540 and 542) move along the Y-axis relative to the reaction vessel 558. As the reaction plate 556 and reagent nozzles (528, 530, 532, 534, 536, 538, 540 and 542) can be moved independently at the same time, this arrangement facilitated the extremely rapid delivery of up to 72 reagents independently to each of the 96 reaction vessel wells.

The system software allows the straightforward programming of the synthesis of a large number of compounds by supplying the general synthetic procedure in the form of the command file to call upon certain reagents to be added to specific wells via lookup in the sequence file with the bottle position, flow rate, and concentration of each reagent being stored in the separate reagent table file. Compounds can be synthesized on various scales. For oligonucleotides, a 200 nmole scale is typically selected while for other compounds larger scales, as for example a 10 µmole scale (3-5 mg), might be utilized. The resulting crude compounds are generally >80% pure, and are utilized directly for high throughput screening assays. Alternatively, prior to use the plates can be subjected to quality control (see general procedure 600 and Example 9) to ascertain their exact purity. Use of the synthesizer results in a very efficient means for the parallel synthesis of compounds for screening.

The software inputs accept tab delimited text files (as discussed above for file 504 and 512) from any text editor. A typical command file, a .cmd file, is shown in Example 3 at Table 2. Typical sequence files, .seq files, are shown in Example 3 at Tables 3 and 4 (.SEQ file), and a typical reagent file, a .tab file, is shown in Example 3 at Table 5. Table 3 illustrates the sequence file for an oligonucleotide having 2'-deoxy nucleotides at each position with a phosphorothioate backbone throughout. Table 4 illustrates the sequence file for an oligonucleotide, again having a phosphorothioate backbone throughout, however, certain modified nucleoside are utilized in portions of the oligonucleotide. As shown in this table, 2'-O-(methoxyethyl) modified nucleoside are utilized in a first region (a wing) of the oligonucleotide, followed by a second region (a gap) of 2'-deoxy nucleotides and finally a third region (a further wing) that has the same chemistry as the first region. Typically some of the wells of the 96 well plate 556 may be left empty (depending on the number of oligonucleotides to be made during an individual synthesis) or some of the well may have oligonucleotides that will serve as standards for comparison or analytical purposes.

Prior to loading reagents, moisture sensitive reagent lines are purged with argon at 522 for 20 minutes. Reagents are dissolved to appropriate concentrations and installed on the synthesizer. Large bottles, collectively identified as 558 in FIG. 23 (containing 8 delivery lines) are used for wash solvents and the delivery of general activators, trityl group cleaving reagents and other reagents that may be used in multiple wells during any particular synthesis. Small septa bottles, collectively identified as 560 in FIG. 23, are utilized to contain individual nucleotide amidite precursor compounds. This allows for anhydrous preparation and efficient installation of multiple reagents by using needles to pressurize the bottle, and as a delivery path. After all reagents are installed, the lines are primed with reagent, flow rates measured, then entered into the reagent table (.tab file). A dry resin loaded plate is removed from vacuum and installed in the machine for the synthesis.

The modified 96 well polypropylene plate 556 is utilized as the reaction vessel. The working volume in each well is approximately 700 μl. The bottom of each well is provided with a pressed-fit 20 μm polypropylene frit and a long capillary exit into a lower collection chamber as is illustrated in FIG. 5 of the above referenced U.S. Pat. No. 5,372,672. The solid support for use in holding the growing oligonucleotide during synthesis is loaded into the wells of the synthesis plate 556 by pipetting the desired volume of a balanced density slurry of the support suspended in an appropriate solvent, typically an acetonitrile-methylene chloride mixture. Reactions can be run on various scales as for instance the above noted 200 nmole and 10 μmol scales. For oligonucleotide synthesis a CPG support is preferred, however other medium loading polystyrene-PEG supports such as TentaGel™ or ArgoGel™ can also be used.

As seen in FIG. 24, the synthesis plate is transported back and forth in the X-direction under an array of 8 moveable banks (530, 532, 534, 536, 538, 540, 542 and 544) of 8 nozzles (64 total) in the Y-direction, and 6 banks (544, 546, 548, 550, 552 and 554) of 48 fixed nozzles, so that each well can receive the appropriate amounts of reagents and/or solvents from any reservoir (large bottle or smaller septa bottle). A sliding balloon-type seal 562 surrounds this nozzle array and joins it to the reaction plate headspace 564. A slow sweep of nitrogen or argon 522 at ambient pressure across the plate headspace is used to preserve an anhydrous environment.

The liquid contents in each well do not drip out until the headspace pressure exceeds the capillary forces on the liquid in the exit nozzle. A slight positive pressure in the lower collection chamber can be added to eliminate residual slow leakage from filled wells, or to effect agitation by bubbling inert gas through the suspension. In order to empty the wells, the headspace gas outlet valve is closed and the internal pressure raised to about 2 psi. Normally, liquid contents are blown directly to waste 566. However, a 96 well microtiter plate can be inserted into the lower chamber beneath the synthesis plate in order to collect the individual well eluents for spectrophotometric monitoring (trityl, etc.) of reaction progress and yield.

The basic plumbing scheme for the machine is the gas-pressurized delivery of reagents. Each reagent is delivered to the synthesis plate through a dedicated supply line, collectively identified at 568, solenoid valve collectively identified at 570 and nozzle,collectively identified at 572. Reagents never cross paths until they reach the reaction well. Thus, no line needs to be washed or flushed prior to its next use and there is no possibility of cross-contamination of reagents. The liquid delivery velocity is sufficiently energetic to thoroughly mix the contents within a well to form a homogeneous solution, even when employing solutions having drastically different densities. With this mixing, once reactants are in homogeneous solution, diffusion carries the individual components into and out of the solid support matrix where the desired reaction takes place. Each reagent reservoir can be plumbed to either a single nozzle or any combination of up to 8 nozzles. Each nozzle is also provided with a concentric nozzle washer to wash the outside of the delivery nozzles in order to eliminate problems of crystallized reactant buildup due to slow evaporation of solvent at the tips of the nozzles. The nozzles and supply lines can be primed into a set of dummy wells directly to waste at any time.

The entire plumbing system is fabricated with teflon tubing, and reagent reservoirs are accessed via syringe needle/septa or direct connection into the higher capacity bottles. The septum vials 560 are held in removable 8-bottle racks to facilitate easy setup and cleaning. The priming volume for each line is about 350 μl. The minimum delivery volume is about 2 μl, and flow rate accuracy is ±5%. The actual amount of material delivered depends on a timed flow of liquid. The flow rate for a particular solvent will depend on its viscosity and wetting characteristics of the teflon tubing. The flow rate (typically 200-350 μl per sec) is experimentally determined, and this information is contained in the reagent table setup file.

Heating and cooling of the reaction block 526 is effected utilizing a recirculating heat exchanger plate 524, similar to that found in PCR thermocyclers, that nests with the polypropylene synthesis plate 556 to provide good thermal contact. The liquid contents in a well can be heated or cooled at about 10° C. per minute over a range of +5 to +80° C., as polypropylene begins to soften and deform at about 80° C. For temperatures greater than this, a non-disposable synthesis plate machined from stainless steel or monel with replaceable frits can be utilized.

The hardware controller can be any of a wide variety, but conveniently can be designed around a set of three 1 MHz 86332 chips. This controller is used to drive the single X-axis and 8 Y-axis stepper motors as well as provide the timing functions for a total of 154 solenoid valves. Each chip has 16 bidirectional timer I/O and 8 interrupt channels in its timer processing unit (TPU). These are used to provide the step and direction signals, and to read 3 encoder inputs and 2 limit switches for controlling up to three motors per chip. Each 86332 chip also drives a serial chain of 8 UNC5891A darlington array chips to provide power to 64 valves with msec resolution. The controller communicates with the Windows software interface program running on a PC via a 19200 Hz serial channel, and uses an elementary instruction set to communicate valve_number, time_open, motor_number and position_data.

The three components of the software program that run the array synthesizer, the generalized procedure or command (.cmd) file which specifies the synthesis instructions to be performed, the sequence (.seq) file which specifies the scale of the reaction and the order in which variable groups will be added to the core synthon, and the reagent table (.tab) file which specifies the name of a chemical, its location (bottle number), flow rate, and concentration are utilized in conjunction with a basic set of command instructions.

One basic set of command instructions can be:

```
ADD
IF              {block of instructions}    END_IF
REPEAT          {block of instructions }   END_REPEAT
PRIME, NOZZLE_WASH
WAIT, DPAIN
LOAD, REMOVE
NEXT_SEQUENCE
LOOP_BEGIN, LOOP
END
```

The ADD instruction has two forms, and is intended to have the look and feel of a standard chemical equation. Reagents are specified to be added by a molar amount if the number proceeds the name identifier, or by an absolute volume in microliters if the number follows the identifier. The number of reagents to be added is a parsed list, separated by the '+' sign. For variable reagent identifiers, the key word, <seq>, means look in the sequence table for the identity of the reagent to be added, while the key word, <act>, means add the reagent which is associated with that particular <seq>. Reagents are delivered in the order specified in the list.

Thus:

```
ADD     ACN 300
        means: Add 300 µl of the named reagent
        acetonitrile; ACN to each well of active synthesis
ADD     <seq> 300
        means: If the sequence pointer in the .seq file
        is to a reagent in the list of reagents,
        independent of scale, add 300 µl of that
        particular reagent specified for that well.
ADD     1.1 PYR + 1.0 <seq> + 1.1 <act1>
        means: If the sequence pointer in the .seq file
        is to a reagent in the list of acids in the Class
        ACIDS_1, and PYR is the name of pyridine, and
        ethyl chloroformate is defined in the .tab file to
        activate the class, ACIDS_1, then this instruction
        means:
            Add    1.1 equiv. pyridine
                   1.0 equiv. of the acid specified for that
                   well and
                   1.1 equiv. of the activator, ethyl
                   chloroformate
```

The IF command allows one to test what type of reagent is specified in the <seq> variable and process the succeeding block of commands accordingly.

Thus:
```
ACYLATION       {the procedure name}
   BEGIN
      IF CLASS = ACIDS_1
         ADD 1.0 <seq> + 1.1 <act1> + 1.1 PYR
         WAIT 60
      ENDIF
      IF CLASS = ACIDS_2
         ADD 1.0 <seq> + 1.2 <act1> + 1.2 TEA
```
```
      ENDIF
      WAIT 60
      DRAIN 10
   END
``` means: Operate on those wells for which reagents contained in the Acid_1 class are specified, WAIT 60 sec, then operate on those wells for which reagents contained in the Acid_2 class are specified, then WAIT 60 sec longer, then DRAIN the whole plate. Note that the Acid_1 group has reacted for a total of 120 sec, while the Acid_2 group has reacted for only 60 sec.

The REPEAT command is a simple way to execute the same block of commands multiple times.

Thus:

```
WASH_1          {the procedure name}
   BEGIN
      REPEAT 3
         ADD ACN 300
         DRAIN 15
      END_REPEAT
   END
``` means: repeats the add acetonitrile and drain sequence for each well three times.

The PRIME command will operate either on specific named reagents or on nozzles which will be used in the next associated <seq> operation. The µl amount dispensed into a prime port is a constant that can be specified in a config.dat file.

The NOZZLE_WASH command for washing the outside of reaction nozzles free from residue due to evaporation of reagent solvent will operate either on specific named reagents or on nozzles which have been used in the preceding associated <seq> operation. The machine is plumbed such that if any nozzle in a block has been used, all the nozzles in that block will be washed into the prime port.

The WAIT and DRAIN commands are by seconds, with the drain command applying a gas pressure over the top surface of the plate in order to drain the wells.

The LOAD and REMOVE commands are instructions for the machine to pause for operator action.

The NEXT_SEQUENCE command increments the sequence pointer to the next group of substituents to be added in the sequence file. The general form of a seq file entry is the definition:

Well_No Well_ID Scale Sequence

The sequence information is conveyed by a series of columns, each of which represents a variable reagent to be added at a particular position. The scale (µmole) variable is included so that reactions of different scale can be run at the same time if desired. The reagents are defined in a lookup table (the .tab file), which specifies the name of the reagent as referred to in the sequence and command files, its location (bottle number), flow rate, and concentration. This information is then used by the controller software and hardware to determine both the appropriate slider motion to position the plate and slider arms for delivery of a specific reagent, as well as the specific valve and time required to deliver the appropriate reagents. The adept classification of reagents allows the use of conditional IF loops from within a command file to perform addition of different reagents differently during a 'single step' performed across 96 wells simultaneously. The special class ACTIVATORS defines certain reagents that always get added with a particular class of reagents (for example tetrazole during a phosphitylation reaction in adding the next nucleotide to a growing oligonucleotide).

The general form of the .tab file is the definition:

Class Bottle Reagent Name Flow_rate Conc.

The LOOP_BEGIN and LOOP_END commands define the block of commands which will continue to operate until a NEXT_SEQUENCE command points past the end of the longest list of reactants in any well.

Not included in the command set is a MOVE command. For all of the above commands, if any plate or nozzle movement is required, this is automatically executed in order to perform the desired solvent or reagent delivery operation. This is accomplished by the controller software and hardware, which determines the correct nozzle(s) and well(s) required for a particular reagent addition, then synchronizes the position of the requisite nozzle and well prior to adding the reagent.

A MANUAL mode can also be utilized in which the synthesis plate and nozzle blocks can be 'homed' or moved to any position by the operator, the nozzles primed or washed, the various reagent bottles depressurized or washed with solvent, the chamber pressurized, etc. The automatic COMMAND mode can be interrupted at any point, MANUAL commands executed, and then operation resumed at the appropriate location. The sequence pointer can be incremented to restart a synthesis anywhere within a command file.

Figure 14:
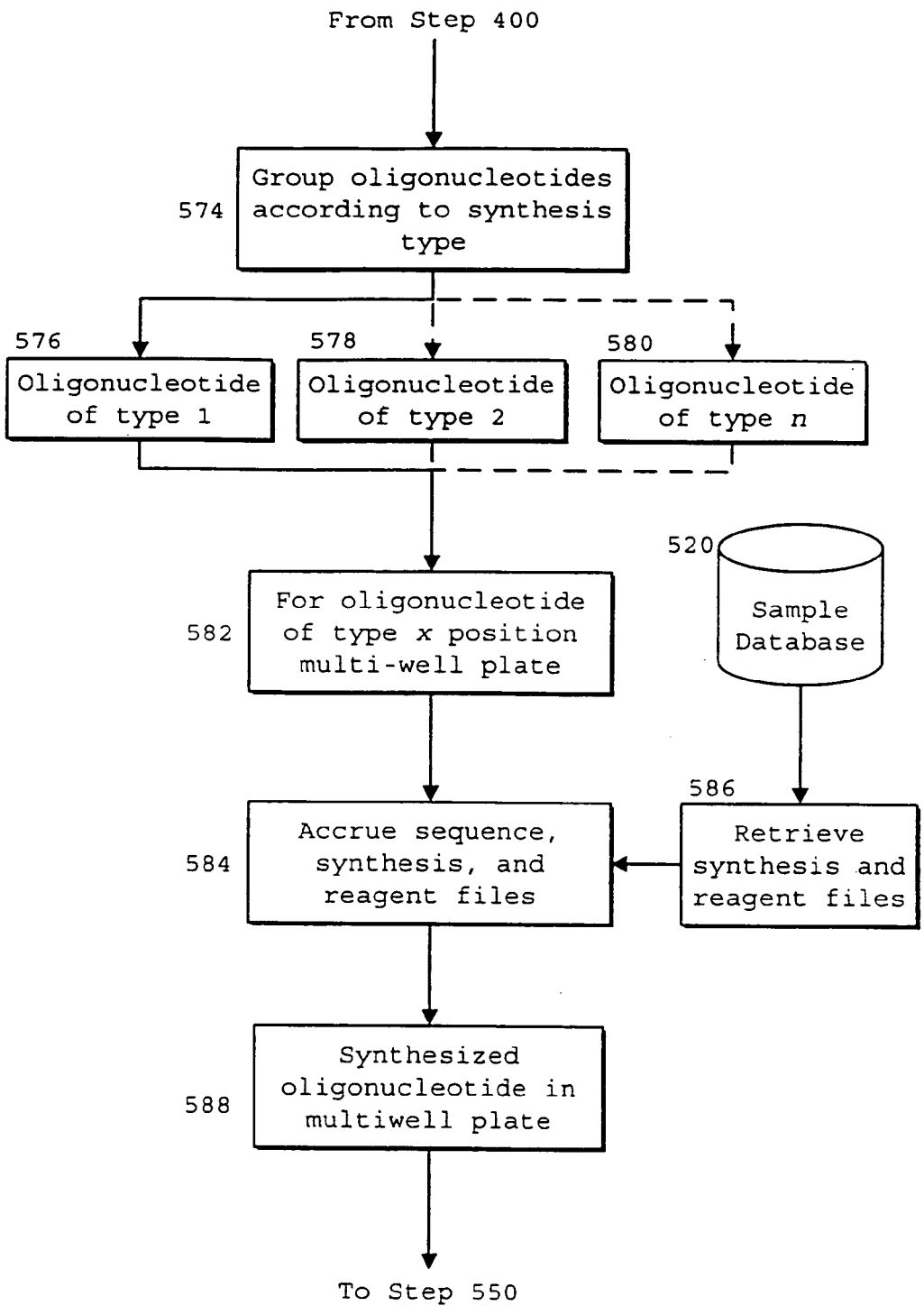

In reference to FIG. 14, the list of oligonucleotides for synthesis can be rearranged or grouped for optimization of synthesis. Thus at process step 574, the oligonucleotides are grouped according to a factor on which to base the optimization of synthesis. As illustrated in the Examples below, one such factor is the 3' most nucleoside of the oligonucleotide. Using the amidite approach for oligonucleotide synthesis, a nucleotide bearing a 3' phosphoramite is added to the 5' hydroxyl group of a growing nucleotide chain. The first nucleotide (at the 3' terminus of the oligonucleotide— the 3' most nucleoside) is first connected to a solid support. This is normally done batchwise on a large scale as is standard practice during oligonucleotide synthesis.

Such solid supports pre-loaded with a nucleoside are commercially available. In utilizing the multi well format for oligonucleotide synthesis, for each oligonucleotide to be synthesized, an aliquot of a solid support bearing the proper nucleoside thereon is added to the well for synthesis. Prior to loading the sequence of oligonucleotides to be synthesized in the .seq file, they are sorted by the 3' terminal nucleotide. Based on that sorting, all of the oligonucleotide sequences having an 'A' nucleoside at their 3' end are grouped together, those with a 'C' nucleoside are grouped together as are those with 'G' or 'T' nucleosides. Thus in loading the nucleoside-bearing solid support into the synthesis wells, machine movements are conserved.

The oligonucleotides can be grouped by the above described parameter or other parameters that facilitate the synthesis of the oligonucleotides. Thus in FIG. 14, sorting is noted as being effected by some parameter of type 1, as for instance the above described 3' most nucleoside, or other types of parameters from type 2 to type n at process steps 576, 578 and 580. Since synthesis will be from the 3' end of the oligonucleotides to the 5' end, the oligonucleotide sequences are reverse sorted to read 3' to 5'. The oligonucleotides are entered in the .seq file in this form, i.e., reading 3' to 5'.

Once sorted into types, the position of the oligonucleotides on the synthesis plates is specified at process step 582 by the creation of a .seq file as described above. The .seq file is associated with the respective .cmd and .tab files needed for synthesis of the particular chemistries specified for the oligonucleotides at process step 584 by retrieval of the .cmd and .tab files at process step 586 from the sample database 520. These files are then input into the multi well synthesizer at process step 588 for oligonucleotide synthesis. Once physically synthesized, the list of oligonucleotides again enters the general procedure flow as indicated in FIG. 1. For shipping, storage or other handling purposes, the plates can be lyophilized at this point if desired. Upon lyophilization, each well contains the oligonucleotides located therein as a dry compound.

14. Quality Control

In an optional step, quality control is performed on the oligonucleotides at process step 600 after a decision is made (decision step 550) to perform quality control. Although optional, quality control may be desired when there is some reason to doubt that some aspect of the synthetic process step 500 has been compromised. Alternatively, samples of the oligonucleotides may be taken and stored in the event that the results of assays conducted using the oligonucleotides (process step 700) yield confusing results or suboptimal data. In the latter event, for example, quality control might be performed after decision step 800 if no oligonucleotides with sufficient activity are identified. In either event, decision step 650 follows quality control step process 600. If one or more of the oligonucleotides do not pass quality control, process step 500 can be repeated, i.e., the oligonucleotides are synthesized for a second time.

Figure 15:
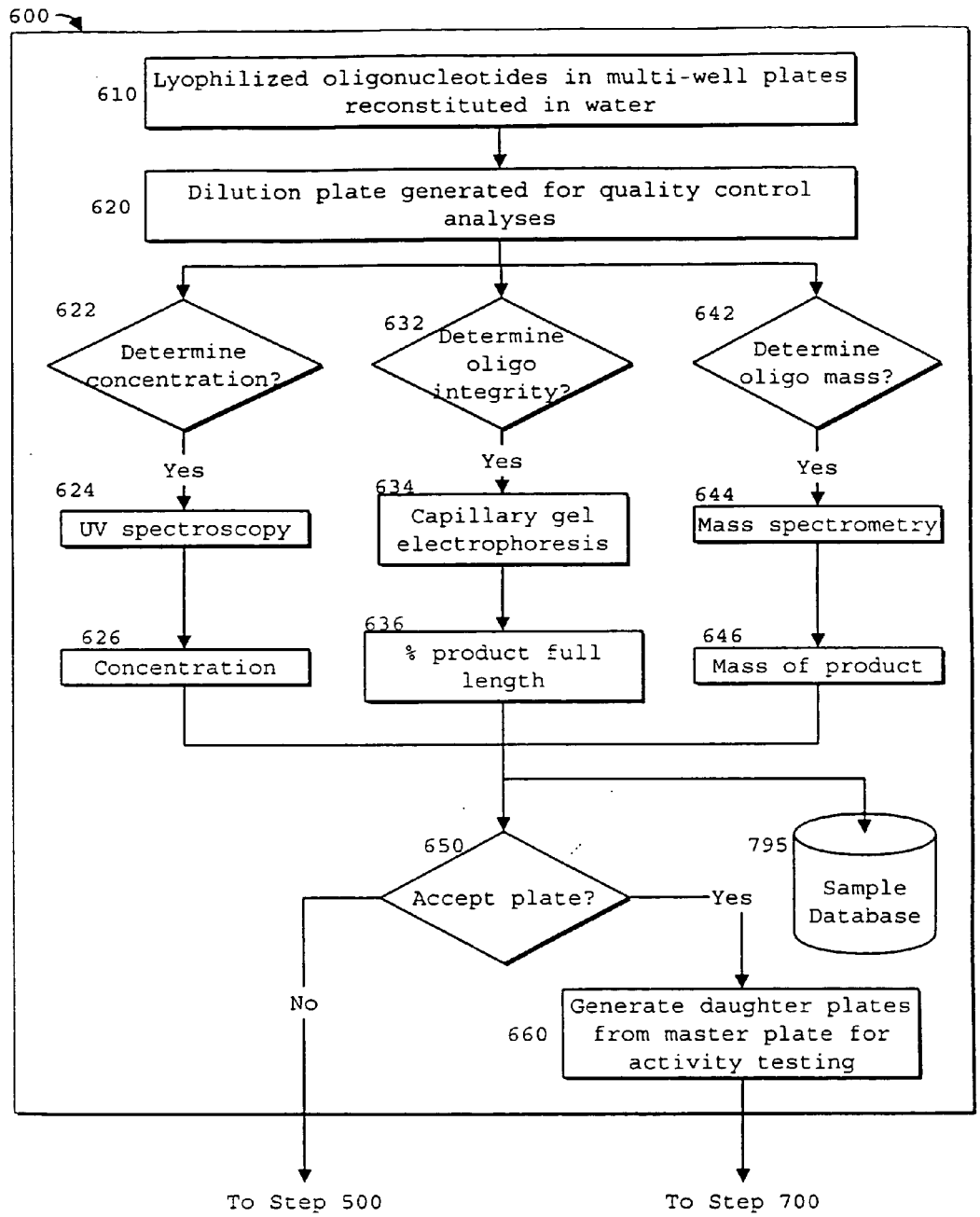
FIG. 15 is a flow diagram depicting the flow of data and materials among elements of step 600 of FIG. 1.
Figure 18:
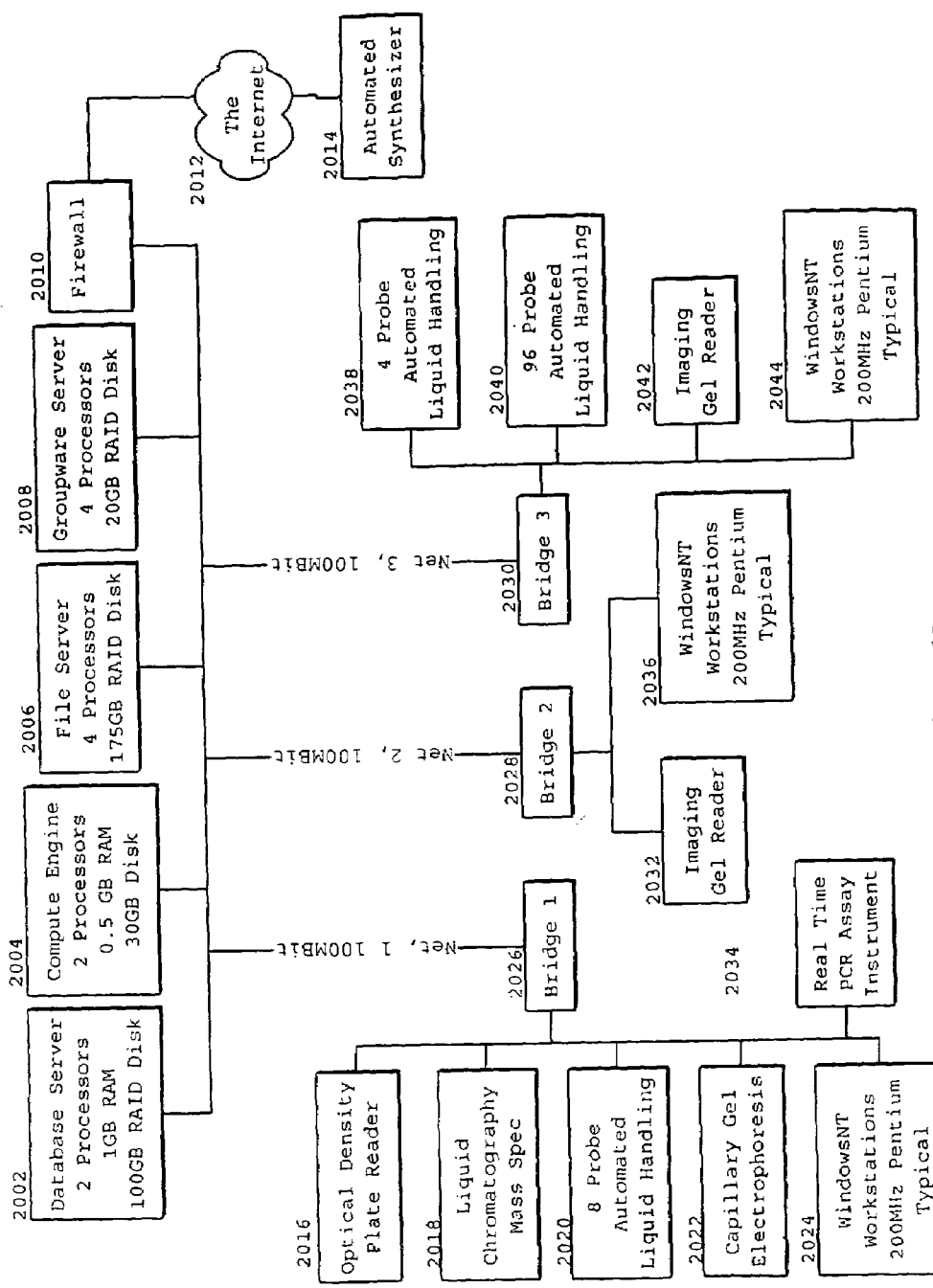
FIG. 18 is a block diagram showing the interconnecting of certain devices utilized in conjunction with a preferred method of the invention.

The operation of the quality control system general procedure 600 is detailed in steps 610-660 of FIG. 15. Also referenced in the following discussion are the robotics and associated analytical instrumentation as shown in FIG. 18.

During step 610 (FIG. 15), sterile, double-distilled water is transferred by an automated liquid handler (2040 of FIG. 18) to each well of a multi-well plate containing a set of lyophilized antisense oligonucleotides. The automated liquid handler (2040 of FIG. 18) reads the barcode sticker on the multi-well plate to obtain the plate's identification number. Automated liquid handler 2040 then queries Sample Database 520 (which resides in Database Server 2002 of FIG. 18) for the quality control assay instruction set for that plate and executes the appropriate steps. Three quality control processes are illustrated, however, it is understood that other quality control processes or steps maybe practiced in addition to or in place of the processes illustrated.

The first illustrative quality control process (steps 622 to 626) quantitates the concentration of oligonucleotide in each well. If this quality control step is performed, an automated liquid handler (2040 of FIG. 18) is instructed to remove an aliquot from each well of the master plate and generate a replicate daughter plate for transfer to the UV spectrophotometer (2016 of FIG. 18). The UV spectrophotometer (2016 of FIG. 18) then measures the optical density of each well at a wavelength of 260 nanometers. Using standardized conversion factors, a microprocessor within UV spectrophotometer (2016 of FIG. 18) then calculates a concentration value from the measured absorbance value for each well and output the results to Sample Database 520.

The second illustrative quality control process steps 632 to 636) quantitates the percent of total oligonucleotide in each well that is full length. If this quality control step is performed, an automated liquid handler (2040 of FIG. 18) is instructed to remove an aliquot from each well of the master plate and generate a replicate daughter plate for transfer to the multichannel capillary gel electrophoresis apparatus (2022 of FIG. 18). The apparatus electrophoretically resolves in capillary tube gels the oligonucleotide product in each well. As the product reaches the distal end of the tube gel during electrophoresis, a detection window dynamically measures the optical density of the product that passes by it. Following electrophoresis, the value of percent product that passed by the detection window with respect to time is utilized by a built in microprocessor to calculate the relative size distribution of oligonucleotide product in each well. These results are then output to the Sample Database (520.

The third illustrative quality control process steps 632 to 636) quantitates the mass of total oligonucleotide in each well that is full length. If this quality control step is performed, an automated liquid handler (2040 of FIG. 18) is instructed to remove an aliquot from each well of the master plate and generate a replicate daughter plate for transfer to the multichannel liquid electrospray mass spectrometer (2018 of FIG. 18). The apparatus then uses electrospray technology to inject the oligonucleotide product into the mass spectrometer. A built in microprocessor calculates the mass-to-charge ratio to arrive at the mass of oligonucleotide product in each well. The results are then output to Sample Database 520.

Following completion of the selected quality control processes, the output data is manually examined or is examined using an appropriate algorithm and a decision is made as to whether or not the plate receives 'Pass' or 'Fail' status. The current criteria for acceptance is that at least 85% of the oligonucleotides in a multi-well plate must be 85% or greater full length product as measured by both capillary gel electrophoresis and mass spectrometry. An input (manual or automated) is then made into Sample Database 520 as to the pass/fail status of the plate. If a plate fails, the process cycles back to step 500, and a new plate of the same oligonucleotides is automatically placed in the plate synthesis request queue (process 554 of FIG. 15). If a plate receives 'Pass' status, an automated liquid handler (2040 of FIG. 18) is instructed to remove appropriate aliquots from each well of the master plate and generate two replicate daughter plates in which the oligonucleotide in each well is at a concentration of 30 micromolar. The plate then moves on to process 700 for oligonucleotide activity evaluation.

15. Cell Lines for Assaying Oligonucleotide Activity

The effect of antisense compounds on target nucleic acid expression can be tested in any of a variety of cell types provided that the target nucleic acid, or its gene product, is present at measurable levels. This can be routinely determined using, for example, PCR or Northern blot analysis. The following four cell types are provided for illustrative purposes, but other cell types can be routinely used.

T-24 cells: The transitional cell bladder carcinoma cell line T-24 is obtained from the American Type Culture Collection (ATCC) (Manassas, Va.). T-24 cells were routinely cultured in complete McCoy's 5A basal media (Life Technologies, Gaithersburg, Md.) supplemented with 10% fetal calf serum, penicillin 100 units per milliliter, and streptomycin 100 micrograms per milliliter (all from Life Technologies). Cells are routinely passaged by trysinization and dilution when they reach 90% confluence. Cells are routinely seeded into 96-well plates (Falcon-Primaria #3872) at a density of 7000 cells/well for use in RT-PCR analysis. For Northern blotting or other analysis, cells are seeded onto 100 mm or other standard tissue culture plates and treated similarly, using appropriate volumes of medium and oligonucleotide.

A549 cells: The human lung carcinoma cell line A549 is obtained from the ATCC (Manassas, Va.). A549 cells were routinely cultured in DMEM basal media (Life Technologies) supplemented with 10% fetal calf serum, penicillin 100 units per milliliter, and streptomycin 100 micrograms per milliliter (all from Life Technologies). Cells are routinely passaged by trysinization and dilution when they reach 90% confluence.

NHDF cells: Human neonatal dermal fibroblast (NHDF) were obtained from the Clonetics Corporation (Walkersville, Md.). NHDFs were routinely maintained in Fibroblast Growth Medium (Clonetics Corp.) as provided by the supplier. Cells are maintained for up to 10 passages as recommended by the supplier.

HEK cells: Human embryonic keratinocytes (HEK) were obtained from the Clonetics Corp. HEKs were routinely maintained in Keratinocyte Growth Medium (Clonetics Corp.) as provided by the supplier. Cell are routinely maintained for up to 10 passages as recommended by the supplier.

16. Treatment of Cells with Candidate Compounds

When cells reach about 80% confluency, they are treated with oligonucleotide. For cells grown in 96-well plates, wells are washed once with 200 µl Opti-MEM-1™ reduced-serum medium (Life Technologies) and then treated with 130 µl of Opti-MEM-1™ containing 3.75 µg/ml LIPOFECTIN (Life Technologies) and the desired oligonucleotide at a final concentration of 150 nM. After 4 hours of treatment, the medium was replaced with fresh medium. Cells were harvested 16 hours after oligonucleotide treatment.

17. Assaying Oligonucleotide Activity oligonucleotide-mediated modulation of expression of a target nucleic acid can be assayed in a variety of ways known in the art. For example, target RNA levels can be quantitated by, e.g., Northern blot analysis, competitive PCR, or reverse transcriptase polymerase chain reaction (RT-PCR). RNA analysis can be performed on total cellular RNA or, preferably in the case of polypeptide-encoding nucleic acids, poly(A)+mRNA. For RT-PCR, poly(A)+ mRNA is preferred. Methods of RNA isolation are taught in, for example, Ausubel et al. (*Short Protocols in Molecular Biology*, 2nd Ed., pp. 4-1 to 4-13, Greene Publishing Associates and John Wiley & Sons, New York, 1992). Northern blot analysis is routine in the art (Id., pp. 4-14 to 4-29). Reverse transcriptase polymerase chain reaction (RT-PCR) can be conveniently accomplished using the commercially available ABI PRISM 7700 Sequence Detection System (PE-Applied Biosystems, Foster City, Calif.) according to manufacturer's instructions. Other methods of PCR are also known in the art.

Target protein levels can be quantitated in a variety of ways well known in the art, such as immunoprecipitation, Western blot analysis (immunoblotting), Enzyme-linked immunosorbent assay (ELISA) or fluorescence-activated cell sorting (FACS). Antibodies directed to a protein encoded by a target nucleic acid can be identified and obtained from a variety of sources, such as the MSRS catalog of antibodies, (Aerie Corporation, Birmingham, Mich. or via the world wide web of the internet at ANTIBODIES-PROBES.com/), or can be prepared via conventional antibody generation methods. Methods for preparation of polyclonal, monospecific ('antipeptide') and monoclonal antisera are taught by, for example, Ausubel et al. (*Short Protocols in Molecular Biology*, 2nd Ed., pp. 11-3 to 11-54, Greene Publishing Associates and John Wiley & Sons, New York, 1992).

Immunoprecipitation methods are standard in the art and are described by, for example, Ausubel et al. (Id., pp. 10-57 to 10-63). Western blot (immunoblot) analysis is standard in the art (Id., pp. 10-32 to 10-10-35). Enzyme-linked immunosorbent assays (ELISA) are standard in the art (Id., pp. 11-5 to 11-17).

Because it is preferred to assay the compounds of the invention in a batchwise fashion, i.e., in parallel to the automated synthesis process described above, preferred means of assaying are suitable for use in 96-well plates and with robotic means. Accordingly, automated RT-PCR is preferred for assaying target nucleic acid levels, and automated ELISA is preferred for assaying target protein levels.

Figure 16:
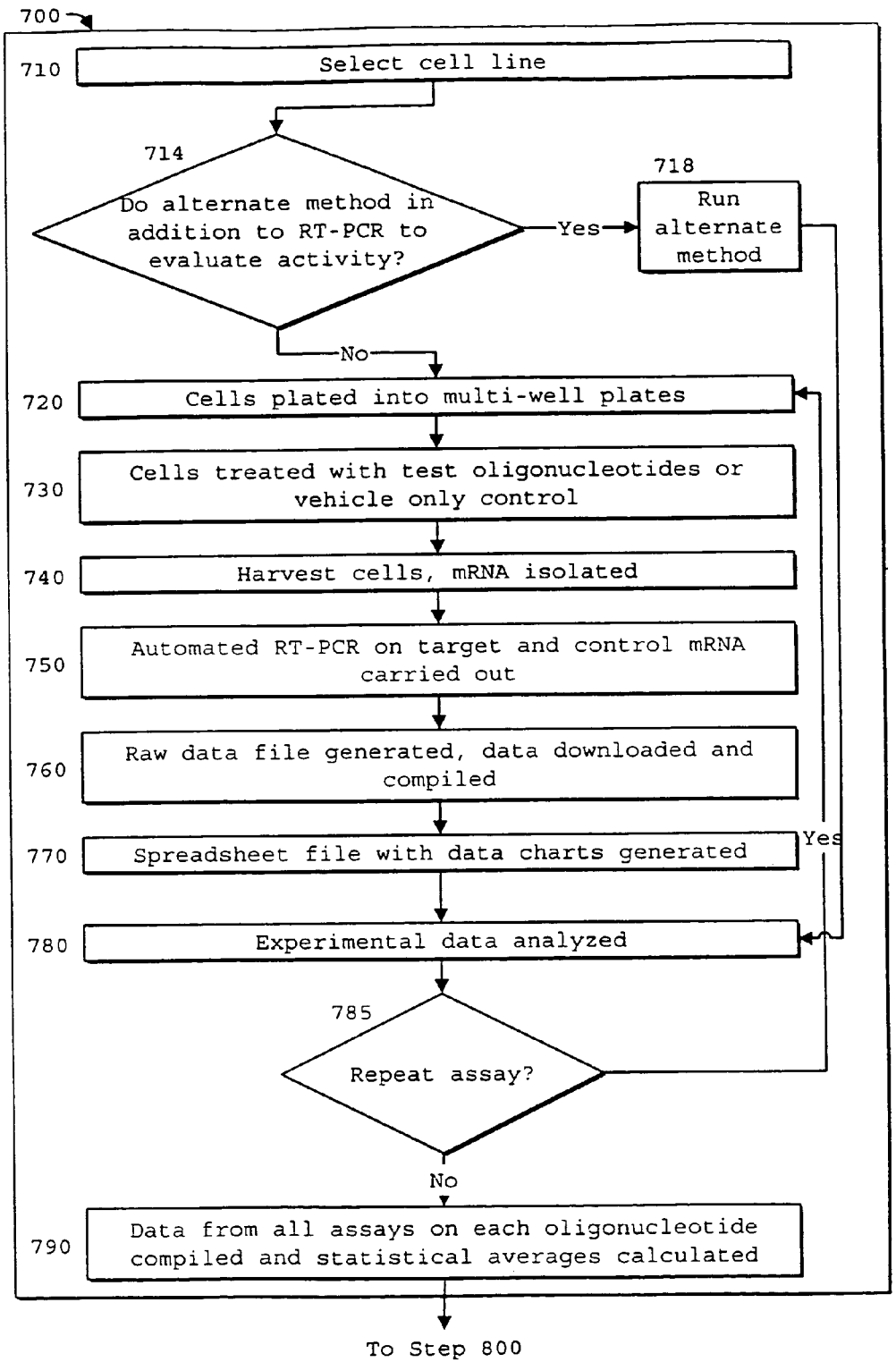
FIG. 16 is a flow diagram depicting the flow of data and materials among elements of step 700 of FIG. 1.

The assaying step, general procedure step 700, is described in detail in FIG. 16. After an appropriate cell line is selected at process step 710, a decision is made at decision step 714 as to whether RT-PCR will be the only method by which the activity of the compounds is evaluated. In some instances, it is desirable to run alternative assay methods at process step 718; for example, when it is desired to assess target polypeptide levels as well as target RNA levels, an immunoassay such as an ELISA is run in parallel with the RT-PCR assays. Preferably, such assays are tractable to semi-automated or robotic means.

When RT-PCR is used to evaluate the activities of the compounds, cells are plated into multi-well plates (typically, 96-well plates) in process step 720 and treated with test or control oligonucleotides in process step 730. Then, the cells are harvested and lysed in process step 740 and the lysates are introduced into an apparatus where RT-PCR is carried out in process step 750. A raw data file is generated, and the data is downloaded and compiled at step 760. Spreadsheet files with data charts are generated at process step 770, and the experimental data is analyzed at process step 780. Based on the results, a decision is made at process step 785 as to whether it is necessary to repeat the assays and, if so, the process begins again with step 720. In any event, data from all the assays on each oligonucleotide are complied and statistical parameters are automatically determined at process step 790.

18. Classification of Compounds Based on Their Activity

Following assaying, general procedure step 700, oligonucleotide compounds are classified according to one or more desired properties. Typically, three classes of compounds are used: active compounds, marginally active (or 'marginal') compounds and inactive compounds. To some degree, the selection criteria for these classes vary from target to target, and members of one or more classes may not be present for a given set of oligonucleotides.

However, some criteria are constant. For example, inactive compounds will typically comprise those compounds having 5% or less inhibition of target expression (relative to basal levels). Active compounds will typically cause at least 30% inhibition of target expression, although lower levels of inhibition are acceptable in some instances. Marginal compounds will have activities intermediate between active and inactive compounds, with preferred marginal compounds having activities more like those of active compounds.

19. Optimization of Lead Compounds by Sequence

One means by which oligonucleotide compounds are optimized for activity is by varying their nucleobase sequences so that different regions of the target nucleic acid are targeted. Some such regions will be more accessible to oligonucleotide compounds than others, and 'sliding' a nucleobase sequence along a target nucleic acid only a few bases can have significant effects on activity. Accordingly, varying or adjusting the nucleobase sequences of the compounds of the invention is one means by which suboptimal compounds can be made optimal, or by which new active compounds can be generated.

Figure 17:
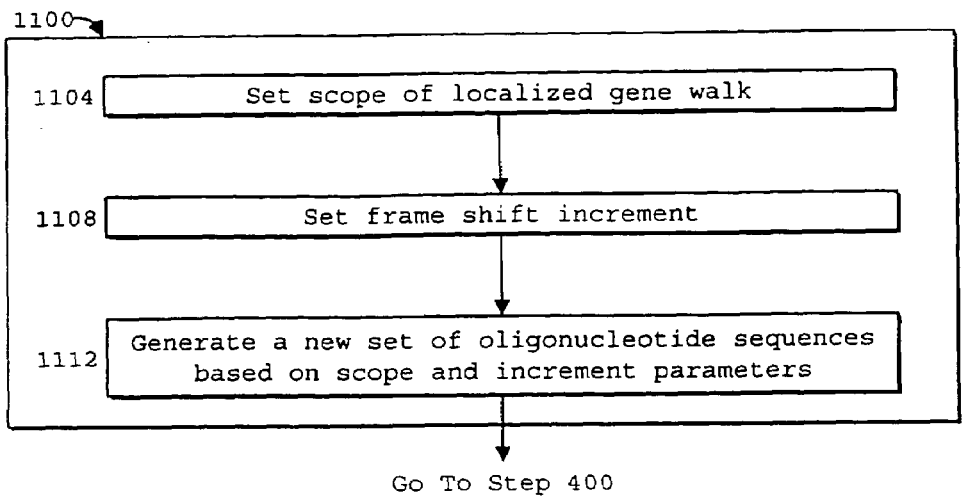
FIG. 17 is a flow diagram depicting the flow of data and materials among the elements of step 1100 of FIG. 2.

The operation of the gene walk process 1100 detailed in steps 1104-1112 of FIG. 17 is detailed as follows. As used herein, the term 'gene walk' is defined as the process by which a specified oligonucleotide sequence x that binds to a specified nucleic acid target y is used as a frame of reference around which a series of new oligonucleotides sequences capable of hybridizing to nucleic acid target y are generated that are sequence shifted increments of oligonucleotide sequence x. Gene walking can be done "downstream", 'upstream' or in both directions from a specified oligonucleotide.

During step 1104 the user manually enters the identification number of the oligonucleotide sequence around which it is desired to execute gene walk process 1100 and the name of the corresponding target nucleic acid. The user then enters the scope of the gene walk at step 1104, by which is meant the number of oligonucleotide sequences that it is desired to generate. The user then enters in step 1108 a positive integer value for the sequence shift increment. Once this data is generated, the gene walk is effected. This causes a subroutine to be executed that automatically generates the desired list of sequences by walking along the target sequence. At that point, the user proceeds to process 400 to assign chemistries to the selected oligonucleotides.

Example 16 below, details a gene walk. In subsequent steps, this new set of nucleobase sequences generated by the gene walk is used to direct the automated synthesis at general procedure step 500 of a second set of candidate oligonucleotides. These compounds are then taken through subsequent process steps to yield active compounds or reiterated as necessary to optimize activity of the compounds.

20. Optimization of Lead Compounds by Chemistry

Another means by which oligonucleotide compounds of the invention are optimized is by reiterating portions of the process of the invention using marginal compounds from the first iteration and selecting additional chemistries to the nucleobase sequences thereof.

Thus, for example, an oligonucleotide chemistry different from that of the first set of oligonucleotides is assigned at general procedure step 400. The nucleobase sequences of marginal compounds are used to direct the synthesis at general procedure step 500 of a second set of oligonucleotides having the second assigned chemistry. The resulting second set of oligonucleotide compounds is assayed in the same manner as the first set at procedure process step 700 and the results are examined to determine if compounds having sufficient activity have been generated at decision step 800.

21. Identification of Sites Amenable to Antisense Technologies

In a related process, a second oligonucleotide chemistry is assigned at procedure step 400 to the nucleobase sequences of all of the oligonucleotides (or, at least, all of the active and marginal compounds) and a second set of oligonucleotides is synthesized at procedure step 500 having the same nucleobase sequences as the first set of compounds. The resulting second set of oligonucleotide compounds is assayed in the same manner as the first set at procedure step 700 and active and marginal compounds are identified at procedure steps 800 and 1000.

In order to identify sites on the target nucleic acid that are amenable to a variety of antisense technologies, the following mathematically simple steps are taken. The sequences of active and marginal compounds from two or more such automated syntheses/assays are compared and a set of nucleobase sequences that are active, or marginally so, in both sets of compounds is identified. The reverse complements of these nucleobase sequences corresponds to sequences of the target nucleic acid that are tractable to a variety of antisense and other sequence-based technologies. These antisense-sensitive sites are assembled into contiguous sequences (contigs) using the procedures described for assembling target nucleotide sequences (at procedure step 200).

22. Systems for Executing Preferred Methods of the Invention

An embodiment of computer, network and instrument resources for effecting the methods of the invention is shown in FIG. 18. In this embodiment, four computer servers are provided. First, a large database server 2002 stores all chemical structure, sample tracking and genomic, assay, quality control, and program status data. Further, this database server serves as the platform for a document management system. Second, a compute engine 2004 runs computational programs including RNA folding, oligonucleotide walking, and genomic searching. Third, a file server 2006 allows raw instrument output storage and sharing of robot instructions. Fourth, a groupware server 2008 enhances staff communication and process scheduling.

A redundant high-speed network system is provided between the main servers and the bridges 2026, 2028 and 2030. These bridges provide reliable network access to the many workstations and instruments deployed for this process. The instruments selected to support this embodiment are all designed to sample directly from standard 96 well microtiter plates, and include an optical density reader 2016, a combined liquid chromatography and mass spectroscopy instrument 2018, a gel fluorescence and scintillation imaging system 2032 and 2042, a capillary gel electrophoreses system 2022 and a real-time PCR system 2034.

Most liquid handling is accomplished automatically using robots with individually controllable robotic pipetters 2038 and 2020 as well as a 96-well pipette system 2040 for duplicating plates. Windows NT or Macintosh workstations 2044, 2024, and 2036 are deployed for instrument control, analysis and productivity support.

23. Relational Database

Figure 19:
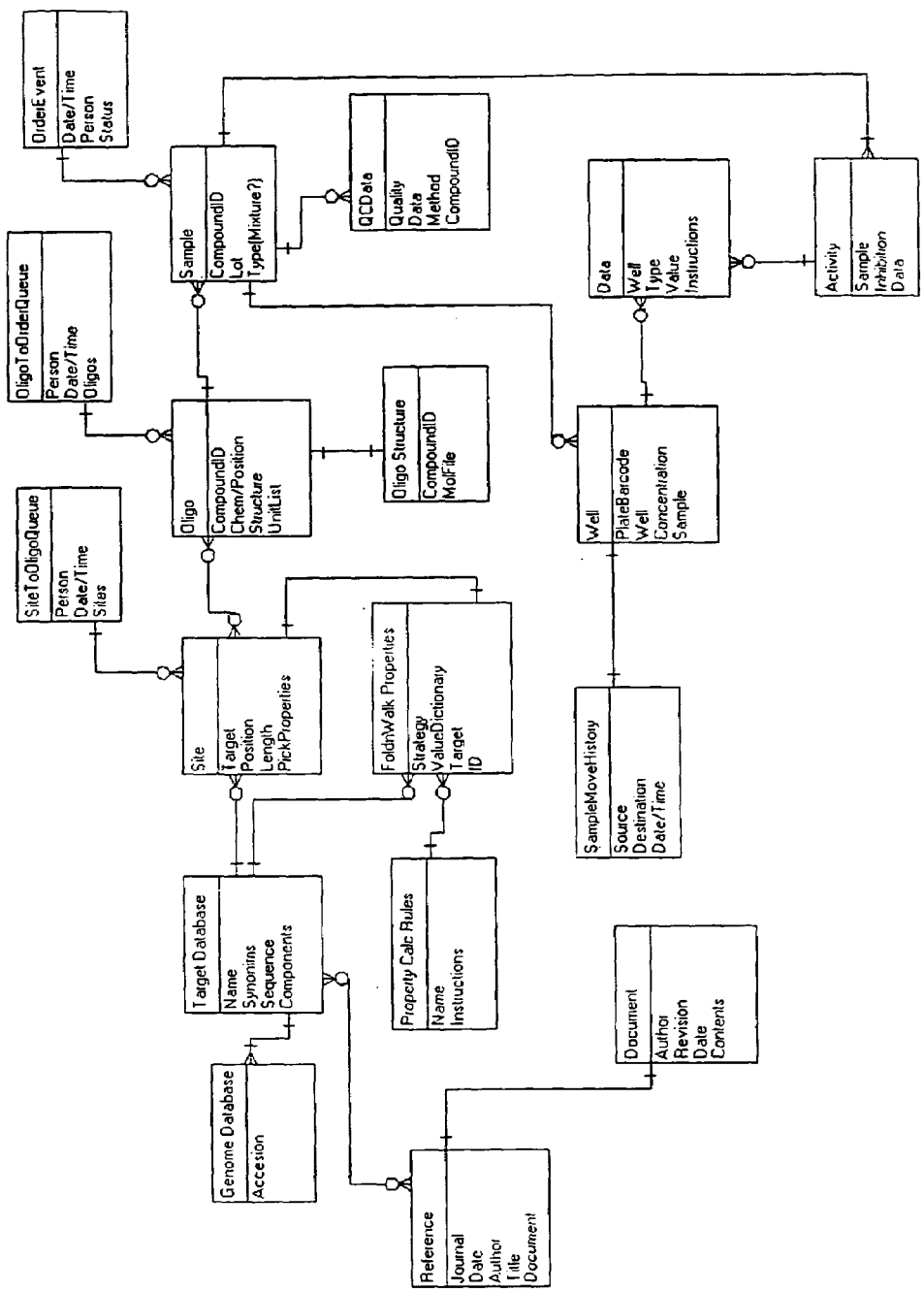
FIG. 19 is a flow diagram showing a representation of data storage in a relational database utilized in conjunction with one method of the invention.

Data is stored in an appropriate database. For use with the methods of the invention, a relational database is preferred. FIG. 19 illustrates the data structure of a sample relational database. Various elements of data are segregated among linked storage elements of the database.

EXAMPLES

The following examples illustrate the invention and are not intended to limit the same. Those skilled in the art will recognize, or be able to ascertain through routine experimentation, numerous equivalents to the specific procedures, materials and devices described herein. Such equivalents are considered to be within the scope of the present invention.

Example 1

Selection of CD40 as a Target

Cell-cell interactions are a feature of a variety of biological processes. In the activation of the immune response, for example, one of the earliest detectable events in a normal inflammatory response is adhesion of leukocytes to the vascular endothelium, followed by migration of leukocytes out of the vasculature to the site of infection or injury. The adhesion of leukocytes to vascular endothelium is an obligate step in their migration out of the vasculature (for a review, see Albelda et al., *FASEB J.,* 1994, 8, 504). As is well known in the art, cell-cell interactions are also critical for propagation of both B-lymphocytes and T-lymphocytes resulting in enhanced humoral and cellular immune responses, respectively (for a reviews, see Makgoba et al., *Immunol. Today,* 1989, 10, 417; Janeway, *Sci. Amer.,* 1993, 269, 72).

CD40 was first characterized as a receptor expressed on B-lymphocytes. It was later found that engagement of B-cell CD40 with CD40L expressed on activated T-cells is essential for T-cell dependent B-cell activation (i.e. proliferation, immunoglobulin secretion, and class switching) (for a review, see Gruss et al. *Leuk. Lymphoma,* 1997, 24, 393). A full cDNA sequence for CD40 is available (GenBank accession number X60592, incorporated herein as SEQ ID NO:85).

As interest in CD40 mounted, it was subsequently revealed that functional CD40 is expressed on a variety of cell types other than B-cells, including macrophages, dendritic cells, thymic epithelial cells, Langerhans cells, and endothelial cells (Ibid.). These studies have led to the current belief that CD40 plays a much broader role in immune regulation by mediating interactions of T-cells with cell types other than B-cells. In support of this notion, it has been shown that stimulation of CD40 in macrophages and dendritic results is required for T-cell activation during antigen presentation (Id.). Recent evidence points to a role for CD40 in tissue inflammation as well. Production of the inflammatory mediators IL-12 and nitric oxide by macrophages has been shown to be CD40 dependent (Buhlmann et al., *J. Clin. Immunol.,* 1996, 16, 83). In endothelial cells, stimulation of CD40 by CD40L has been found to induce surface expression of E-selectin, ICAM-1, and VCAM-1, promoting adhesion of leukocytes to sites of inflammation (Buhlmann et al., *J. Clin. Immunol,* 1996, 16, 83; Gruss et al., *Leuk Lymphoma,* 1997, 24, 393). Finally, a number of reports have documented overexpression of CD40 in epithelial and hematopoietic tumors as well as tumor infiltrating endothelial cells, indicating that CD40 may play a role in tumor growth and/or angiogenesis as well (Gruss et al., *Leuk Lymphoma,* 1997, 24, 393-422; Kluth et al. *Cancer Res,* 1997, 57, 891).

Due to the pivotal role that CD40 plays in humoral immunity, the potential exists that therapeutic strategies aimed at downregulating CD40 may provide a novel class of agents useful in treating a number of immune associated disorders, including but not limited to graft versus host disease, graft rejection, and autoimmune diseases such as multiple sclerosis, systemic lupus erythematosus, and certain forms of arthritis. Inhibitors of CD40 may also prove useful as an anti-inflammatory compound, and could therefore be useful as treatment for a variety of diseases with an inflammatory component such as asthma, rheumatoid arthritis, allograft rejections, inflammatory bowel disease, and various dermatological conditions, including psoriasis. Finally, as more is learned about the association between CD40 overexpression and tumor growth, inhibitors of CD40 may prove useful as anti-tumor agents as well.

Currently, there are no known therapeutic agents which effectively inhibit the synthesis of CD40. To date, strategies aimed at inhibiting CD40 function have involved the use of a variety of agents that disrupt CD40/CD40L binding. These include monoclonal antibodies directed against either CD40 or CD40L, soluble forms of CD40, and synthetic peptides derived from a second CD40 binding protein, A20. The use of neutralizing antibodies against CD40 and/or CD40L in animal models has provided evidence that inhibition of CD40 stimulation would have therapeutic benefit for GVHD, allograft rejection, rheumatoid arthritis, SLE, MS, and B-cell lymphoma (Buhlmann et al., *J. Clin. Immunol*, 1996, 16, 83). However, due to the expense, short half-life, and bioavailability problems associated with the use of large proteins as therapeutic agents, there is a long felt need for additional agents capable of effectively inhibiting CD40 function. oligonucleotides compounds avoid many of the pitfalls of current agents used to block CD40/CD40L interactions and may therefore prove to be uniquely useful in a number of therapeutic applications.

Example 2

Generation of Virtual Oligonucleotides Targeted to CD40

Figure 22:
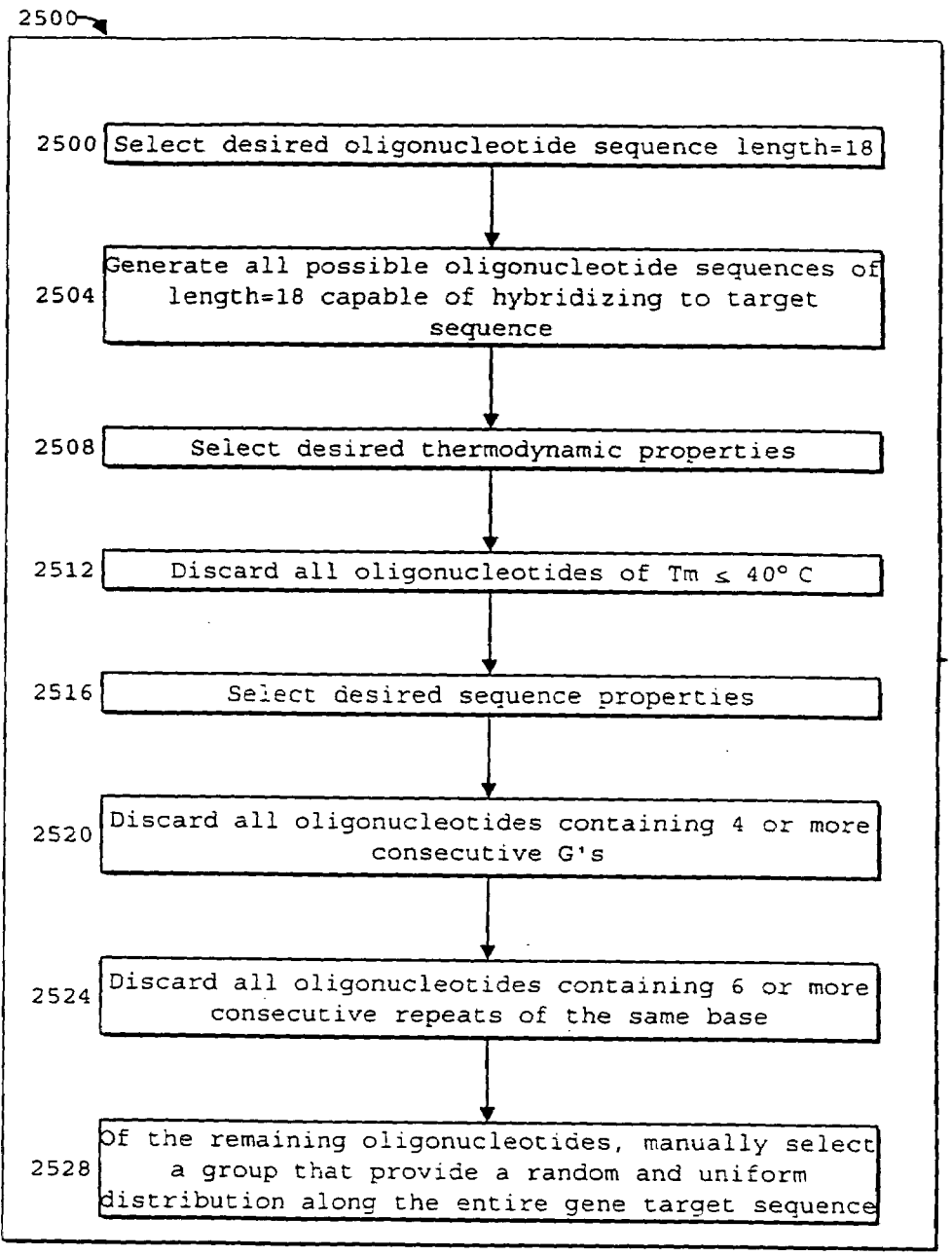
FIG. 22 is a flow diagram depicting the depicting the flow of date and materials in effecting a preferred embodiment of the invention as set forth in Example 2.

The process of the invention was used to select oligonucleotides targeted to CD40, generating the list of oligonucleotide sequences with desired properties as shown in FIG. 22. From the assembled CD40 sequence, the process began with determining the desired oligonucleotide length to be eighteen nucleotides, as represented in step 2500. All possible oligonucleotides of this length were generated by Oligo 5.0™, as represented in step 2504. Desired thermodynamic properties were selected in step 2508. The single parameter used was oligonucleotides of melting temperature less than or equal to 40° C. were discarded. In step 2512, oligonucleotide melting temperatures were calculated by Oligo 5.0™. Oligonucleotide sequences possessing an undesirable score were discarded. It is believed that oligonucleotides with melting temperatures near or below physiological and cell culture temperatures will bind poorly to target sequences. All oligonucleotide sequences remaining were exported into a spreadsheet. In step 2516, desired sequence properties are selected. These include discarding oligonucleotides with at least one stretch of four guanosines in a row and stretches of six of any other nucleotide in a row. In step 2520, a spreadsheet macro removed all oligonucleotides containing the text string 'GGGG'. In step 2524, another spreadsheet macro removed all oligonucleotides containing the text strings 'AAAAAA' or 'CCCCCC' or 'TTTTTT'. From the remaining oligonucleotide sequences, 84 sequences were selected manually with the criteria of having an uniform distribution of oligonucleotide sequences throughout the target sequence, as represented in step 2528. These oligonucleotide sequences were then passed to the next step in the process, assigning actual oligonucleotide chemistries to the sequences.

Example 3

Input Files for Automated Oligonucleotide Synthesis

Command File (.cmd File)

Table 2 is a command file for synthesis of oligonucleotide having regions of 2'-O-(methoxyethyl) nucleosides and region of 2'-deoxy nucleosides each linked by phosphorothioate internucleotide linkages.

TABLE 2

```
SOLID_SUPPORT_SKIP
    BEGIN
        Next_Sequence
    END
INITIAL-WASH
    BEGIN
        Add ACN 300
        Drain 10
    END
LOOP-BEGIN
DEBLOCK
    BEGIN
        Prime TCA
        Load Tray
        Repeat 2
            Add TCA 150
            Wait 10
            Drain 8
        End_Repeat
        Remove Tray
        Add TCA 125
        Wait 10
        Drain 8
    END
WASH_AFTER_DEBLOCK
    BEGIN
        Repeat 3
            Add ACN 250 To_All
            Drain 10
        End_Repeat
    END
COUPLING
    BEGIN
        if class = DEOXY_THIOATE
            Nozzle wash <act1>
            prime <act1>
            prime <seq>
            Add <act1> 70 + <seq> 70
            Wait 40
            Drain 5
        end-if
        if class = MOE_THIOATE
            Nozzle wash <act1>
            Prime <act1>
            prime <seq>
    Add <act1> 120 + <seq> 120
            Wait 230
            Drain 5
        End_if
    END
WASH_AFTER_COUPLING
    BEGIN
        Add ACN 200 To_All
        Drain 10
    END
OXIDIZE
    BEGIN
        if class = DEOXY_THIOATE
            Add BEAU 180
            Wait 40
            Drain 7
        end_if
        if class = MOE_THIOATE
            Add BEAU 200
            Wait 120
```

TABLE 2-continued

```
            Drain 7
            end_if
        END
    CAP
        BEGIN
            Add CAP_B 80 + CAP_A 80
            Wait 20
            Drain 7
        END
    WASH_AFTER_CAP
        BEGIN
            Add ACN 150 To_All
            Drain 5
            Add ACN 250 To_All
            Drain 11
        END
    BASE_COUNTER
        BEGIN
            Next_Sequence
        END
LOOP_END
DEBLOCK_FINAL
    BEGIN
        Prime TCA
        Load Tray
        Repeat 2
            Add TCA 150 To_All
            Wait 10
            Drain 8
        End_Repeat
        Remove Tray
        Add TCA 125 To_All
        Wait 10
        Drain 10
    END
FINAL_WASH
    BEGIN
        Repeat 4
            Add ACN 300 to_All
            Drain_12
        End_Repeat
    END
ENDALL
    BEGIN
        Wait 3
    END
```

Sequence Files (.seq Files)

Table 3 is a .seq file for oligonucleotides having 2'-deoxy nucleosides linked by phosphorothioate internucleotide linkages.

TABLE 3

Identity of columns: Syn #, Well, Scale, Nucleotide at particular position (identified using base identifier followed by backbone identifier where 's' is phosphorothioate). Note the columns wrap around to next line when longer than one line.

| #  | Well | Scale | | | | | | | | | |
|----|------|-----|----|----|----|----|----|----|----|----|----|
| 1  | A01  | 200 | As | Cs | Cs | As | Gs | Gs | As | Cs | Gs |
|    |      |     | Gs | Cs | Gs | Gs | As | Cs | Cs | As | Gs |
| 2  | A02  | 200 | As | Cs | Gs | Gs | Cs | Gs | Gs | As | Cs |
|    |      |     | Cs | As | Gs | As | Gs | Ts | Gs | Gs | As |
| 3  | A03  | 200 | As | Cs | Cs | As | As | Gs | Cs | As | Gs |
|    |      |     | As | Cs | Gs | Gs | As | Gs | As | Cs | Gs |
| 4  | A04  | 200 | As | Cs | Gs | As | Gs | As | Cs | Cs | Cs |
|    |      |     | Cs | Gs | As | Cs | Gs | As | As | Cs | Gs |
| 5  | A05  | 200 | As | Cs | Cs | Cs | Cs | Gs | As | Cs | Gs |
|    |      |     | As | As | Cs | Gs | As | Cs | Ts | Gs | Gs |
| 6  | A06  | 200 | As | Cs | Gs | As | As | Cs | Gs | As | Cs |
|    |      |     | Ts | Gs | Gs | Cs | Gs | As | Cs | As | Gs |
| 7  | A07  | 200 | As | Cs | Gs | As | Cs | Ts | Gs | Gs | Cs |
|    |      |     | Gs | As | Cs | As | Gs | Gs | Ts | As | Gs |
| 8  | A08  | 200 | As | Cs | As | Gs | Gs | Ts | As | Gs | Gs |
|    |      |     | Ts | Cs | Ts | Ts | Gs | Gs | Ts | Gs | Gs |
| 9  | A09  | 200 | As | Gs | Gs | Ts | Cs | Ts | Ts | Gs | Gs |
|    |      |     | Ts | Gs | Gs | Gs | Ts | Gs | As | Cs | Gs |
| 10 | A10  | 200 | As | Gs | Ts | Cs | As | Cs | Gs | As | Cs |
|    |      |     | As | As | Gs | As | As | As | Cs | As | Cs |
| 11 | A11  | 200 | As | Cs | Gs | As | Cs | As | As | Gs | As |
|    |      |     | As | As | Cs | As | Cs | Gs | Gs | Ts | Cs |
| 12 | A12  | 200 | As | Gs | As | As | As | Cs | As | Cs | Gs |
|    |      |     | Gs | Ts | Cs | Gs | Gs | Ts | Cs | Cs | Ts |
| 13 | B01  | 200 | As | As | Cs | As | Cs | Gs | Gs | Ts | Cs |
|    |      |     | Gs | Gs | Ts | Cs | Cs | Ts | Gs | Ts | Cs |
| 14 | B02  | 200 | As | Cs | Ts | Cs | As | Cs | Ts | Gs | As |
|    |      |     | Cs | Gs | Ts | Gs | Ts | Cs | Ts | Cs | As |
| 15 | B03  | 200 | As | Cs | Gs | Gs | As | As | Gs | Gs | As |
|    |      |     | As | Cs | Gs | Cs | Gs | As | Cs | Ts | Ts |
| 16 | B04  | 200 | As | Ts | Cs | Ts | Gs | Ts | Gs | Gs | As |
|    |      |     | Cs | Cs | Ts | Ts | Gs | Ts | Cs | Ts | Cs |
| 17 | B05  | 200 | As | Cs | As | Cs | Ts | Ts | Cs | Ts | Ts |
|    |      |     | Cs | Cs | Gs | As | Cs | Cs | Gs | Ts | Gs |
| 18 | B06  | 200 | As | Cs | Ts | Cs | Ts | Cs | Gs | As | Cs |
|    |      |     | As | Cs | As | Gs | Gs | As | Cs | Gs | Ts |
| 19 | B07  | 200 | As | As | As | Cs | Cs | Cs | Cs | As | Gs |
|    |      |     | Ts | Ts | Cs | Gs | Ts | Cs | Ts | As | As |
| 20 | B08  | 200 | As | Ts | Gs | Ts | Cs | Cs | Cs | Cs | As |
|    |      |     | As | As | Gs | As | Cs | Ts | As | Ts | Gs |
| 21 | B09  | 200 | As | Cs | Gs | Cs | Ts | Cs | Gs | Gs | Gs |
|    |      |     | As | Cs | Gs | Gs | Gs | Ts | Cs | As | Gs |
| 22 | B10  | 200 | As | Cs | Gs | Cs | Cs | As | As | Gs | As |
|    |      |     | As | Gs | As | Gs | Ts | Ts | As | Cs |    |
| 23 | B11  | 200 | As | Cs | As | Cs | As | Gs | Ts | As | Gs |
|    |      |     | As | Cs | Gs | As | As | As | Gs | Cs | Ts |
| 24 | B12  | 200 | As | Cs | As | Cs | Ts | Cs | Ts | Gs | Gs |
|    |      |     | Ts | Ts | Ts | Cs | Ts | Gs | Gs | As | Cs |
| 25 | C01  | 200 | As | Cs | Gs | As | Cs | Cs | As | Gs | As |
|    |      |     | As | As | Ts | As | Gs | Ts | Ts | Ts | Ts |
| 26 | C02  | 200 | As | Gs | Ts | Ts | As | As | As | As | Gs |
|    |      |     | Gs | Gs | Cs | Ts | Gs | Cs | Ts | As | Gs |
| 27 | C03  | 200 | As | Gs | Gs | Ts | Ts | Gs | Ts | Gs | As |
|    |      |     | Cs | Gs | As | Cs | Gs | As | Gs | Gs | Ts |
| 28 | C04  | 200 | As | As | Ts | Gs | Ts | As | Cs | Cs | Ts |
|    |      |     | As | Cs | Gs | Gs | Ts | Ts | Gs | Gs | Cs |
| 29 | C05  | 200 | As | Gs | Ts | Cs | As | Cs | Gs | Ts | Cs |
|    |      |     | Cs | Ts | Cs | Ts | Cs | Ts | Gs | Ts | Cs |
| 30 | C06  | 200 | Cs | Ts | Gs | Cs | Gs | Cs | As | Cs | As |
|    |      |     | Gs | Gs | Ts | As | Gs | Gs | Ts | Cs | Ts |
| 31 | C07  | 200 | Cs | Ts | Cs | Ts | Gs | Ts | Gs | Ts | Gs |
|    |      |     | As | Cs | Gs | Gs | Ts | Gs | Gs | Ts | Cs |
| 32 | C08  | 200 | Cs | As | Gs | Gs | Ts | Cs | Gs | Ts | Cs |
|    |      |     | Ts | Ts | Cs | Cs | Cs | Gs | Ts | Gs | Gs |
| 33 | C09  | 200 | Cs | Ts | Gs | Ts | Gs | Gs | Ts | As | Gs |
|    |      |     | As | Cs | Gs | Ts | Gs | Gs | As | Cs | As |
| 34 | C10  | 200 | Cs | Ts | As | As | Cs | Gs | As | Ts | Gs |
|    |      |     | Ts | Cs | Cs | Cs | As | As | As | Gs |    |
| 35 | C11  | 200 | Cs | Ts | Gs | Ts | Ts | Cs | Gs | As | Cs |
|    |      |     | As | Cs | Ts | Cs | Ts | Gs | Gs | Ts | Ts |
| 36 | C12  | 200 | Cs | Ts | Gs | Gs | As | Cs | Cs | As | As |
|    |      |     | Cs | As | Cs | Gs | Ts | Gs | Ts | Cs |    |
| 37 | D01  | 200 | Cs | Cs | Gs | Ts | Cs | Cs | Gs | Ts | Gs |
|    |      |     | Ts | Ts | Ts | Gs | Ts | Ts | Cs | Ts | Gs |
| 38 | D02  | 200 | Cs | Ts | Gs | As | Cs | Ts | As | Cs | As |
|    |      |     | As | Cs | As | Gs | As | Cs | As | Cs |    |
| 39 | D03  | 200 | Cs | As | As | Cs | As | Gs | As | Cs | As |
|    |      |     | Cs | Cs | As | Gs | Gs | Gs | Ts | Cs |    |
| 40 | D04  | 200 | Cs | As | Gs | Gs | Gs | Gs | Ts | Cs | Cs |
|    |      |     | Ts | As | Gs | Cs | Cs | Gs | As | Cs | Ts |
| 41 | D05  | 200 | Cs | Ts | Cs | Ts | As | Gs | Ts | Ts | As |
|    |      |     | As | As | Gs | Gs | Cs | Ts | Gs |    |    |
| 42 | D06  | 200 | Cs | Ts | Gs | Cs | Ts | As | Gs | As | As |
|    |      |     | Gs | Gs | As | Cs | Gs | As | Gs | Gs |    |
| 43 | D07  | 200 | Cs | Ts | Gs | As | As | As | Ts | Gs | Ts |
|    |      |     | As | Cs | Cs | Ts | As | Cs | Gs | Gs | Ts |
| 44 | D08  | 200 | Cs | As | Cs | Cs | Cs | Gs | Ts | Ts | Ts |
|    |      |     | Gs | Ts | Cs | Cs | Gs | Ts | Cs | As | As |

TABLE 3-continued

Identity of columns: Syn #, Well, Scale, Nucleotide at particular position (identified using base identifier followed by backbone identifier where 's' is phosphorothioate). Note the columns wrap around to next line when longer than one line.

| # | Well | Scale | | | | | | | | | |
|---|------|-------|---|---|---|---|---|---|---|---|---|
| 45 | D09 | 200 | Cs | Ts | Cs | Gs | As | Ts | As | Cs | Gs |
|    |     |     | Gs | Gs | Ts | Cs | As | Gs | Ts | Cs | As |
| 46 | D10 | 200 | Gs | Gs | Ts | As | Gs | Gs | Ts | Cs | Ts |
|    |     |     | Ts | Gs | Gs | Ts | Gs | Gs | Gs | Ts | Gs |
| 47 | D11 | 200 | Gs | As | Cs | Ts | Ts | Ts | Gs | Cs | Cs |
|    |     |     | Ts | Ts | As | Cs | Gs | Gs | As | As | Gs |
| 48 | D12 | 200 | Gs | Ts | Gs | Gs | As | Gs | Ts | Cs | Ts |
|    |     |     | Ts | Ts | Gs | Ts | Cs | Ts | Gs | Ts | Gs |
| 49 | E01 | 200 | Gs | Gs | As | Gs | Ts | Cs | Ts | Ts | Ts |
|    |     |     | Gs | Ts | Cs | Ts | Gs | Ts | Gs | Gs | Ts |
| 50 | E02 | 200 | Gs | Gs | As | Cs | As | Cs | Ts | Cs | Ts |
|    |     |     | Cs | Gs | As | Cs | As | Cs | As | Gs | Gs |
| 51 | E03 | 200 | Gs | As | Cs | As | Cs | As | Gs | Gs | As |
|    |     |     | Cs | Gs | Ts | Gs | Gs | Cs | Gs | As | Gs |
| 52 | E04 | 200 | Gs | As | Gs | Ts | As | Cs | Gs | As | Gs |
|    |     |     | Cs | Gs | Os | Gs | Cs | Cs | Gs | As | As |
| 53 | E05 | 200 | Gs | As | Cs | Ts | As | Ts | Gs | Gs | Ts |
|    |     |     | As | Gs | As | Cs | Gs | Cs | Ts | Cs | Gs |
| 54 | E06 | 200 | Gs | As | As | Gs | As | Gs | Gs | Ts | Ts |
|    |     |     | As | Cs | As | Cs | As | Gs | Ts | As | Gs |
| 55 | E07 | 200 | Gs | As | Gs | Gs | Ts | Ts | As | Cs | As |
|    |     |     | Cs | As | Gs | Ts | As | Gs | As | Cs | Gs |
| 56 | E08 | 200 | Gs | Ts | Ts | Gs | Ts | Cs | Gs | Ts |    |
|    |     |     | Cs | Cs | Gs | Ts | Gs | Ts | Ts | Ts | Gs |
| 57 | E09 | 200 | Gs | As | Cs | Ts | Cs | Ts | Cs | Gs | Gs |
|    |     |     | Gs | As | Cs | Cs | As | Cs | Cs | As | Cs |
| 58 | E10 | 200 | Gs | Ts | As | Gs | Gs | As | Gs | As | As |
|    |     |     | Cs | Cs | As | Cs | Gs | As | Cs | Cs | As |
| 59 | E11 | 200 | Gs | Gs | Ts | Ts | Cs | Ts | Ts | Cs | Gs |
|    |     |     | Gs | Ts | Ts | Gs | Gs | Ts | Ts | As | Ts |
| 60 | E12 | 200 | Gs | Ts | Gs | Gs | Gs | Gs | Ts | Ts | Cs |
|    |     |     | Gs | Ts | Cs | Cs | Ts | Ts | Gs | Cs | Gs |
| 61 | F01 | 200 | Gs | Ts | Cs | As | Cs | Gs | Ts | Cs | Cs |
|    |     |     | Ts | Cs | Ts | Cs | As | As | As | Ts | Gs |
| 62 | F02 | 200 | Gs | Ts | Cs | Cs | Ts | Cs | Cs | Ts | As |
|    |     |     | Cs | Cs | Gs | Ts | Ts | Ts | Cs | Ts | Cs |
| 63 | F03 | 200 | Gs | Ts | Cs | Cs | Cs | Cs | As | Cs | Cs |
|    |     |     | Ts | Cs | Cs | Gs | Ts | Cs | Ts | Ts | Cs |
| 64 | F04 | 200 | Ts | Cs | As | Cs | Cs | As | Gs | Gs | As |
|    |     |     | Cs | Gs | Gs | Cs | Gs | Cs | As | Cs | Cs |
| 65 | F05 | 200 | Ts | As | Cs | Cs | As | As | Cs | Cs | As |
|    |     |     | Gs | As | Cs | Gs | Gs | As | Gs | As | Cs |
| 66 | F06 | 200 | Ts | Cs | Cs | Ts | Gs | Ts | Cs | Ts | Ts |
|    |     |     | Ts | Cs | As | Cs | Cs | As | Cs | Ts | Cs |
| 67 | F07 | 200 | Ts | Gs | Ts | Cs | Ts | Ts | Ts | Gs | As |
|    |     |     | Cs | Cs | As | Cs | Ts | Cs | As | Cs | Ts |
| 68 | F08 | 200 | Ts | Gs | As | Cs | Cs | As | Cs | Ts | Cs |
|    |     |     | As | Cs | Ts | Gs | As | Cs | Gs | Ts | Gs |
| 69 | F09 | 200 | Ts | Cs | As | Cs | Cs | Ts | Gs | Ts | Cs |
|    |     |     | Ts | Cs | As | As | Gs | Ts | Gs | As | Cs |
| 70 | F10 | 200 | Ts | Cs | As | As | Gs | Ts | Gs | As | Cs |
|    |     |     | Ts | Ts | Ts | Gs | Cs | Cs | Ts | Ts | As |
| 71 | F11 | 200 | Ts | Cs | Ts | Ts | Ts | As | Ts | Gs | As |
|    |     |     | Cs | Gs | Cs | Ts | Cs | Gs | Cs | Gs | Ts |
| 72 | F12 | 200 | Ts | Ts | As | Ts | Gs | As | Cs | Gs | Cs |
|    |     |     | Ts | Gs | Cs | Gs | Cs | Ts | Ts | Gs | Gs |
| 73 | G01 | 200 | Ts | Gs | As | Cs | Cs | Cs | Ts | Cs | Cs |
|    |     |     | Gs | Gs | Ts | Ts | Cs | Gs | As | Ts | Cs |
| 74 | G02 | 200 | Ts | Cs | Cs | Ts | Cs | Ts | Ts | Cs | Cs |
|    |     |     | Cs | Gs | Ts | Gs | Gs | As | Gs | Ts | Cs |
| 75 | G03 | 200 | Ts | Gs | Cs | Ts | As | Gs | As | Cs | Gs |
|    |     |     | Ts | Cs | Cs | As | Cs | As | Cs | Ts | Ts |
| 76 | G04 | 200 | Ts | Ts | Cs | Ts | Ts | Cs | Cs | Gs | As |
|    |     |     | Cs | Cs | Cs | Ts | Cs | As | Cs | As | Ts |
| 77 | G05 | 200 | Ts | Cs | Cs | Ts | As | Cs | As | Cs | Cs |
|    |     |     | Cs | Ts | Cs | Cs | Cs | Cs | As | Cs | Cs |
| 78 | G06 | 200 | Ts | As | Cs | As | Cs | Cs | Cs | Ts | Cs |
|    |     |     | Gs | Gs | Gs | As | Cs | Gs | Gs | Gs | Ts |
| 79 | G07 | 200 | Ts | Ts | Ts | Ts | As | Cs | As | Gs | Ts |
|    |     |     | Gs | Gs | Gs | As | As | Cs | Cs | Ts | Gs |
| 80 | G08 | 200 | Ts | Gs | Gs | Gs | As | As | Cs | Cs | Ts |
|    |     |     | Gs | Ts | Ts | Cs | Gs | As | Cs | As | Cs |
| 81 | G09 | 200 | Ts | Cs | Gs | Gs | Gs | As | Cs | Cs | As |
|    |     |     | Cs | Cs | As | Cs | Ts | As | Gs | Gs | Gs |
| 82 | G10 | 200 | Ts | As | Gs | Gs | As | Cs | As | As | As |
|    |     |     | Cs | Gs | Gs | Ts | As | Gs | As | Gs |    |
| 83 | G11 | 200 | Ts | Gs | Cs | Ts | As | Gs | As | As | Gs |
|    |     |     | Gs | As | Cs | Cs | Gs | As | Gs | Gs | Ts |
| 84 | G12 | 200 | Ts | Cs | Ts | Gs | Ts | Cs | As | Cs | Ts |
|    |     |     | Cs | Cs | Gs | As | Cs | Gs | Ts | Gs | Gs |

Table 4 is a .seq file for oligonucleotides having regions of 2'-O-(methoxyethyl)nucleosides and region of 2'-deoxy nucleosides each linked by phosphorothioate internucleotide linkages.

TABLE 4

Identity of columns: Syn #, Well, Scale, Nucleotide at particular position (identified using base identifier followed by backbone identifier where 's' is phosphorothioate and 'moe' indicated a 2'-O-(methoxyethy) substituted nucleoside). The columns wrap around to next line when longer than one line.

| # | Well | Scale | | | | | | | | | |
|---|------|-------|---|---|---|---|---|---|---|---|---|
| 1 | A01 | 200 | moeAs |   | moeCs |   | moeCs |   | moeAs |   | Gs |
|   |     |     | Gs | As | Cs | Gs | Gs | Cs | Gs | Gs | As | moeCs |
|   |     |     | moeCs |   | moeAs |   | moeGs |   |   |   |   |
| 2 | A02 | 200 | moeAs |   | moeCs |   | moeGs |   | moeGs |   | Cs |
|   |     |     | Gs | Gs | As | Cs | Cs | As | Gs | As | Gs | moeTs |
|   |     |     | moeGs |   | moeGs |   | moeAs |   |   |   |   |
| 3 | A03 | 200 | moeAs |   | moeCs |   | moeCs |   | moeAs |   | As |
|   |     |     | Gs | Cs | As | Gs | As | Cs | Gs | As | Gs | moeGs |
|   |     |     | moeAs |   | moeCs |   | moeGs |   |   |   |   |
| 4 | A04 | 200 | moeAs |   | moeGs |   | moeGs |   | moeAs |   | Gs |
|   |     |     | As | Cs | Cs | Cs | Cs | Gs | As | Cs | Gs | moeAs |
|   |     |     | moeAs |   | moeCs |   | moeGs |   |   |   |   |
| 5 | A05 | 200 | moeAs |   | moeCs |   | moeCs |   | moeCs |   | Cs |
|   |     |     | Gs | As | Cs | Gs | As | As | Cs | Gs | As | moeCs |
|   |     |     | moeTs |   | moeGs |   | moeGs |   |   |   |   |
| 6 | A06 | 200 | moeAs |   | moeCs |   | moeGs |   | moeAs |   | As |
|   |     |     | Cs | Gs | As | Cs | Ts | Gs | Gs | Cs | Gs | moeAs |
|   |     |     | moeCs |   | moeAs |   | moeGs |   |   |   |   |

TABLE 4-continued

Identity of columns: Syn #, Well, Scale, Nucleotide at particular position (identified using base identifier followed by backbone identifier where 's' is phosphorothioate and 'moe' indicated a 2'-O-(methoxyethy) substituted nucleoside). The columns wrap around to next line when longer than one line.

| # | Well | Scale | | | | | | | | | |
|---|------|-------|---|---|---|---|---|---|---|---|---|
| 7 | A07 | 200 | moeAs | moeCs | moeGs | moeAs | Cs | | | | |
|   |     |     | Ts | Gs | Gs | Cs | Gs | As | Cs | As | Gs | moeGs |
|   |     |     | moeTs | moeAs | moeGs | | | | | | |
| 8 | A08 | 200 | moeAs | moeCs | moeAs | moeGs | Gs | | | | |
|   |     |     | Ts | As | Gs | Gs | Ts | Cs | Ts | Ts | Gs | moeGs |
|   |     |     | moeTs | moeGs | moeGs | | | | | | |
| 9 | A09 | 200 | moeAs | moeCs | moeGs | moeTs | Cs | | | | |
|   |     |     | Ts | Ts | Gs | Gs | Ts | Gs | Gs | Gs | Ts | moeGs |
|   |     |     | moeAs | moeCs | moeGs | | | | | | |
| 10 | A10 | 200 | moeAs | moeGs | moeTs | moeCs | As | | | | |
|   |     |     | Cs | Gs | As | Cs | As | As | Gs | As | As | moeAs |
|   |     |     | moeCs | moeAs | moeCs | | | | | | |
| 11 | A11 | 200 | moeAs | moeCs | moeGs | moeAs | Cs | | | | |
|   |     |     | As | As | Gs | As | As | As | Cs | As | Cs | moeGs |
|   |     |     | moeGs | moeTs | moeCs | | | | | | |
| 12 | A12 | 200 | moeAs | moeGs | moeAs | moeAs | As | | | | |
|   |     |     | Cs | As | Cs | Gs | Gs | Ts | Cs | Gs | Gs | moeTs |
|   |     |     | moeCs | moeCs | moeTs | | | | | | |
| 13 | B01 | 200 | moeAs | moeAs | moeCs | moeAs | Cs | | | | |
|   |     |     | Gs | Gs | Ts | Cs | Gs | Gs | Ts | Cs | Cs | moeTs |
|   |     |     | moeGs | moeTs | moeCs | | | | | | |
| 14 | B02 | 200 | moeAs | moeCs | moeTs | moeCs | As | | | | |
|   |     |     | Cs | Ts | Gs | As | Cs | Gs | Ts | Gs | Ts | moeCs |
|   |     |     | moeTs | moeCs | moeAs | | | | | | |
| 15 | B03 | 200 | moeAs | moeCs | moeGs | moeGs | As | | | | |
|   |     |     | As | Gs | Gs | As | As | Cs | Gs | Cs | Cs | moeAs |
|   |     |     | moeCs | moeTs | moeTs | | | | | | |
| 16 | B04 | 200 | moeAs | moeTs | moeCs | moeTs | Gs | | | | |
|   |     |     | Ts | Gs | Gs | As | Cs | Cs | Ts | Ts | Gs | moeTs |
|   |     |     | moeCs | moeTs | moeCs | | | | | | |
| 17 | B05 | 200 | moeAs | moeCs | moeAs | moeCs | Ts | | | | |
|   |     |     | Ts | Cs | Ts | Ts | Cs | Cs | Gs | As | Cs | moeCs |
|   |     |     | moeGs | moeTs | moeGs | | | | | | |
| 18 | B06 | 200 | moeAs | moeCs | moeTs | moeCs | Ts | | | | |
|   |     |     | Cs | Gs | As | Cs | As | Cs | As | Gs | Gs | moeAs |
|   |     |     | moeCs | moeGs | moeTs | | | | | | |
| 19 | B07 | 200 | moeAs | moeAs | moeAs | moeCs | Cs | | | | |
|   |     |     | Cs | Cs | As | Gs | Ts | Ts | Cs | Gs | Ts | moeCs |
|   |     |     | moeTs | moeAs | moeAs | | | | | | |
| 20 | B08 | 200 | moeAs | moeTs | moeGs | moeTs | Cs | | | | |
|   |     |     | Cs | Cs | Cs | As | As | As | Gs | As | Cs | moeTs |
|   |     |     | moeAs | moeTs | moeGs | | | | | | |
| 21 | B09 | 200 | moeAs | moeCs | moeGs | moeCs | Ts | | | | |
|   |     |     | Cs | Gs | Gs | Gs | As | Cs | Gs | Os | Gs | moeTs |
|   |     |     | moeCs | moeAs | moeGs | | | | | | |
| 22 | B10 | 200 | moeAs | moeGs | moeCs | moeCs | Gs | | | | |
|   |     |     | As | As | Gs | As | As | Gs | As | Gs | Gs | moeTs |
|   |     |     | moeTs | moeAs | moeCs | | | | | | |
| 23 | B11 | 200 | moeAs | moeCs | moeAs | moeCs | As | | | | |
|   |     |     | Gs | Ts | As | Gs | As | Cs | Gs | As | As | moeAs |
|   |     |     | moeGs | moeCs | moeTs | | | | | | |
| 24 | B12 | 200 | moeAs | moeCs | moeAs | moeCs | Ts | | | | |
|   |     |     | Cs | Ts | Gs | Gs | Ts | Ts | Ts | Cs | Ts | moeGs |
|   |     |     | moeGs | moeAs | moeCs | | | | | | |
| 25 | C01 | 200 | moeAs | moeCs | moeGs | moeAs | Cs | | | | |
|   |     |     | Cs | As | Gs | As | As | As | Ts | As | Gs | moeTs |
|   |     |     | moeTs | moeTs | moeTs | | | | | | |
| 26 | C02 | 200 | moeAs | moeGs | moeTs | moeTs | As | | | | |
|   |     |     | As | As | As | Gs | Gs | Gs | Cs | Ts | Gs | moeCs |
|   |     |     | moeTs | moeAs | moeGs | | | | | | |
| 27 | C03 | 200 | moeAs | moeCs | moeGs | moeTs | Ts | | | | |
|   |     |     | Gs | Ts | Gs | As | Cs | Gs | As | Cs | Gs | moeAs |
|   |     |     | moeGs | moeGs | moeTs | | | | | | |
| 28 | C04 | 200 | moeAs | moeAs | moeTs | moeGs | Ts | | | | |
|   |     |     | As | Cs | Cs | Ts | As | Cs | Gs | Gs | Ts | moeTs |
|   |     |     | moeGs | moeGs | moeCs | | | | | | |
| 29 | C05 | 200 | moeAs | moeGs | moeTs | moeCs | As | | | | |
|   |     |     | Cs | Gs | Ts | Cs | Cs | Ts | Cs | Ts | Cs | moeTs |
|   |     |     | moeGs | moeTs | moeCs | | | | | | |
| 30 | C06 | 200 | moeCs | moeTs | moeGs | moeGs | Cs | | | | |
|   |     |     | Gs | As | Cs | As | Gs | Gs | Ts | As | Gs | moeGs |
|   |     |     | moeTs | moeCs | moeTs | | | | | | |
| 31 | C07 | 200 | moeCs | moeTs | moeCs | moeTs | Gs | | | | |
|   |     |     | Ts | Gs | Ts | Gs | As | Cs | Gs | Gs | Ts | moeGs |
|   |     |     | moeGs | moeTs | moeCs | | | | | | |

TABLE 4-continued

Identity of columns: Syn #, Well, Scale, Nucleotide at particular position (identified using base identifier followed by backbone identifier where 's' is phosphorothioate and 'moe' indicated a 2'-O-(methoxyethy) substituted nucleoside). The columns wrap around to next line when longer than one line.

| # | Well | Scale | | | | | | | | | |
|---|---|---|---|---|---|---|---|---|---|---|---|
| 32 | C08 | 200 | moeCs | | moeAs | | moeGs | | moeGs | | Ts |
|    |     |     | Cs    | Gs | Ts | Cs | Ts | Ts | Cs | Cs | Cs | moeGs |
|    |     |     | moeTs |    | moeGs |  | moeGs | | | | |
| 33 | C09 | 200 | moeCs |    | moeTs |  | moeGs |   | moeTs |   | Gs |
|    |     |     | Gs    | Ts | As | Gs | As | Cs | Gs | Ts | Gs | moeGs |
|    |     |     | moeAs |    | moeCs |  | moeAs | | | | |
| 34 | C10 | 200 | moeCs |    | moeTs |  | moeAs |   | moeAs |   | Cs |
|    |     |     | Gs    | As | Ts | Gs | Ts | Cs | Cs | Cs | Cs | moeAs |
|    |     |     | moeAs |    | moeAs |  | moeGs | | | | |
| 35 | C11 | 200 | moeCs |    | moeTs |  | moeGs |   | moeTs |   | Ts |
|    |     |     | Cs    | Gs | As | Cs | As | Cs | Ts | Cs | Ts | moeGs |
|    |     |     | moeGs |    | moeTs |  | moeTs | | | | |
| 36 | C12 | 200 | moeCs |    | moeTs |  | moeGs |   | moeGs |   | As |
|    |     |     | Cs    | Cs | As | As | Cs | As | Cs | Gs | Ts | moeTs |
|    |     |     | moeGs |    | moeTs |  | moeCs | | | | |
| 37 | D01 | 200 | moeCs |    | moeCs |  | moeGs |   | moeTs |   | Cs |
|    |     |     | Cs    | Gs | Ts | Gs | Ts | Ts | Ts | Gs | Ts | moeTs |
|    |     |     | moeCs |    | moeTs |  | moeGs | | | | |
| 38 | D02 | 200 | moeCs |    | moeTs |  | moeGs |   | moeAs |   | Cs |
|    |     |     | Ts    | As | Cs | As | As | Cs | As | Gs | As | moeCs |
|    |     |     | moeAs |    | moeCs |  | moeCs | | | | |
| 39 | D03 | 200 | moeCs |    | moeAs |  | moeAs |   | moeCs |   | As |
|    |     |     | Gs    | As | Cs | As | Cs | Cs | As | Gs | Gs | moeGs |
|    |     |     | moeGs |    | moeTs |  | moeCs | | | | |
| 40 | D04 | 200 | moeCs |    | moeAs |  | moeGs |   | moeGs |   | Gs |
|    |     |     | Gs    | Ts | Cs | Cs | Ts | As | Gs | Cs | Cs | moeGs |
|    |     |     | moeAs |    | moeCs |  | moeTs | | | | |
| 41 | D05 | 200 | moeCs |    | moeTs |  | moeCs |   | moeTs |   | As |
|    |     |     | Gs    | Ts | Ts | As | As | As | As | Gs | Gs | moeGs |
|    |     |     | moeCs |    | moeTs |  | moeGs | | | | |
| 42 | D06 | 200 | moeCs |    | moeTs |  | moeGs |   | moeCs |   | Ts |
|    |     |     | As    | Gs | As | As | Gs | Gs | As | Cs | Cs | moeGs |
|    |     |     | moeAs |    | moeGs |  | moeGs | | | | |
| 43 | D07 | 200 | moeCs |    | moeTs |  | moeGs |   | moeAs |   | As |
|    |     |     | As    | Ts | Gs | Ts | As | Cs | Cs | Ts | As | moeCs |
|    |     |     | moeGs |    | moeGs |  | moeTs | | | | |
| 44 | D08 | 200 | moeCs |    | moeAs |  | moeCs |   | moeCs |   | Cs |
|    |     |     | Gs    | Ts | Ts | Ts | Gs | Ts | Cs | Cs | Gs | moeTs |
|    |     |     | moeCs |    | moeAs |  | moeAs | | | | |
| 45 | D09 | 200 | moeCs |    | moeTs |  | moeCs |   | moeGs |   | As |
|    |     |     | Ts    | As | Cs | Gs | Gs | Gs | Ts | Cs | As | moeGs |
|    |     |     | moeTs |    | moeCs |  | moeAs | | | | |
| 46 | D10 | 200 | moeGs |    | moeGs |  | moeTs |   | moeAs |   | Gs |
|    |     |     | Gs    | Ts | Cs | Ts | Ts | Gs | Gs | Ts | Gs | moeGs |
|    |     |     | moeGs |    | moeTs |  | moeGs | | | | |
| 47 | D11 | 200 | moeGs |    | moeAs |  | moeCs |   | moeTs |   | Ts |
|    |     |     | Ts    | Gs | Cs | Cs | Ts | Ts | As | Cs | Gs | moeGs |
|    |     |     | moeAs |    | moeAs |  | moeGs | | | | |
| 48 | D12 | 200 | moeGs |    | moeTs |  | moeGs |   | moeGs |   | As |
|    |     |     | Gs    | Ts | Cs | Ts | Ts | Ts | Gs | Ts | Cs | moeTs |
|    |     |     | moeGs |    | moeTs |  | moeGs | | | | |
| 49 | E01 | 200 | moeGs |    | moeGs |  | moeAs |   | moeGs |   | Ts |
|    |     |     | Cs    | Ts | Ts | Ts | Gs | Ts | Cs | Ts | Gs | moeTs |
|    |     |     | moeGs |    | moeGs |  | moeTs | | | | |
| 50 | E02 | 200 | moeGs |    | moeGs |  | moeAs |   | moeCs |   | As |
|    |     |     | Cs    | Ts | Cs | Ts | Cs | Gs | As | Cs | As | moeCs |
|    |     |     | moeAs |    | moeGs |  | moeGs | | | | |
| 51 | E03 | 200 | moeGs |    | moeAs |  | moeCs |   | moeAs |   | Cs |
|    |     |     | As    | Gs | Gs | As | Cs | Gs | Ts | Gs | Gs moeCs | |
|    |     |     | moeGs |    | moeAs |  | moeGs | | | | |
| 52 | E04 | 200 | moeGs |    | moeAs |  | moeGs |   | moeTs |   | As |
|    |     |     | Cs    | Gs | As | Gs | Cs | Gs | Gs | Gs | Cs | moeCs |
|    |     |     | moeGs |    | moeAs |  | moeAs | | | | |
| 53 | E05 | 200 | moeGs |    | moeAs |  | moeCs |   | moeTs |   | As |
|    |     |     | Ts    | Gs | Gs | Ts | As | Gs | As | Cs | Gs | moeCs |
|    |     |     | moeTs |    | moeCs |  | moeGs | | | | |
| 54 | E06 | 200 | moeGs |    | moeAs |  | moeAs |   | moeGs |   | As |
|    |     |     | Gs    | Gs | Ts | Ts | As | Cs | As | Cs | As | moeGs |
|    |     |     | moeTs |    | moeAs |  | moeGs | | | | |
| 55 | E07 | 200 | moeGs |    | moeAs |  | moeGs |   | moeGs |   | Ts |
|    |     |     | Ts    | As | Cs | As | Cs | As | Gs | Ts | As | moeGs |
|    |     |     | moeAs |    | moeCs |  | moeGs | | | | |
| 56 | E08 | 200 | moeGs |    | moeTs |  | moeTs |   | moeGs |   | Ts |
|    |     |     | Cs    | Cs | Gs | Ts | Cs | Cs | Gs | Ts | Gs | moeTs |
|    |     |     | moeTs |    | moeTs |  | moeGs | | | | |

TABLE 4-continued

Identity of columns: Syn #, Well, Scale, Nucleotide at particular position (identified using base identifier followed by backbone identifier where 's' is phosphorothioate and 'moe' indicated a 2'-O-(methoxyethy) substituted nucleoside). The columns wrap around to next line when longer than one line.

| # | Well | Scale | | | | | | | | | | |
|---|---|---|---|---|---|---|---|---|---|---|---|---|
| 57 | E09 | 200 | moeGs | | moeAs | | moeCs | | moeTs | | Cs | |
|  |  |  | Ts | Cs | Gs | Gs | Gs | As | Cs | Cs | As | moeCs |
|  |  |  | moeCs |  | moeAs |  | moeCs |  |  |  |  |  |
| 58 | E10 | 200 | moeGs | | moeTs | | moeAs | | moeGs | | Gs | |
|  |  |  | As | Gs | As | As | Cs | Cs | As | Cs | Gs | moeAs |
|  |  |  | moeCs |  | moeCs |  | moeAs |  |  |  |  |  |
| 59 | E11 | 200 | moeGs | | moeGs | | moeTs | | moeTs | | Cs | |
|  |  |  | Ts | Ts | Cs | Gs | Gs | Ts | Ts | Gs | Gs | moeTs |
|  |  |  | moeTs |  | moeAs |  | moeTs |  |  |  |  |  |
| 60 | E12 | 200 | moeGs | | moeTs | | moeGs | | moeGs | | Gs | |
|  |  |  | Gs | Ts | Ts Cs | Gs | Ts | Cs | Cs | Ts | moeTs |  |
|  |  |  | moeGs |  | moeGs |  | moeGs |  |  |  |  |  |
| 61 | F01 | 200 | moeGs | | moeTs | | moeCs | | moeAs | | Cs | |
|  |  |  | Gs | Ts | Cs | Cs | Ts | Cs | Ts | Gs | As | moeAs |
|  |  |  | moeAs |  | moeTs |  | moeGs |  |  |  |  |  |
| 62 | F02 | 200 | moeGs | | moeTs | | moeCs | | moeCs | | Ts | |
|  |  |  | Cs | Cs | Ts | As | Cs | Cs | Gs | Ts | Ts | moeTs |
|  |  |  | moeCs |  | moeTs |  | moeCs |  |  |  |  |  |
| 63 | F03 | 200 | moeGs | | moeTs | | moeCs | | moeCs | | Cs | |
|  |  |  | Cs | As | Cs | Gs | Ts | Cs | Cs | Gs | Ts | moeCs |
|  |  |  | moeTs |  | moeCs |  | moeCs |  |  |  |  |  |
| 64 | F04 | 200 | moeTs | | moeCs | | moeAs | | moeCs | | Cs | |
|  |  |  | As | Gs | Gs | As | Cs | Cs | Gs | Cs | Gs | moeGs |
|  |  |  | moeAs |  | moeCs |  | moeCs |  |  |  |  |  |
| 65 | F05 | 200 | moeTs | | moeAs | | moeCs | | moeCs | | As | |
|  |  |  | As | Cs | Cs | As | Gs | As | Cs | Cs | Gs | moeAs |
|  |  |  | moeGs |  | moeAs |  | moeCs |  |  |  |  |  |
| 66 | F06 | 200 | moeTs | | moeCs | | moeCs | | moeTs | | Gs | |
|  |  |  | Ts | Cs | Ts | Ts | Ts | Gs | As | Cs | Cs | moeAs |
|  |  |  | moeCs |  | moeTs |  | moeCs |  |  |  |  |  |
| 67 | F07 | 200 | moeTs | | moeGs | | moeTs | | moeCs | | Ts | |
|  |  |  | Ts | Ts | Gs | As | Cs | Cs | As | Cs | Ts | moeCs |
|  |  |  | moeAs |  | moeCs |  | moeTs |  |  |  |  |  |
| 68 | F08 | 200 | moeTs | | moeGs | | moeAs | | moeCs | | Cs | |
|  |  |  | As | Cs | Ts | Cs | As | Cs | Ts | Gs | As | moeCs |
|  |  |  | moeCs |  | moeTs |  | moeCs |  |  |  |  |  |
| 69 | F09 | 200 | moeTs | | moeGs | | moeAs | | moeCs | | Cs | |
|  |  |  | Ts | Gs | Ts | Cs | Ts | Cs | As | As | Gs | moeTs |
|  |  |  | moeGs |  | moeAs |  | moeCs |  |  |  |  |  |
| 70 | F10 | 200 | moeTs | | moeCs | | moeAs | | moeAs | | Cs | |
|  |  |  | Ts | Gs | As | Cs | Ts | Ts | Ts | Cs | Cs | moeCs |
|  |  |  | moeTs |  | moeTs |  | moeAs |  |  |  |  |  |
| 71 | F11 | 200 | moeTs | | moeCs | | moeTs | | moeTs | | Ts | |
|  |  |  | As | Ts | Gs | As | Cs | Gs | Cs | Ts | Cs | moeCs |
|  |  |  | moeGs |  | moeAs |  | moeTs |  |  |  |  |  |
| 72 | F12 | 200 | moeTs | | moeTs | | moeAs | | moeTs | | Cs | |
|  |  |  | As | Cs | Gs | Cs | Ts | Gs | Cs | Gs | Cs | moeTs |
|  |  |  | moeTs |  | moeGs |  | moeGs |  |  |  |  |  |
| 73 | G01 | 200 | moeTs | | moeCs | | moeAs | | moeCs | | Gs | |
|  |  |  | Cs | Ts | Cs | Gs | Gs | Ts | Ts | Gs | moeGs |  |
|  |  |  | moeAs |  | moeTs |  | moeCs |  |  |  |  |  |
| 74 | G02 | 200 | moeTs | | moeCs | | moeCs | | moeTs | | Cs | |
|  |  |  | Ts | Ts | Cs | Cs | Cs | Gs | Ts | Gs | Gs | moeAs |
|  |  |  | moeCs |  | moeCs |  | moeCs |  |  |  |  |  |
| 75 | G03 | 200 | moeTs | | moeGs | | moeGs | | moeTs | | As | |
|  |  |  | Gs | As | Cs | Gs | Ts | Gs | Cs | As | Cs | moeAs |
|  |  |  | moeCs |  | moeTs |  | moeTs |  |  |  |  |  |
| 76 | G04 | 200 | moeTs | | moeTs | | moeCs | | moeTs | | Ts | |
|  |  |  | Cs | Cs | Gs | As | Cs | Cs | Gs | Ts | Gs | moeAs |
|  |  |  | moeCs |  | moeAs |  | moeTs |  |  |  |  |  |
| 77 | G05 | 200 | moeTs | | moeGs | | moeGs | | moeTs | | As | |
|  |  |  | Gs | As | Cs | Gs | Cs | Ts | Cs | Gs | Gs | moeGs |
|  |  |  | moeAs |  | moeCs |  | moeGs |  |  |  |  |  |
| 78 | G06 | 200 | moeTs | | moeAs | | moeGs | | moeAs | | Cs | |
|  |  |  | Gs | Cs | Ts | Cs | Gs | Gs | Gs | As | Cs | moeGs |
|  |  |  | moeGs |  | moeGs |  | moeTs |  |  |  |  |  |
| 79 | G07 | 200 | moeTs | | moeTs | | moeTs | | moeTs | | As | |
|  |  |  | Cs | As | Gs | Ts | Gs | Gs | Gs | As | As | moeCs |
|  |  |  | moeCs |  | moeTs |  | moeGs |  |  |  |  |  |
| 80 | G08 | 200 | moeTs | | moeGs | | moeGs | | moeGs | | As | |
|  |  |  | As | Cs | Cs | Ts | Gs | Ts | Ts | Cs | Gs | moeAs |
|  |  |  | moeCs |  | moeAs |  | moeCs |  |  |  |  |  |
| 81 | 009 | 200 | moeTs | | moeCs | | moeGs | | moeGs | | Gs | |
|  |  |  | As | Cs | Cs | As | Cs | Cs | As | Cs | Ts | moeAs |
|  |  |  | moeGs |  | moeGs |  | moeGs |  |  |  |  |  |

TABLE 4-continued

Identity of columns: Syn #, Well, Scale, Nucleotide at particular position (identified using base identifier followed by backbone identifier where 's' is phosphorothioate and 'moe' indicated a 2'-O-(methoxyethy) substituted nucleoside). The columns wrap around to next line when longer than one line.

| 82 | G10 | 200 | moeTs | | moeAs | | moeGs | | moeGs | | As |
| | Cs | As | As | As | Cs | Gs | Gs | Ts | As | moeGs | |
| | moeGs | | moeAs | | moeGs | | | | | | |
| 83 | G11 | 200 | moeTs | | moeGs | | moeCs | | moeTs | | As |
| | Gs | As | As | Gs | Gs | As | Cs | Cs | Gs | moeAs | |
| | moeGs | | moeAs | | moeTs | | | | | | |
| 84 | G12 | 200 | moeTs | | moeCs | | moeTs | | moeGs | | Ts |
| | Cs | As | Cs | Ts | Cs | Cs | Gs | As | Cs | moeGs | |
| | moeTs | | moeGs | | moeGs | | | | | | |

Reagent File (.tab File)

Table 5 is a tab for reagents necessary for synthesizing an oligonucleotides having both 2'-O-(methoxy-ethy)nucleosides and 2'-deoxy nucleosides located therein.

TABLE 5

Identity of columns: GroupName, Bottle ID, ReagentName, FlowRate, Concentration. Wherein reagent name is identified using base identifier, 'moe' indicated a 2'-O-(methoxyethy) substituted nucleoside and 'cpg' indicates a control pore glass solid support medium. The columns wrap around to next line when longer than one line.

SUPPORT

BEGIN
| 0 | | moeG | moeGcpg | 100 | 1 |
| 0 | | moe5meC | moe5meCcpg | 100 | 1 |
| 0 | | moeA | moeAcpg | 100 | 1 |
| 0 | | moeT | moeTcpg | 100 | 1 |
END
DEBLOCK

BEGIN
| 70 | | TCA | TCA | 100 | 1 |
END
WASH

BEGIN
| 65 | | ACN | ACN | 190 | 1 |
END
OXIDIZERS

BEGIN
| 68 | | BEAU | BEAUCAGE | 320 | 1 |
END
CAPPING

BEGIN
| 66 | | CAP_B | CAP_B | 220 | 1 |
| 67 | | CAP_A | CAP_A | 230 | 1 |
END
DEOXY THIOATE

BEGIN
| 31, 32 | | Gs | deoxyG | 270 | 1 |
| 39, 40 | | 5meCs | 5methyldeoxyC | 270 | 1 |
| 37, 38 | | As | deoxyA | 270 | 1 |
| 29, 30 | | Ts | deoxyT | 270 | 1 |
END
MOE-THIOATE BEGIN
| 15, 16 | | moeGs | methoxyethoxyG | 240 | 1 |
| 23, 24 | | moe5meCs | methoxyethoxyC | 240 | 1 |
| 21, 22 | | moeAs | methoxyethoxyA | 240 | 1 |
| 13, 14 | | moeTs | methoxyethoxyT | 240 | 1 |
END

TABLE 5-continued

Identity of columns: GroupName, Bottle ID, ReagentName, FlowRate, Concentration. Wherein reagent name is identified using base identifier, 'moe' indicated a 2'-O-(methoxyethy) substituted nucleoside and 'cpg' indicates a control pore glass solid support medium. The columns wrap around to next line when longer than one line.

ACTIVATORS

BEGIN
| 5, 6, 7, 8 | | SET | s-ethyl-tet | 280 | 1 |
Activates
DEOXY_THIOATE
MOE_THIOATE
END

Example 4

Oligonucleotide Synthesis—96 Well Plate Format oligonucleotides were synthesized via solid phase P(III) phosphoramidite chemistry using a multi well automated synthesizer utilizing input files as described in EXAMPLE 3 above. The oligonucleotides were synthesized by assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE/ABI, Pharmacia). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 5

Alternative Oligonucleotide Synthesis

Unsubstituted and substituted phosphodiester oligo nucleotides are alternately synthesized on an automated DNA synthesizer (Applied Biosystems model 380B) using standard phosphoramidite chemistry with oxidation by iodine.

Phosphorothioates are synthesized as per the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 hr), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, hereby incorporated by reference.

Alkylphosphonothioate oligonucleotides are prepared as described in published PCT applications PCT/US94/00902 and PCT/US93/06976 (published as WO 94/17093 and WO 94/02499, respectively).

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Boranophosphate oligonucleotides are prepared as described in U.S. Pat. Nos. 5,130,302 and 5,177,198, both herein incorporated by reference.

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligo nucleosides, also identified as amide-4 linked oligonucleosides, as well as mixed backbone compounds having, for instance, alternating MMI and PO or PS linkages are prepared as described in U.S. Pat. Nos. 5,378,825; 5,386,023; 5,489,677; 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 6

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5. They may also be prepared in accordance with U.S. Pat. Nos. 5,539,082; 5,700,922, and 5,719,262, herein incorporated by reference.

Example 7

Chimeric Oligonucleotide Synthesis

Chimeric oligonucleotides, oligonucleosides or mixed oligonucleotides/oligonucleosides of the invention can be of several different types. These include a first type wherein the 'gap' segment of linked nucleosides is positioned between 5' and 3' 'wing' segments of linked nucleosides and a second 'open end' type wherein the 'gap' segment is located at either the 3' or the 5' terminus of the oligomeric compound. Oligonucleotides of the first type are also known in the art as 'gapmers' or gapped oligonucleotides. oligonucleotides of the second type are also known in the art as 'hemimers' or 'wingmers.'

A. [2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using 2'-deoxy-5'-dimethoxytrityl-3'-O-phosphoramidites for the DNA portion and 5'-dimethoxytrityl-2'-O-methyl-3'-O-phosphoramidites for 5' and 3' wings. The standard synthesis cycle is modified by increasing the wait step after the delivery of tetrazole and base to 600 s repeated four times for DNA and twice for 2'-O-methyl. The fully protected oligonucleotide was cleaved from the support and the phosphate group is deprotected in 3:1 Ammonia/Ethanol at room temperature overnight then lyophilized to dryness. Treatment in methanolic ammonia for 24 hrs at room temperature is done to deprotect all bases and the samples are again lyophilized to dryness.

B. [2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides are prepared as per the procedure above for the 2'-O-methyl chimeric oligonucleotide, with the substitution of 2'-O-(methoxyethyl) amidites for the 2'-O-methyl amidites.

C. [2'-O-(2-Methoxyethyl)Phosphodiester]-[2'-deoxy Phosphorothioate]-[2'-O-(2-Methoxyethyl) Phosphodiester] Chimeric Oligonucleotide

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites in the wing portions. Sulfurization utilizing 3,H-1,2 benzodithiole-3-one 1,1 dioxide (Beaucage Reagent) is used to generate the phosphorothioate internucleotide linkages within the wing portions of the chimeric structures. Oxidization with iodine is used to generate the phosphodiester internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 8

Output Oligonucleotides from Automated Oligonucleotide Synthesis

Using the .seq files, the .cmd files and .tab file of Example 3, oligonucleotides were prepared as per the protocol of the 96 well format of Example 4. The oligonucleotides were prepared utilizing phosphorothioate chemistry to give in one instance a first library of phosphorothioate oligodeoxynucleotides. The oligonucleotides were prepared in a second instance as a second library of hybrid oligonucleotides having phosphorothioate backbones with a first and third 'wing' region of 2'-O-(methoxyethyl)nucleotides on either side of a center gap region of 2'-deoxy nucleotides. The two libraries contained the same set of oligonucleotide sequences. Thus the two libraries are redundant with respect to sequence but are unique with respect to the combination of sequence and chemistry. Because the sequences of the second library of compounds is the same as the first (however the chemistry is different), for brevity sake, the second library is not shown.

For illustrative purposes Tables 6-a and 6-b show the sequences of an intial first library, i.e., a library of phosphorothioate oligonucleotides targeted to a CD40 target. The compounds of Table 6-a shows the members of this listed in compliance with the established rule for listing SEQ ID NO:, i.e., in numerical SEQ ID NO: order.

TABLE 6-a

Sequences of Oligonucleotides Targeted to CD40 by SEQ ID NO.:

| NUCLEOBASE SEQUENCE | SEQ ID NO. |
|---|---|
| CCAGGCGGCAGGACCACT | 1 |
| GACCAGGCGGCAGGACCA | 2 |
| AGGTGAGACCAGGCGGCA | 3 |
| CAGAGGCAGACGAACCAT | 4 |
| GCAGAGGCAGACGAACCA | 5 |
| GCAAGCAGCCCCAGAGGA | 6 |
| GGTCAGCAAGCAGCCCCA | 7 |
| GACAGCGGTCAGCAAGCA | 8 |
| GATGGACAGCGGTCAGCA | 9 |
| TCTGGATGGACAGCGGTC | 10 |
| GGTGGTTCTGGATGGACA | 11 |
| GTGGGTGGTTCTGGATGG | 12 |
| GCAGTGGGTGGTTCTGGA | 13 |
| CACAAAGAACAGCACTGA | 14 |
| CTGGCACAAAGAACAGCA | 15 |
| TCCTGGCTGGCACAAAGA | 16 |
| CTGTCCTGGCTGGCACAA | 17 |
| CTCACCAGTTTCTGTCCT | 18 |
| TCACTCACCAGTTTCTGT | 19 |
| GTGCAGTCACTCACCAGT | 20 |
| ACTCTGTGCAGTCACTCA | 21 |
| CAGTGAACTCTGTGCAGT | 22 |
| ATTCCGTTTCAGTGAACT | 23 |
| GAAGGCATTCCGTTTCAG | 24 |
| TTCACCGCAAGGAAGGCA | 25 |
| CTCTGTTCCAGGTGTCTA | 26 |
| CTGGTGGCAGTGTGTCTC | 27 |
| TGGGGTCGCAGTATTTGT | 28 |
| GGTTGGGGTCGCAGTATT | 29 |
| CTAGGTTGGGGTCGCAGT | 30 |
| GGTGCCCTTCTGCTGGAC | 31 |
| CTGAGGTGCCCTTCTGCT | 32 |
| GTGTCTGTTTCTGAGGTG | 33 |
| TGGTGTCTGTTTCTGAGG | 34 |
| ACAGGTGCAGATGGTGTC | 35 |
| TTCACAGGTGCAGATGGT | 36 |
| GTGCCAGCCTTCTTCACA | 37 |
| TACAGTGCCAGCCTTCTT | 38 |
| GGACACAGCTCTCACAGG | 39 |
| TGCAGGACACAGCTCTCA | 40 |
| GAGCGGTGCAGGACACAG | 41 |
| AAGCCGGGCGAGCATGAG | 42 |
| AATCTGCTTGACCCCAAA | 43 |
| GAAACCCCTGTAGCAATC | 44 |
| GTATCAGAAACCCCTGTA | 45 |
| GCTCGCAGATGGTATCAG | 46 |
| GCAGGGCTCGCAGATGGT | 47 |
| TGGGCAGGGCTCGCAGAT | 48 |
| GACTGGGCAGGGCTCGCA | 49 |

TABLE 6-a-continued

Sequences of Oligonucleotides Targeted to CD40 by SEQ ID NO.:

| NUCLEOBASE SEQUENCE | SEQ ID NO. |
|---|---|
| CATTGGAGAAGAAGCCGA | 50 |
| GATGACACATTGGAGAAG | 51 |
| GCAGATGACACATTGGAG | 52 |
| TCGAAAGCAGATGACACA | 53 |
| GTCCAAGGGTGACATTTT | 54 |
| CACAGCTTGTCCAAGGGT | 55 |
| TTGGTCTCACAGCTTGTC | 56 |
| CAGGTCTTTGGTCTCACA | 57 |
| CTGTTGCACAACCAGGTC | 58 |
| GTTTGTGCCTGCCTGTTG | 59 |
| GTCTTGTTTGTGCCTGCC | 60 |
| CCACAGACAACATCAGTC | 61 |
| CTGGGACCACAGACAAC | 62 |
| TCAGCCGATCCTGGGGAC | 63 |
| CACCACCAGGGCTCTCAG | 64 |
| GGGATCACCACCAGGGCT | 65 |
| GAGGATGGCAAACAGGAT | 66 |
| ACCAGCACCAAGAGGATG | 67 |
| TTTTGATAAAGACCAGCA | 68 |
| TATTGGTTGGCTTCTTGG | 69 |
| GGGTTCCTGCTTGGGGTG | 70 |
| GTCGGGAAAATTGATCTC | 71 |
| GATCGTCGGGAAAATTGA | 72 |
| GGAGCCAGGAAGATCGTC | 73 |
| TGGAGCCAGGAAGATCGT | 74 |
| TGGAGCAGCAGTGTTGGA | 75 |
| GTAAAGTCTCCTGCACTG | 76 |
| TGGCATCCATGTAAAGTC | 77 |
| CGGTTGGCATCCATGTAA | 78 |
| CTCTTTGCCATCCTCCTG | 79 |
| CTGTCTCTCCTGCACTGA | 80 |
| GGTGCAGCCTCACTGTCT | 81 |
| AACTGCCTGTTTGCCCAC | 82 |
| CTTCTGCCTGCACCCCTG | 83 |
| ACTGACTGGGCATAGCTC | 84 |

The sequences shown in Table 6-a above and Table 6-B below are in a 5' to 3' direction. This is reversed with respect to 3' to 5' direction shown in the seq files of Example 3. For synthesis purposes, the .seq files are generated reading from 3' to 5'. This allows for aligning all of the 3' most 'A' nucleosides together, all of the 3' most 'G' nucleosides together, all of the 3' most 'C' nucleosides together and all of the 3' most 'T' nucleosides together. Thus when the first nucleoside of each particular oligonucleotide (attached to the solid support) is added to the wells on the plates, machine movement is reduced since an automatic pipette can move in a linear manner down one row and up another on the 96 well plate.

The location of the well holding each particular oligonucleotides is indicated by row and column. There are eight rows designated A to G and twelve columns designated 1 to 12 in a typical 96 well format plate. Any particular well location is indicated by its 'Well No.' which is indicated by the combination of the row and the column, e.g. A08 is the well at row A, column 8.

In Table 6-b below, the oligonucleotide of Table 6-a are shown reordered according to the Well No. on their synthesis plate. The order shown in Table 6-b is the actually order as synthesized on an automated synthesizer taking advantage of the preferred placement of the first nucleoside according to the above alignment criteria.

TABLE 6-b

Sequences of Oligonucleotides Targeted to CD40 Order by Synthesis Well No.

| Well | Sequence | SEQ ID |
|------|----------|--------|
| A01 | GACCAGGCGGCAGGACCA | 2 |
| A02 | AGGTGAGACCAGGCGGCA | 3 |
| A03 | GCAGAGGCAGACGAACCA | 5 |
| A04 | GCAAGCAGCCCCAGAGGA | 6 |
| A05 | GGTCAGCAAGCAGCCCCA | 7 |
| A06 | GACAGCGGTCAGCAAGCA | 8 |
| A07 | GATGGACAGCGGTCAGCA | 9 |
| A08 | GGTGGTTCTGGATGGACA | 11 |
| A09 | GCAGTGGGTGGTTCTGGA | 13 |
| A10 | CACAAAGAACAGCACTGA | 14 |
| A11 | CTGGCACAAAGAACAGCA | 15 |
| A12 | TCCTGGCTGGCACAAAGA | 16 |
| B01 | CTGTCCTGGCTGGCACAA | 17 |
| B02 | ACTCTGTGCAGTCACTCA | 21 |
| B03 | TTCACCGCAAGGAAGGCA | 25 |
| B04 | CTCTGTTCCAGGTGTCTA | 26 |
| B05 | GTGCCAGCCTTCTTCACA | 37 |
| B06 | TGCAGGACACAGCTCTCA | 40 |
| B07 | AATCTGCTTGACCCCAAA | 43 |
| B08 | GTATCAGAAACCCCTGTA | 45 |
| B09 | GACTGGGCAGGGCTCGCA | 49 |
| B10 | CATTGGAGAAGAAGCCGA | 50 |
| B11 | TCGAAAGCAGATGACACA | 53 |
| B12 | CAGGTCTTTGGTCTCACA | 57 |
| C01 | TTTTGATAAAGACCAGCA | 68 |
| C02 | GATCGTCGGGAAAATTGA | 72 |
| C03 | TGGAGCAGCAGTGTTGGA | 75 |
| C04 | CGGTTGGCATCCATGTAA | 78 |
| C05 | CTGTCTCTCCTGCACTGA | 80 |
| C06 | TCTGGATGGACAGCGGTC | 10 |
| C07 | CTGGTGGCAGTGTGTCTC | 27 |
| C08 | GGTGCCCTTCTGCTGGAC | 31 |
| C09 | ACAGGTGCAGATGGTGTC | 35 |
| C10 | GAAACCCTGTAGCAATC | 44 |
| C11 | TTGGTCTCACAGCTTGTC | 56 |
| C12 | CTGTTGCACAACCAGGTC | 58 |
| D01 | GTCTTGTTTGTGCCTGCC | 60 |
| D02 | CCACAGACAACATCAGTC | 61 |
| D03 | CTGGGGACCACAGACAAC | 62 |
| D04 | TCAGCCGATCCTGGGGAC | 63 |
| D05 | GTCGGGAAAATTGATCTC | 71 |
| D06 | GGAGCCAGGAAGATCGTC | 73 |
| D07 | TGGCATCCATGTAAAGTC | 77 |
| D08 | AACTGCCTGTTTGCCCAC | 82 |
| D09 | ACTGACTGGGCATAGCTC | 84 |
| D10 | GTGGTGGTTCTGGATGG | 12 |
| D11 | GAAGGCATTCCGTTTCAG | 24 |
| D12 | GTGTCTGTTTCTGAGGTG | 33 |
| E01 | TGGTGTCTGTTTCTGAGG | 34 |
| E02 | GGACACAGCTCTCACAGG | 39 |
| E03 | GAGCGGTGCAGGACACAG | 41 |
| E04 | AAGCCGGGCGAGCATGAG | 42 |
| E05 | GCTCGCAGATGGTATCAG | 46 |
| E06 | GATGACACATTGGAGAAG | 51 |
| E07 | GCAGATGACACATTGGAG | 52 |
| E08 | GTTTGTGCCTGCCTGTTG | 59 |
| E09 | CACCACCAGGGCTCTCAG | 64 |
| E10 | ACCAGCACCAAGAGGATG | 67 |
| E11 | TATTGGTTGGCTTCTTGG | 69 |
| E12 | GGGTTCCTGCTTGGGGTG | 70 |
| F01 | GTAAAGTCTCCTGCACTG | 76 |
| F02 | CTCTTTGCCATCCTCCTG | 79 |
| F03 | CTTCTGCCTGCACCCCTG | 83 |
| F04 | CCAGGCGGCAGGACCACT | 1 |
| F05 | CAGAGGCAGACGAACCAT | 4 |
| F06 | CTCACCAGTTTCTGTCCT | 18 |
| F07 | TCACTCACCAGTTTCTGT | 19 |
| F08 | GTGCAGTCACTCACCAGT | 20 |
| F09 | CAGTGAACTCTGTGCAGT | 22 |
| F10 | ATTCCGTTTCAGTGAACT | 23 |
| F11 | TGGGGTCGCAGTATTTGT | 28 |
| F12 | GGTTGGGGTCGCAGTATT | 29 |
| G01 | CTAGGTTGGGGTCGCAGT | 30 |
| G02 | CTGAGGTGCCCTTCTGCT | 32 |
| G03 | TTCACAGGTGCAGATGGT | 36 |
| G04 | TACAGTGCCAGCCTTCTT | 38 |
| G05 | GCAGGGCTCGCAGATGGT | 47 |
| G06 | TGGGCAGGGCTCGCAGAT | 48 |
| G07 | GTCCAAGGGTGACATTTT | 54 |
| G08 | CACAGCTTGTCCAAGGGT | 55 |
| G09 | GGGATCACCACCAGGGCT | 65 |
| G10 | GAGGATGGCAAACAGGAT | 66 |
| G11 | TGGAGCCAGGAAGATCGT | 74 |
| G12 | GGTGCAGCCTCACTGTCT | 81 |

Example 9

Oligonucleotide Analysis

A. Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman MDQ) or, for individually prepared samples, on a commercial CE apparatus (e.g., Beckman 5000, ABI 270). Base and backbone composition was confirmed by mass analysis of the compounds utilizing electrospray-mass spectroscopy. All assay test plates were diluted from the master plate using single and multi-channel robotic pipettors.

B. Alternative Oligonucleotide Analysis

After cleavage from the controlled pore glass support (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides are analyzed by polyacrylamide gel electrophoresis on denaturing gels. oligonucleotide purity is checked by $^{31}P$ nuclear magnetic resonance spectroscopy, and/or by HPLC, as described by Chiang et al., *J. Biol. Chem.* 1991, 266, 18162.

Example 10

Automated Assay of CD40 Oligonucleotides

A. Poly(A)+mRNA isolation

Poly(A)+mRNA was isolated according to Miura et al. (*Clin. Chem.*, 1996, 42, 1758). Briefly, for cells grown on 96-well plates, growth medium was removed from the cells and each well was washed with 200 μl cold PBS. 60 μl lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μl of lysate was transferred to Oligo d(T) coated 96 well plates (AGCT Inc., Irvine, Calif.). Plates were incubated for 60 minutes at room temperature, washed 3 times with 200 ul of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 ul of elution buffer (5 mM Tris-HCl pH 7.6), preheated to 70° C. was added to each well, the plate was incubated on a 90° C. plate for 5 minutes, and the eluate then transferred to a fresh 96-well plate. Cells grown on 100 mm or other standard plates may be treated similarly, using appropriate volumes of all solutions.

B. RT-PCR Analysis of CD40 mRNA Levels

Quantitation of CD40 mRNA levels was determined by reverse transcriptase polymerase chain reaction (RT-PCR) using the ABI PRISM™ _7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time.

As opposed to standard PCR, in which amplification products are quantitated after the PCR is completed, products in RT-PCR are quantitated as they accumulate. This is accomplished by including in the PCR reaction an oligonucleotide probe that anneals specifically between the forward and reverse PCR primers, and contains two fluorescent dyes. A reporter dye (e.g., JOE or FAM, PE-Applied Biosystems, Foster City, Calif.) is attached to the 5' end of the probe and a quencher dye (e.g., TAMRA, PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated.

With each cycle, additional reporter dye molecules are cleaved from their respective probes, and the fluorescence intensity is monitored at regular (six-second) intervals by laser optics built into the ABI PRISM™ _7700 Sequence Detection System. In each assay, a series of parallel reactions containing serial dilutions of mRNA from untreated control samples generates a standard curve that is used to quantitate the percent inhibition after antisense oligonucleotide treatment of test samples.

RT-PCR reagents were obtained from PE-Applied Biosystems, Foster City, Calif. RT-PCR reactions were carried out by adding 25 ul PCR cocktail (1×Taqman™ buffer A, 5.5 mM $MgCl_2$, 300 uM each of dATP, dCTP and dGTP, 600 uM of dUTP, 100 nM each of forward primer, reverse primer, and probe, 20 U RNAse inhibitor, 1.25 units AmpliTaq Gold™, and 12.5 U MuLV reverse transcriptase) to 96 well plates containing 25 ul poly(A) mRNA solution. The RT reaction was carried out by incubation for 30 minutes at 48° C. following a 10 minute incubation at 95° C. to activate the AmpliTaq Gold™, 40 cycles of a two-step PCR protocol were carried out: 95° C. for 15 seconds (denaturation) followed by 60° C. for 1.5 minutes (annealing/extension).

For CD40, the PCR primers were:
forward primer: CAGAGTTCACTGAAACGGAATGC (SEQ ID NO:86)
reverse primier: GGTGGCAGTGTGTCTCTCTGTTC (SEQ ID NO:87), and the PCR probe was: FAM-TTC-CTTGCGGTGAAAGCGAATTCCT-TAMRA (SEQ ID NO:88) where FAM (PE-Applied Biosystems, Foster City, Calif.) is the fluorescent reporter dye and TAMRA (PE-Applied Biosystems, Foster City, Calif.) is the quencher dye.

For GAPDH the PCR primers were:
forward primer: GAAGGTGAAGGTCGGAGTC (SEQ ID NO:89)
reverse primer: GAAGATGGTGATGGGATTTC (SEQ ID NO:90), and the PCR probe was: 5' JOE-CAAGCTTC-CCGTTCTCAGCC-TAMRA 3' (SEQ ID No. 91) where JOE (PE-Applied Biosystems, Foster City, Calif.) is the fluorescent reporter dye and TAMRA (PE-Applied Biosystems, Foster City, Calif.) is the quencher dye.

Example 11

Inhibition of CD40 Expression by Phosphorothioate Oligodeoxynucleotides

In accordance with the present invention, a series of oligonucleotides complementary to mRNA were designed to target different regions of the human CD40 mRNA, using published sequences (GenBank accession number X60592, incorporated herein as SEQ ID NO: 85). The oligonucleotides are shown in Table 7. Target sites are indicated by the beginning nucleotide numbers, as given in the sequence source reference (X60592), to which the oligonucleotide binds. All compounds in Table 7 are oligodeoxynucleotides with phosphorothioate backbones (internucleoside linkages) throughout. Data are averages from three experiments.

TABLE 7

Inhibition of CD40 mRNA Levels by Phosphorothioate Oligodeoxynucleotides

| ISIS # | TARGET SITE | SEQUENCE | % INHIB. | SEQ ID NO. |
|---|---|---|---|---|
| 18623 | 18 | CCAGGCGGCAGGACCACT | 30.71 | 1 |
| 18624 | 20 | GACCAGGCGGCAGGACCA | 28.09 | 2 |
| 18625 | 26 | AGGTGAGACCAGGCGGCA | 21.89 | 3 |
| 18626 | 48 | CAGAGGCAGACGAACCAT | 0.00 | 4 |
| 18627 | 49 | GCAGAGGCAGACGAACCA | 0.00 | 5 |
| 18628 | 73 | GCAAGCAGCCCCAGAGGA | 0.00 | 6 |
| 18629 | 78 | GGTCAGCAAGCAGCCCCA | 29.96 | 7 |
| 18630 | 84 | GACAGCGGTCAGCAAGCA | 0.00 | 8 |
| 18631 | 88 | GATGGACAGCGGTCAGCA | 0.00 | 9 |
| 18632 | 92 | TCTGGATGGACAGCGGTC | 0.00 | 10 |
| 18633 | 98 | GGTGGTTCTGGATGGACA | 0.00 | 11 |
| 18634 | 101 | GTGGGTGGTTCTGGATGG | 0.00 | 12 |
| 18635 | 104 | GCAGTGGGTGGTTCTGGA | 0.00 | 13 |
| 18636 | 152 | CACAAAGAACAGCACTGA | 0.00 | 14 |
| 18637 | 156 | CTGGCACAAAGAACAGCA | 0.00 | 15 |
| 18638 | 162 | TCCTGGCTGGCACA[ ]AGA | 0.00 | 16 |
| 18639 | 165 | CTGTCCTGGCTGGCACAA | 4.99 | 17 |
| 18640 | 176 | CTCACCAGTTTCTGTCCT | 0.00 | 18 |
| 18641 | 179 | TCACTCACCAGTTTCTGT | 0.00 | 19 |
| 18642 | 185 | GTGCAGTCACTCACCAGT | 0.00 | 20 |
| 18643 | 190 | ACTCTGTGCAGTCACTCA | 0.00 | 21 |
| 18644 | 196 | CAGTGAACTCTGTGCAGT | 5.30 | 22 |
| 18645 | 205 | ATTCCGTTTCAGTGAACT | 0.00 | 23 |
| 18646 | 211 | CAAGGCATTCCGTTTCAG | 9.00 | 24 |
| 18647 | 222 | TTCACCGCAAGGA[ ]GGCA | 0.00 | 25 |
| 18648 | 250 | CTCTGTTCCAGGTGTCTA | 0.00 | 26 |
| 18649 | 267 | CTGGTGGCAGTGTGTCTC | 0.00 | 27 |
| 18650 | 286 | TGGGGTCGCAGTATTTGT | 0.00 | 28 |
| 18651 | 289 | GGTTGGGGTCGCAGTATT | 0.00 | 29 |
| 18652 | 292 | CTAGGTTGGGGTCGCAGT | 0.00 | 30 |
| 18653 | 318 | GGTGCCCTTCTGCTGGAC | 19.67 | 31 |
| 18654 | 322 | CTGAGGTGCCCTTCTGCT | 15.63 | 32 |
| 18655 | 332 | GTGTCTGTTTCTGAGGTG | 0.00 | 33 |
| 18656 | 334 | TGGTGTCTGTTTCTGAGG | 0.00 | 34 |
| 18657 | 345 | ACAGGTGCAGATGGTGTC | 0.00 | 35 |
| 18658 | 348 | TTCACAGGTGCAGATGGT | 0.00 | 36 |
| 18659 | 360 | GTGCCAGCCTTCTTCACA | 5.67 | 37 |
| 18660 | 364 | TACAGTGCCAGCCTTCTT | 7.80 | 38 |

TABLE 7-continued

Inhibition of CD40 mRNA Levels by
Phosphorothioate Oligodeoxynucleotides

| ISIS # | TARGET SITE | SEQUENCE | % INHIB. | SEQ ID NO. |
|---|---|---|---|---|
| 18661 | 391 | GGACACAGCTCTCACAGG | 0.00 | 39 |
| 18662 | 395 | TGCAGGACACAGCTCTCA | 0.00 | 40 |
| 18663 | 401 | GAGCGGTGCAGGACACAG | 0.00 | 41 |
| 18664 | 416 | AAGCCGGGCGAGCATGAG | 0.00 | 42 |
| 18665 | 432 | AATCTGCTTGACCCCAAA | 5.59 | 43 |
| 18666 | 446 | GAAACCCTGTAGCAATC | 0.10 | 44 |
| 18667 | 452 | GTATCAGAAACCCTGTA | 0.00 | 45 |
| 18668 | 463 | GCTCGCAGATGGTATCAG | 0.00 | 46 |
| 18669 | 468 | GCAGGGCTCGCAGATGGT | 34.05 | 47 |
| 18670 | 471 | TGGGCAGGGCTCGCAGAT | 0.00 | 48 |
| 18671 | 474 | GACTGGGCAGGGCTCGCA | 2.71 | 49 |
| 18672 | 490 | CATTGGAGAAGAAGCCGA | 0.00 | 50 |
| 18673 | 497 | GATGACACATTGGAGAAG | 0.00 | 51 |
| 18674 | 500 | GCAGATGACACATTGGAG | 0.00 | 52 |
| 18675 | 506 | TCGAAAGCAGATGACACA | 0.00 | 53 |
| 18676 | 524 | GTCCAAGGGTGACATTTT | 8.01 | 54 |
| 18677 | 532 | CACAGCTTGTCCAAGGGT | 0.00 | 55 |
| 18678 | 539 | TTGGTCTCACAGCTTGTC | 0.00 | 56 |
| 18679 | 546 | CAGGTCTTTGGTCTCACA | 6.98 | 57 |
| 18680 | 558 | CTGTTGCACAACCAGGTC | 18.76 | 58 |
| 18681 | 570 | GTTTGTGCCTGCCTGTTG | 2.43 | 59 |
| 18682 | 575 | GTCTTGTTTGTGCCTGCC | 0.00 | 60 |
| 18683 | 590 | CCACAGACAACATCAGTC | 0.00 | 61 |
| 18684 | 597 | CTGGGGACCACAGACAAC | 0.00 | 62 |
| 18685 | 607 | TCAGCCGATCCTGGGGAC | 0.00 | 63 |
| 18686 | 621 | CACCACCAGGGCTCTCAG | 23.31 | 64 |
| 18687 | 626 | GGGATCACCACCAGGGCT | 0.00 | 65 |
| 18688 | 657 | GAGGATGGCAAACAGGAT | 0.00 | 66 |
| 18689 | 668 | ACCAGCACCAAGAGGATG | 0.00 | 67 |
| 18690 | 679 | TTTTGATAAAGACCAGCA | 0.00 | 68 |
| 18691 | 703 | TATTGGTTGGCTTCTTGG | 0.00 | 69 |
| 18692 | 729 | GGGTTCCTGCTTGGGGTG | 0.00 | 70 |
| 18693 | 750 | GTCGGGAAAATTGATCTC | 0.00 | 71 |
| 18694 | 754 | GATCGTCGGGAAAATTGA | 0.00 | 72 |
| 18695 | 765 | GGAGCCAGGAAGATCGTC | 0.00 | 73 |
| 18696 | 766 | TGGAGCCAGGAAGATCGT | 0.00 | 74 |
| 18697 | 780 | TGGAGCAGCAGTGTTGGA | 0.00 | 75 |
| 18698 | 796 | GTAAAGTCTCCTGCACTG | 0.00 | 76 |
| 18699 | 806 | TGGCATCCATGTAAAGTC | 0.00 | 77 |
| 18700 | 810 | CGGTTGGCATCCATGTAA | 0.00 | 78 |
| 18701 | 834 | CTCTTTGCCATCCTCCTG | 4.38 | 79 |
| 18702 | 861 | CTGTCTCTCCTGCACTGA | 0.00 | 80 |
| 18703 | 873 | GGTGCAGCCTCACTGTCT | 0.00 | 81 |
| 18704 | 910 | AACTGCCTGTTTGCCCAC | 33.89 | 82 |
| 18705 | 954 | CTTCTGCCTGCACCCCTG | 0.00 | 83 |
| 18706 | 976 | ACTGACTGGGCATAGCTC | 0.00 | 84 |

As shown in Table 7, SEQ ID NOS: 1, 2, 7, 47 and 82 demonstrated at least 25% inhibition of CD40 expression and are therefore preferred compounds of the invention.

Example 12

Inhibition of CD40 Expression by Phosphorothioate 2'-MOE Gapmer Oligonucleotides In accordance with the present invention, a second series of oligonucleotides complementary to mRNA were designed to target different regions of the human CD40 mRNA, using published sequence X60592. The oligonucleotides are shown in Table 8. Target sites are indicated by the beginning or initial nucleotide numbers, as given in the sequence source reference (X60592), to which the oligonucleotide binds.

All compounds in Table 8 are chimeric oligonucleotides ('gapmers') 18 nucleotides in length, composed of a central 'gap' region consisting of ten 2'-deoxynucleotides, which is flanked on both sides (5' and 3' directions) by four-nucleotide 'wings.' The wings are composed of 2'-methoxyethyl (2'-MOE) nucleotides. The intersugar (backbone) linkages are phosphorothioate (P=S) throughout the oligonucleotide. Cytidine residues in the 2'-MOE wings are 5-methylcytidines. Data are averaged from three experiments.

TABLE 8

Inhibition of CD40 mRNA Levels by Chimeric Phosphorothioate Oligonucleotides

| ISIS # | TARGET SITE | SEQUENCE | % Inhibition | SEQ ID NO. |
|---|---|---|---|---|
| 19211 | 18 | CCAGGCGGCAGGACCACT | 75.71 | 1 |
| 19212 | 20 | GACCAGGCGGCAGGACCA | 77.23 | 2 |
| 19213 | 26 | AGGTGAGACCAGGCGGCA | 80.82 | 3 |
| 19214 | 48 | CAGAGGCAGACGAACCAT | 23.68 | 4 |
| 19215 | 49 | GCAGAGGCAGACGAACCA | 45.97 | 5 |
| 19216 | 73 | GCAAGCAGCCCCAGAGGA | 65.80 | 6 |
| 19217 | 78 | GGTCAGCAAGCAGCCCCA | 74.73 | 7 |
| 19218 | 84 | GACAGCGGTCAGCAAGCA | 67.21 | 8 |
| 19219 | 88 | GATGGACAGCGGTCAGCA | 65.14 | 9 |
| 19220 | 92 | TCTGGATGGACAGCGGTC | 78.71 | 10 |
| 19221 | 98 | GGTGGTTCTGGATGGACA | 81.33 | 11 |
| 19222 | 101 | GTGGGTGGTTCTGGATGG | 57.79 | 12 |
| 19223 | 104 | GCAGTGGGTGGTTCTGGA | 73.70 | 13 |
| 19224 | 152 | CACAAAGAACAGCACTGA | 40.25 | 14 |
| 19225 | 156 | CTGGCACAAAGAACAGCA | 60.11 | 15 |
| 19226 | 162 | TCCTGGCTGGCACAAAGA | 10.18 | 16 |
| 19227 | 165 | CTGTCCTGGCTGGCACAA | 24.37 | 17 |
| 19228 | 176 | CTCACCAGTTTCTGTCCT | 22.30 | 18 |
| 19229 | 179 | TCACTCACCAGTTTCTGT | 40.64 | 19 |
| 19230 | 185 | GTGCAGTCACTCACCAGT | 82.04 | 20 |
| 19231 | 190 | ACTCTGTGCAGTCACTCA | 37.59 | 21 |
| 19232 | 196 | CAGTGAACTCTGTGCAGT | 40.26 | 22 |
| 19233 | 205 | ATTCCGTTTCAGTGAACT | 56.03 | 23 |
| 19234 | 211 | GAAGGCATTCCGTTTCAG | 32.21 | 24 |
| 19235 | 222 | TTCACCGCAAGGAAGGCA | 61.03 | 25 |
| 19236 | 250 | CTCTGTTCCAGGTGTCTA | 62.19 | 26 |
| 19237 | 267 | CTGGTGGCAGTGTGTCTC | 70.32 | 27 |
| 19238 | 286 | TGGGGTCGCAGTATTTGT | 0.00 | 28 |
| 19239 | 289 | GGTTGGGGTCGCAGTATT | 19.40 | 29 |
| 19240 | 292 | CTAGGTTGGGGTCGCAGT | 36.32 | 30 |
| 19241 | 318 | GGTGCCCTTCTGCTGGAC | 78.91 | 31 |
| 19242 | 322 | CTGAGGTGCCCTTCTGCT | 69.84 | 32 |
| 19243 | 332 | GTGTCTGTTTCTGAGGTG | 63.32 | 33 |
| 19244 | 334 | TGGTGTCTGTTTCTGAGG | 42.83 | 34 |
| 19245 | 345 | ACAGGTGCAGATGGTGTC | 73.31 | 35 |
| 19246 | 348 | TTCACAGGTGCAGATGGT | 47.72 | 36 |
| 19247 | 360 | GTGCCAGCCTTCTTCACA | 61.32 | 37 |
| 19248 | 364 | TACAGTGCCAGCCTTCTT | 46.82 | 38 |
| 19249 | 391 | GGACACAGCTCTCACAGG | 0.00 | 39 |
| 19250 | 395 | TGCAGGACACAGCTCTCA | 52.05 | 40 |
| 19251 | 401 | GAGCGGTGCAGGACACAG | 50.15 | 41 |
| 19252 | 416 | AAGCCGGGCGAGCATGAG | 32.36 | 42 |
| 19253 | 432 | AATCTGCTTGACCCCAAA | 0.00 | 43 |
| 19254 | 446 | GAAACCCTGTAGCAATC | 0.00 | 44 |
| 19255 | 452 | GTATCAGAAACCCTGTA | 36.13 | 45 |
| 19256 | 463 | GCTCGCAGATGGTATCAG | 64.65 | 46 |
| 19257 | 468 | GCAGGGCTCGCAGATGGT | 74.95 | 47 |
| 19258 | 471 | TGGGCAGGGCTCGCAGAT | 0.00 | 48 |
| 19259 | 474 | GACTGGGCAGGGCTCGCA | 82.00 | 49 |
| 19260 | 490 | CATTGGAGAAGAAGCCGA | 41.31 | 50 |
| 19261 | 497 | GATGACACATTGGAGAAG | 13.81 | 51 |
| 19262 | 500 | GCAGATGACACATTGGAG | 78.48 | 52 |
| 19263 | 506 | TCGAAAGCAGATGACACA | 59.28 | 53 |
| 19264 | 524 | GTCCAAGGGTGACATTTT | 70.99 | 54 |
| 19265 | 532 | CACAGCTTGTCCAAGGGT | 0.00 | 55 |
| 19266 | 539 | TTGGTCTCACAGCTTGTC | 45.92 | 56 |
| 19267 | 546 | CAGGTCTTTGGTCTCACA | 63.95 | 57 |
| 19268 | 558 | CTGTTGCACAACCAGGTC | 82.32 | 58 |
| 19269 | 570 | GTTTGTGCCTGCCTGTTG | 70.10 | 59 |
| 19270 | 575 | GTCTTGTTTGTGCCTGCC | 68.95 | 60 |
| 19271 | 590 | CCACAGACAACATCAGTC | 11.22 | 61 |
| 19272 | 597 | CTGGGGACCACAGACAAC | 9.04 | 62 |
| 19273 | 607 | TCAGCCGATCCTGGGGAC | 0.00 | 63 |
| 19274 | 621 | CACCACCAGGGCTCTCAG | 23.08 | 64 |
| 19275 | 626 | GGGATCACCACCAGGGCT | 57.94 | 65 |
| 19276 | 657 | GAGGATGGCAAACAGGAT | 49.14 | 66 |

TABLE 8-continued

Inhibition of CD40 mRNA Levels by Chimeric
Phosphorothioate Oligonucleotides

| ISIS # | TARGET SITE | SEQUENCE | % Inhibition | SEQ ID NO. |
|---|---|---|---|---|
| 19277 | 668 | ACCAGCACCAAGAGGATG | 3.48 | 67 |
| 19278 | 679 | TTTTGATAAAGACCAGCA | 30.58 | 68 |
| 19279 | 703 | TATTGGTTGGCTTCTTGG | 49.26 | 69 |
| 19280 | 729 | GGGTTCCTGCTTGGGGTG | 13.95 | 70 |
| 19281 | 750 | GTCGGGAAAATTGATCTC | 54.78 | 71 |
| 19282 | 754 | GATCGTCGGGAAAATTGA | 0.00 | 72 |
| 19283 | 765 | GGAGCCAGGAAGATCGTC | 69.47 | 73 |
| 19284 | 766 | TGGAGCCAGGAAGATCGT | 54.48 | 74 |
| 19285 | 780 | TGGAGCAGCAGTGTTGGA | 15.17 | 75 |
| 19286 | 796 | GTAAAGTCTCCTGCACTG | 30.62 | 76 |
| 19287 | 806 | TGGCATCCATGTAAAGTC | 65.03 | 77 |
| 19288 | 810 | CGGTTGGCATCCATGTAA | 34.49 | 78 |
| 19289 | 834 | CTCTTTGCCATCCTCCTG | 41.84 | 79 |
| 19290 | 861 | CTGTCTCTCCTGCACTGA | 25.68 | 80 |
| 19291 | 873 | GGTGCAGCCTCACTGTCT | 76.27 | 81 |
| 19292 | 910 | AACTGCCTGTTTGCCCAC | 63.34 | 82 |
| 19293 | 954 | CTTCTGCCTGCACCCCTG | 0.00 | 83 |
| 19294 | 976 | ACTGACTGGGCATAGCTC | 11.55 | 84 |

As shown in Table 8, SEQ ID NOS: 1, 2, 3, 6, 7, 8, 9, 10, 11, 12, 13, 15, 20, 23, 25, 26, 27, 31, 32, 33, 35, 37, 40, 41, 46, 47, 49, 52, 53, 54, 57, 58, 59, 60, 65, 71, 73, 74, 77, 81 and 82 demonstrated at least 50% inhibition of CD40 expression and are therefore preferred compounds of the invention.

Example 13

Oligonucleotide-Sensitive Sites of the CD40 Target Nucleic Acid

As the data presented in the preceding two Examples shows, several sequences were present in preferred compounds of two distinct oligonucleotide chemistries. Specifically, compounds having SEQ ID NOS: 1, 2, 7, 47 and 82 are preferred in both instances. These compounds map to different regions of the CD40 transcript but nevertheless define accessible sites of the target nucleic acid.

For example, SEQ ID NOS: 1 and 2 overlap each other and both map to the 5'-untranslated region (5'-UTR) of CD40. Accordingly, this region of CD40 is particularly preferred for modulation via sequence-based technologies. Similarly, SEQ ID NOS: 7 and 47 map to the open reading frame of CD40, whereas SEQ ID NO: 82 maps to the 3'-untranslated region (3'-UTR). Thus, the ORF and 3'-UTR of CD40 may be targeted by sequence-based technologies as well.

The reverse complements of the active CD40 compounds are easily determined by those skilled in the art and may be assembled to yield nucleotide sequences corresponding to accessible sites on the target nucleic acid. For example, the assembled reverse complement of SEQ ID NOS: 1 and 2 is represented below as SEQ ID NO:92:

```
5'- AGTGGTCCTGCCGCCTGGTC -3'        SEQ ID NO:92
    ||||||||||||||||||||
    TCACCAGGACGGCGGACC    -5'       SEQ ID NO:1
      ACCAGGACGGCGGACCAG -5'        SEQ ID NO:2
```

Through multiple iterations of the process of the invention, more extensive 'footprints' are generated. A library of this information is compiled and may be used by those skilled in the art in a variety of sequence-based technologies to study the molecular and biological functions of CD40 and to investigate or confirm its role in various diseases and disorders.

Example 14

Site Selection Program

Figure 20:
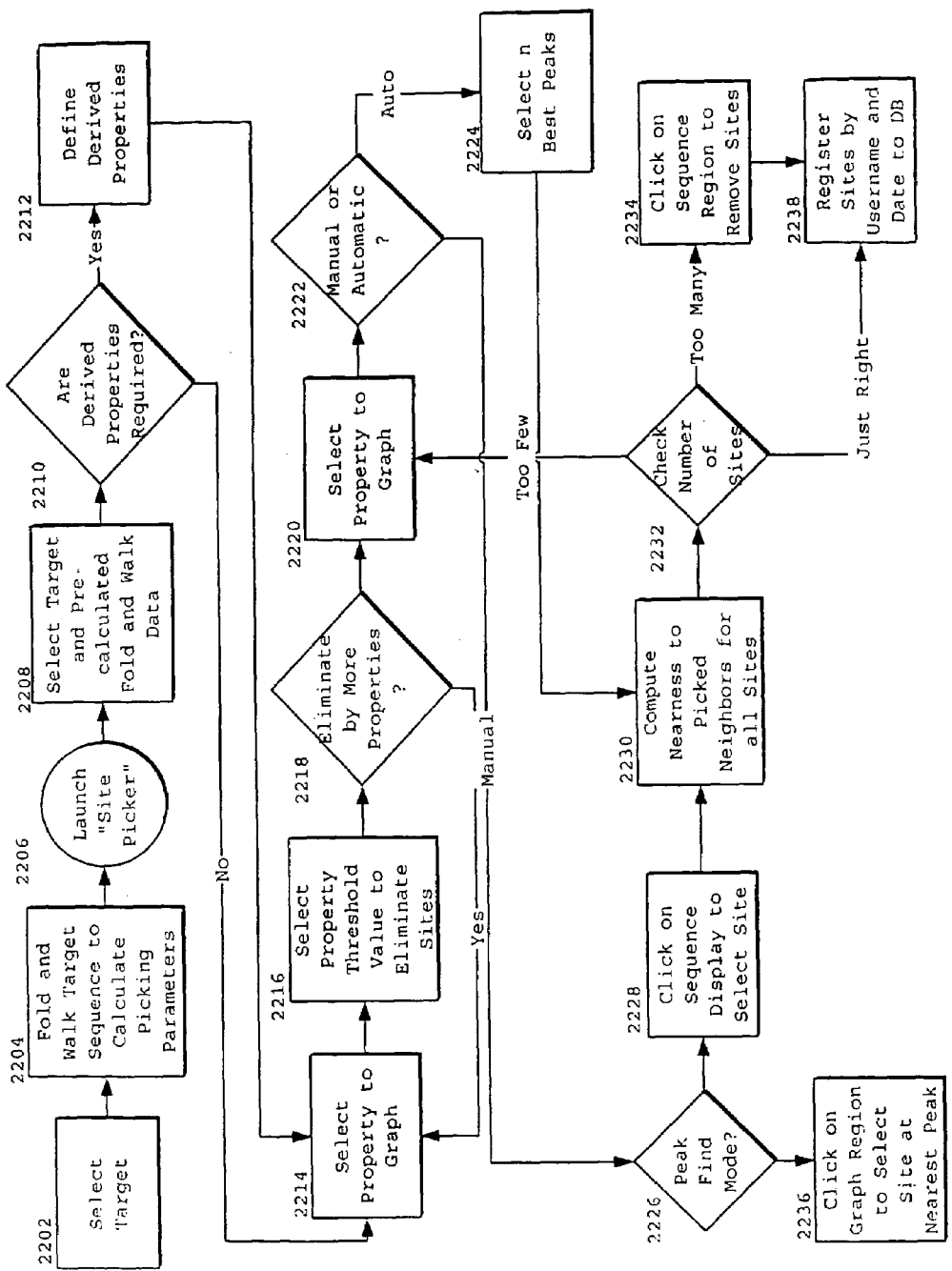
FIG. 20 is a flow diagram depicting the flow of date and materials in effecting a preferred embodiment of the invention as set forth in Example 14.

In a preferred embodiment of the invention, illustrated in FIG. 20, an application is deployed which facilitates the selection process for determining the target positions of the oligos to be synthesized, or 'sites.' This program is written using a three-tiered object-oriented approach. All aspects of the software described, therefore, are tightly integrated with the relational database. For this reason, explicit database read and write steps are not shown. It should be assumed that each step described includes database access. The description below illustrates one way the program can be used. The actual interface allows users to skip from process to process at will, in any order.

Before running the site picking program, the target must have all relevant properties computed as described previously and indicated in process step 2204. When the site picking program is launched at process step 2206 the user is presented with a panel showing targets which have previously been selected and had their properties calculated. The user selects one target to work with at process step 2208 and proceeds to decide if any derived properties will be needed at process step 2210. Derived properties are calculated by performing mathematical operations on combinations of pre-calculated properties as defined by the user at process step 2212.

The derived properties are made available as peers with all the pre-calculated properties. The user selects one of the properties to view plotted versus target position at process step 2214. This graph is shown above a linear representation of the target. The horizontal or position axis of both the graph and target are linked and scalable by the user. The zoom range goes from showing the full target length to showing individual target bases as letters and individual property points. The user next selects a threshold value below or above which all sites will be eliminated from future consideration at process step 2216. The user decides whether to eliminate more sites based on any other properties at process step 2218. If they choose to eliminate more, they return to pick another property to display at process step 2214 and threshold at process step 2216.

After eliminating sites, the user selects from the remaining list by choosing any property at process step 2220 and then choosing a manual or automatic selection technique at process step 2222. In the automatic technique, the user decides whether they want to pick from maxima or minima and the number of maxima or minima to be selected as sites at process step 2224. The software automatically finds and picks the points. When picking manually the user must decide if they wish to use automatic peak finding at process step 2226. If the user selects automatic peak finding, then user must click on the graphed property with the mouse at process step 2236. The nearest maxima or minima, depending on the modifier key held down, to the selected point will be picked as the site. Without the peak finding option, the user must pick a site at process step 2238 by clicking on its position on the linear representation of target.

Each time a site, or group of sites, is picked, a dynamic property is calculated for all possible sites (not yet eliminated) at process step 2230. This property indicates the nearness of the site two a picked site allowing the user to pick sites in subsequent iterations based on target coverage. After new sites are picked, the user determines if the desired number of sites has been picked. If too few sites have been picked the user returns to pick more 2220. If too many sites have been picked, the user may eliminate them by selecting and deleting them on the target display at process step 2234. If the correct number of sites is picked, and the user is satisfied with the set of picked sites, the user registers these sites to the database along with their name, notebook number, and page number at process step 2238. The database time stamps this registration event.

Example 15

Site Selection Program

Figure 21:
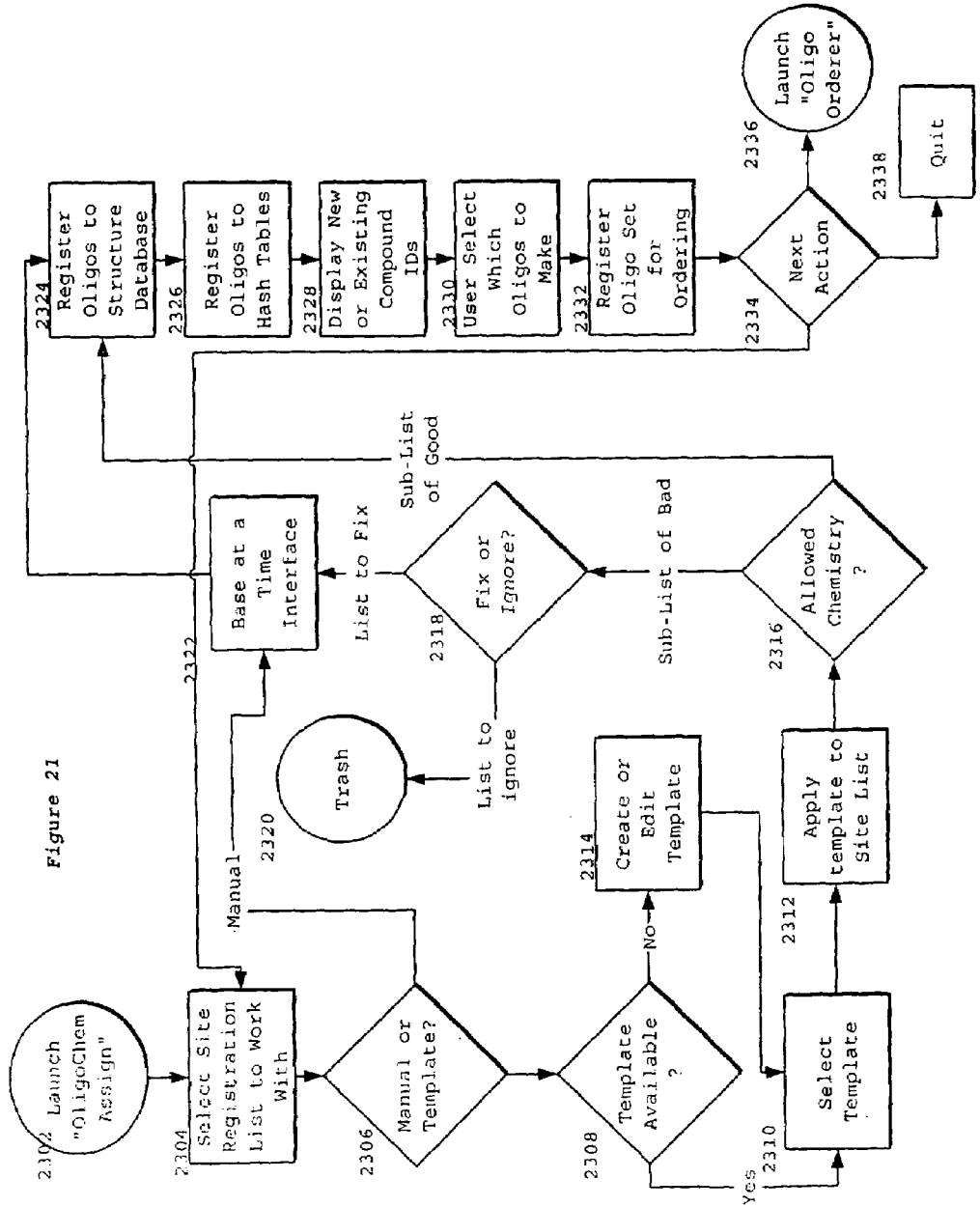
FIG. 21 is a flow diagram depicting the depicting the flow of date and materials in effecting a preferred embodiment of the invention as set forth in Example 15.

In a preferred embodiment of the invention, illustrated in FIG. 21, an application is deployed which facilitates the assignment of specific chemical structure to the complement of the sequence of the sites previously picked and facilitates the registration and ordering of these now fully defined antisense compounds. This program is written using a three-tiered object-oriented approach. All aspects of the software described, therefore, are tightly integrated with the relational database. For this reason, explicit database read and write steps are not shown, it being understood that each step described also includes appropriate database read/write access.

To begin using the oligonucleotide chemistry assignment program, the user launches it at process step 2302. The user then selects from the previously selected sets of oligonucleotides at process step 2304, registered to the database in site picker's process step 2238. Next, the user must decide whether to manually assign the chemistry a base at a time, or run the sites through a template at process step 2306. If the user chooses to use a template, they must determine if a desired template is available at process step 2308. If a template is not available with the desired chemistry modifications and the correct length, the user can define one at process step 2314.

To define a template, the user must select the length of the oligonucleotide the template is to define. This oligonucleotide is then represented as a bar with selectable regions. The user sets the number of regions on the oligonucleotide, and the positions and lengths of these regions by dragging them back and forth on the bar. Each region is represented by a different color.

For each region, the user defines the chemistry modifications for the sugars, the linkers, and the heterocycles at each base position in the region. At least four heterocycle chemistries must be given, one for each of the four possible base types (A, G, C or T or U) in the site sequence the template will be applied to. A user interface is provided to select these chemistries which show the molecular structure of each component selected and its modification name. By pushing on a pop-up list next to each of the pictures, the user may choose from a list of structures and names, those possible to put in this place. For example, the heterocycle that represents the base type G is shown as a two dimensional structure diagram. If the user clicks on the pop-up list, a row of other possible structures and names is shown. The user drags the mouse to the desired chemistry and releases the mouse. Now the newly selected molecule is displayed as the choice for G type heterocycle modifications.

Once the user has created a template, or selected an existing one, the software applies the template at process step 2312 to each of the complements of the sites in the list. When the templates are applied, it is possible that chemistries will be defined which are impossible to make with the chemical precursors presently used on the automatic synthesizer. To check this, a database is maintained of all precursors previously designed, and their availability for automated synthesis. When the templates are applied, the resulting molecules are tested at process step 2316 against this database to see if they are readily synthesized.

If a molecule is not readily synthesized, it is added to a list that the user inspects. At process step 2318, the user decides whether to modify the chemistry to make it compatible with the currently recognized list of available chemistries or to ignore it. To modify a chemistry, the user must use the base at a time interface at process step 2322. The user can also choose to go directly to this step, bypassing templates all together at process step 2306.

The base at a time interface at process step 2322 is very similar to the template editor at process step 2314 except that instead of specifying chemistries for regions, they are defined one base at a time. This interface also differs in that it dynamically checks to see if the design is readily synthesized as the user makes selections. In other words, each choice made limits the choices the software makes available on the pop-up selection lists. To accommodate this function, an additional choice is made available on each pop-up of 'not defined.' For example, this allows the user to inhibit linker choice from restricting the sugar choices by first setting the linker to 'not defined.' The user would then pick the sugar, and then pick from the remaining linker choices available.

Once all of the sites on the list are assigned chemistries or dropped, they are registered at process step 2324 to the commercial chemical structure database. Registering to this database makes sure the structure is unique, assigns it a new identifier if it is unique, and allows future structure and substructure searching by creating various hash-tables. The compound definition is also stored at process step 2326 to various hash tables referred to as chemistry/position tables. These allow antisense compound searching and categorization based on oligonucleotide chemistry modification sequences and equivalent base sequences.

The results of the registration are displayed at process step 2328 with the new IDs if they are new compounds and with the old IDs if they have been previously registered. The user next selects which of the compounds processed they wish to order for synthesis at process step 2330 and registers an order list at process step 2332 by including scientist name, notebook number and page number. The database timestamps this entry. The user may than choose at process step 2334 to quit the program at process step 2338, go back to the beginning and choose a new site list to work with process step 2304, or start the oligonucleotide ordering interface at process step 2336.

Example 16

Gene Walk to Optimize Oligonucleotide Sequence

A gene walk is executed using a CD40 antisense oligonucleotide having SEQ ID NO:15 (5'-CTGGCACAAA-GAACAGCA. In effecting this gene walk, the following parameters are used:

| Gene Walk Parameter | Entered value |
|---|---|
| Oligonucleotide Sequence ID: | 15 |
| Name of Gene Target: | CD40 |
| Scope of Gene Walk: | 20 |
| Sequence Shift Increment: | 1 |

Entering these values and effecting the gene walk centered on SEQ ID NO: 15 automatically generates the following new oligonucleotides:

TABLE 8

Oligonucleotide Generated By Gene Walk

| SEQ ID | Sequence |
|---|---|
| 93 | GAACAGCACTGACTGTTT |
| 94 | AGAACAGCACTGACTGTT |
| 95 | AAGAACAGCACTGACTGT |
| 96 | AAAGAACAGCACTGACTG |
| 97 | CAAAGAACAGCACTGACT |
| 98 | ACAAAGAACAGCACTGAC |
| 99 | CACAAAGAACAGCACTGA |
| 100 | GCACAAAGAACAGCACTG |
| 101 | GGCACAAAGAACAGCACT |
| 102 | TGGCACAAAGAACAGCAC |
| 15 | CTGGCACAAAGAACAGCA |

TABLE 8-continued

Oligonucleotide Generated By Gene Walk

| SEQ ID | Sequence |
|---|---|
| 103 | GCTGGCACAAAGAACAGC |
| 104 | GGCTGGCACAAAGAACAG |
| 105 | TGGCTGGCACAAAGAACA |
| 106 | CTGGCTGGCACAAAGAAC |
| 107 | CCTGGCTGGCACAAAGAA |
| 108 | TCCTGGCTGGCACAAAGA |
| 109 | GTCCTGGCTGGCACAAAG |
| 110 | TGTCCTGGCTGGCACAAA |
| 111 | CTGTCCTGGCTGGCACAA |
| 112 | TCTGTCCTGGCTGGCACA |

The list shown above contains 20 oligonucleotide sequences directed against the CD40 nucleic acid sequence. They are ordered by the position along the CD40 sequence at which the 5' terminus of each oligonucleotide hybridizes. Thus, the first ten oligonucleotides are single-base frame shift sequences directed against the CD40 sequence upstream of compound SEQ ID NO: 15 and the latter ten are single-base frame shift sequences directed against the CD40 sequence downstream of compound SEQ ID NO: 15.

What is claimed is:

1. A system of associated components for preparing a set of oligonucleotides that modulates expression of a selected nucleic acid comprising:
   a computer system that
   i) generates a list of oligonucleotide sequences according to a desired oligonucleotide length, thereby generating a series of oligonucleotide sequences;
   ii) applies a virtual oligonucleotide chemistry to the oligonucleotide sequences generated in step i) to yield a set of virtual oligonucleotides;
   iii) generates a subset of said set of virtual oligonucleotides, said subset being the result of a decision to target a functional region of said selected nucleic acid; and
   iv) generates synthesis instructions in computer manipulable form for said oligonucleotide sequences in said subset of said set of virtual oligonucleotides;
   an automated synthesizer that receives said synthesis instructions from said computer system and synthesizes only said oligonucleotide sequences in said subset of said set of virtual oligonucleotides, wherein the product of said synthesis is a set of synthesized oligonucleotides; and
   an apparatus that accepts said set of synthesized oligonucleotides and performs at least one procedure for each of said synthesized oligonucleotides wherein said procedure identifies particular members of said set that modulate expression of said selected nucleic acid.

2. The system of claim 1 wherein said functional region is the transcription start site, 5' cap, start codon, 5' untranslated region, 3' untranslated region, stop codon, 5' splice site or polyadenylation site.

3. A system of associated components for preparing a set of oligonucleotides that modulates expression of a selected nucleic acid comprising:
   a computer system that
   i) generates a list of oligonucleotide sequences according to a desired oligonucleotide length, thereby generating a series of oligonucleotide sequences;
   ii) applies a virtual oligonucleotide chemistry to the oligonucleotide sequences generated in step i) to yield a set of virtual oligonucleotides;
   iii) generates a subset of said set of virtual oligonucleotides, said subset being the result of a decision to: a) target a functional region of said selected nucleic acid, b) target an accessible site on said selected nucleic acid, and/or c) uniformly distribute oligonucleotide compounds across said selected nucleic acid; and
   iv) generates synthesis instructions in computer manipulable form for said oligonucleotide sequences in said subset of said set of virtual oligonucleotides;
   an automated synthesizer that receives said synthesis instructions from said computer system and synthesizes only said oligonucleotide sequences in said subset of said set of virtual oligonucleotides, wherein the product of said synthesis is a set of synthesized oligonucleotides;

a first apparatus that accepts said set of synthesized oligonucleotides and performs at least one procedure for each of said synthesized oligonucleotides wherein said procedure identifies particular members of said set that modulate expression of said selected nucleic acid; and a second apparatus for analyzing said set of synthesized oligonucleotides by a method or technique, selected from the group consisting of liquid chromatography, optical densiometry, mass spectroscopy, gel fluorescence and scintillation imaging, and capillary gel electrophoresis.

4. A system of associated components for preparing a set of oligonucleotides that modulates expression of a selected nucleic acid comprising:

a computer system that
   i) generates a list of oligonucleotide sequences according to a desired oligonucleotide length, thereby generating a series of oligonucleotide sequences;
   ii) applies a virtual oligonucleotide chemistry to the oligonucleotide sequences generated in step i) to yield a set of virtual oligonucleotides;
   iii) generates a subset of said set of virtual oligonucleotides, said subset being the result of a decision to:
      a) target a functional region of said selected nucleic acid, b) target an accessible site on said selected nucleic acid, and/or c) uniformly distribute oligonucleotide compounds across said selected nucleic acid; and
   iv) generates synthesis instructions in computer manipulable form for said oligonucleotide sequences in said subset of said set of virtual oligonucleotides;

an automated synthesizer that receives said synthesis instructions from said computer system and synthesizes only said oligonucleotide sequences in said subset of said set of virtual oligonucleotides, wherein the product of said synthesis is a set of synthesized oligonucleotides; and an apparatus that accepts said set of synthesized oligonucleotides and performs at least one procedure for each of said synthesized oligonucleotides wherein said procedure identifies particular members of said set that modulate expression of said selected nucleic acid.

* * * * *

SEQUENCE LISTING (1) GENERAL INFORMATION:

(iii) NUMBER OF SEQUENCES: 112

(2) INFORMATION FOR SEQ ID NO:1:

(i) SEQUENCE CHARACTERISTICS:
      (A) LENGTH:  18
      (B) TYPE: nucleic acid
      (C) STRANDEDNESS: single
      (D) TOPOLOGY: linear (xi) SEQUENCE DESCRIPTION: SEQ ID NO: 1:

CCAGGCGGCA GGACCACT                                    18

(2) INFORMATION FOR SEQ ID NO:2:

(i) SEQUENCE CHARACTERISTICS:
      (A) LENGTH:  18
      (B) TYPE: nucleic acid
      (C) STRANDEDNESS: single
      (D) TOPOLOGY: linear (xi) SEQUENCE DESCRIPTION: SEQ ID NO: 2:

GACCAGGCGG CAGGACCA                                    18

(2) INFORMATION FOR SEQ ID NO:3:

(i) SEQUENCE CHARACTERISTICS:
      (A) LENGTH:  18
      (B) TYPE: nucleic acid
      (C) STRANDEDNESS: single
      (D) TOPOLOGY: linear (xi) SEQUENCE DESCRIPTION: SEQ ID NO: 3:

AGGTGAGACC AGGCGGCA                                                          18

(2) INFORMATION FOR SEQ ID NO:4:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 4:

CAGAGGCAGA CGAACCAT                                                          18

(2) INFORMATION FOR SEQ ID NO:5:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 5:

GCAGAGGCAG ACGAACCA                                                          18

(2) INFORMATION FOR SEQ ID NO:6:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 6:

GCAAGCAGCC CCAGAGGA                                                          18

(2) INFORMATION FOR SEQ ID NO:7:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 7:

GGTCAGCAA GCAGCCCCA                                                          18

(2) INFORMATION FOR SEQ ID NO:8:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 8:

GACAGCGGTC AGCAAGCA                                                          18

(2) INFORMATION FOR SEQ ID NO:9:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 9:

GATGGACAGC GGTCAGCA                                               18

(2) INFORMATION FOR SEQ ID NO:10:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 10:

TCTGGATGGA CAGCGGTC                                               18

(2) INFORMATION FOR SEQ ID NO:11:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 11:

GGTGGTTCTG GATGGACA                                               18

(2) INFORMATION FOR SEQ ID NO:12:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 12:

GTGGGTGGTT CTGGATGG                                               18

(2) INFORMATION FOR SEQ ID NO:13:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 13:

GCAGTGGGTG GTTCTGGA                                               18

(2) INFORMATION FOR SEQ ID NO:14:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 14:

CACAAAGAAC AGCACTGA                                               18

(2) INFORMATION FOR SEQ ID NO:15:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 15:

CTGGCACAAA GAACAGCA                                              18

(2) INFORMATION FOR SEQ ID NO:16:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 16:

TCCTGGCTGG CACAAAGA                                              18

(2) INFORMATION FOR SEQ ID NO:17:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 17:

CTGTCCTGGC TGGCACAA                                              18

(2) INFORMATION FOR SEQ ID NO:18:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 18:

CTCACCAGTT TCTGTCCT                                              18

(2) INFORMATION FOR SEQ ID NO:19:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 19:

TCACTCACCA GTTTCTGT                                              18

(2) INFORMATION FOR SEQ ID NO:20:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 20:

GTGCAGTCAC TCACCAGT                                              18

(2) INFORMATION FOR SEQ ID NO:21:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 21:

ACTCTGTGCA GTCACTCA                                              18

-continued (2) INFORMATION FOR SEQ ID NO:22:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 22:

CAGTGAACTC TGTGCAGT                                                          18

(2) INFORMATION FOR SEQ ID NO:23:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 23:

ATTCCGTTTC AGTGAACT                                                          18

(2) INFORMATION FOR SEQ ID NO:24:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 24:

GAAGGCATTC CGTTTCAG                                                          18

(2) INFORMATION FOR SEQ ID NO:25:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 25:

TTCACCGCAA GGAAGGCA                                                          18

(2) INFORMATION FOR SEQ ID NO:26:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 26:

CTCTGTTCCA GGTGTCTA                                                          18

(2) INFORMATION FOR SEQ ID NO:27:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 27:

CTGGTGGCAG TGTGTCTC                                                          18

(2) INFORMATION FOR SEQ ID NO:28:

(i) SEQUENCE CHARACTERISTICS:
        (A) LENGTH:  18
        (B) TYPE: nucleic acid
        (C) STRANDEDNESS: single
        (D) TOPOLOGY: linear (xi) SEQUENCE DESCRIPTION: SEQ ID NO: 28:

TGGGGTCGCA GTATTTGT                                               18

(2) INFORMATION FOR SEQ ID NO:29:

(i) SEQUENCE CHARACTERISTICS:
        (A) LENGTH:  18
        (B) TYPE: nucleic acid
        (C) STRANDEDNESS: single
        (D) TOPOLOGY: linear (xi) SEQUENCE DESCRIPTION: SEQ ID NO: 29:

GGTTGGGGTC GCAGTATT                                               18

(2) INFORMATION FOR SEQ ID NO:30:

(i) SEQUENCE CHARACTERISTICS:
        (A) LENGTH:  18
        (B) TYPE: nucleic acid
        (C) STRANDEDNESS: single
        (D) TOPOLOGY: linear (xi) SEQUENCE DESCRIPTION: SEQ ID NO: 30:

CTAGGTTGGG GTCGCAGT                                               18

(2) INFORMATION FOR SEQ ID NO:31:

(i) SEQUENCE CHARACTERISTICS:
        (A) LENGTH:  18
        (B) TYPE: nucleic acid
        (C) STRANDEDNESS: single
        (D) TOPOLOGY: linear (xi) SEQUENCE DESCRIPTION: SEQ ID NO: 31:

GGTGCCCTTC TGCTGGAC                                               18

(2) INFORMATION FOR SEQ ID NO:32:

(i) SEQUENCE CHARACTERISTICS:
        (A) LENGTH:  18
        (B) TYPE: nucleic acid
        (C) STRANDEDNESS: single
        (D) TOPOLOGY: linear (xi) SEQUENCE DESCRIPTION: SEQ ID NO: 32:

CTGAGGTGCC CTTCTGCT                                               18

(2) INFORMATION FOR SEQ ID NO:33:

(i) SEQUENCE CHARACTERISTICS:
        (A) LENGTH:  18
        (B) TYPE: nucleic acid
        (C) STRANDEDNESS: single
        (D) TOPOLOGY: linear (xi) SEQUENCE DESCRIPTION: SEQ ID NO: 33:

GTGTCTGTTT CTGAGGTG                                               18

(2) INFORMATION FOR SEQ ID NO:34:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 34:

TGGTGTCTGT TTCTGAGG                                                    18

(2) INFORMATION FOR SEQ ID NO:35:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 35:

ACAGGTGCAG ATGGTGTC                                                    18

(2) INFORMATION FOR SEQ ID NO:36:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 36:

TTCACAGGTG CAGATGGT                                                    18

(2) INFORMATION FOR SEQ ID NO:37:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 37:

GTGCCAGCCT TCTTCACA                                                    18

(2) INFORMATION FOR SEQ ID NO:38:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 38:

TACAGTGCCA GCCTTCTT                                                    18

(2) INFORMATION FOR SEQ ID NO:39:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 39:

GGACACAGCT CTCACAGG                                                    18

(2) INFORMATION FOR SEQ ID NO:40:

(i) SEQUENCE CHARACTERISTICS:
            (A) LENGTH:  18
            (B) TYPE: nucleic acid
            (C) STRANDEDNESS: single
            (D) TOPOLOGY: linear (xi) SEQUENCE DESCRIPTION: SEQ ID NO: 40:

TGCAGGACAC AGCTCTCA                                                          18

(2) INFORMATION FOR SEQ ID NO:41:

(i) SEQUENCE CHARACTERISTICS:
            (A) LENGTH:  18
            (B) TYPE: nucleic acid
            (C) STRANDEDNESS: single
            (D) TOPOLOGY: linear (xi) SEQUENCE DESCRIPTION: SEQ ID NO: 41:

GAGCGGTGCA GGACACAG                                                          18

(2) INFORMATION FOR SEQ ID NO:42:

(i) SEQUENCE CHARACTERISTICS:
            (A) LENGTH:  18
            (B) TYPE: nucleic acid
            (C) STRANDEDNESS: single
            (D) TOPOLOGY: linear (xi) SEQUENCE DESCRIPTION: SEQ ID NO: 42:

AAGCCGGGCG AGCATGAG                                                          18

(2) INFORMATION FOR SEQ ID NO:43:

(i) SEQUENCE CHARACTERISTICS:
            (A) LENGTH:  18
            (B) TYPE: nucleic acid
            (C) STRANDEDNESS: single
            (D) TOPOLOGY: linear (xi) SEQUENCE DESCRIPTION: SEQ ID NO: 43:

AATCTGCTTG ACCCCAAA                                                          18

(2) INFORMATION FOR SEQ ID NO:44:

(i) SEQUENCE CHARACTERISTICS:
            (A) LENGTH:  18
            (B) TYPE: nucleic acid
            (C) STRANDEDNESS: single
            (D) TOPOLOGY: linear (xi) SEQUENCE DESCRIPTION: SEQ ID NO: 44:

GAAACCCCTG TAGCAATC                                                          18

(2) INFORMATION FOR SEQ ID NO:45:

(i) SEQUENCE CHARACTERISTICS:
            (A) LENGTH:  18
            (B) TYPE: nucleic acid
            (C) STRANDEDNESS: single
            (D) TOPOLOGY: linear (xi) SEQUENCE DESCRIPTION: SEQ ID NO: 45:

GTATCAGAAA CCCCTGTA                                                          18

(2) INFORMATION FOR SEQ ID NO:46:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 46:

GCTCGCAGAT GGTATCAG                                                  18

(2) INFORMATION FOR SEQ ID NO:47:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 47:

GCAGGGCTCG CAGATGGT                                                  18

(2) INFORMATION FOR SEQ ID NO:48:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 48:

TGGGCAGGGC TCGCAGAT                                                  18

(2) INFORMATION FOR SEQ ID NO:49:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 49:

GACTGGGCAG GGCTCGCA                                                  18

(2) INFORMATION FOR SEQ ID NO:50:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 50:

CATTGGAGAA GAAGCCGA                                                  18

(2) INFORMATION FOR SEQ ID NO:51:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 51:

GATGACACAT TGGAGAAG                                                  18

(2) INFORMATION FOR SEQ ID NO:52:

(i) SEQUENCE CHARACTERISTICS:

(A) LENGTH: 18
        (B) TYPE: nucleic acid
        (C) STRANDEDNESS: single
        (D) TOPOLOGY: linear (xi) SEQUENCE DESCRIPTION: SEQ ID NO: 52:

GCAGATGACA CATTGGAG                                                         18

(2) INFORMATION FOR SEQ ID NO:53:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 53:

TCGAAAGCAG ATGACACA                                                         18

(2) INFORMATION FOR SEQ ID NO:54:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 54:

GTCCAAGGGT GACATTTT                                                         18

(2) INFORMATION FOR SEQ ID NO:55:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 55:

CACAGCTTGT CCAAGGGT                                                         18

(2) INFORMATION FOR SEQ ID NO:56:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 56:

TTGGTCTCAC AGCTTGTC                                                         18

(2) INFORMATION FOR SEQ ID NO:57:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 57:

CAGGTCTTTG GTCTCACA                                                         18

(2) INFORMATION FOR SEQ ID NO:58:

(i) SEQUENCE CHARACTERISTICS:
        (A) LENGTH: 18

-continued

```
            (B) TYPE: nucleic acid
            (C) STRANDEDNESS: single
            (D) TOPOLOGY: linear (xi) SEQUENCE DESCRIPTION: SEQ ID NO: 58:

CTGTTGCACA ACCAGGTC                                                18

(2) INFORMATION FOR SEQ ID NO:59:

(i) SEQUENCE CHARACTERISTICS:
            (A) LENGTH:  18
            (B) TYPE: nucleic acid
            (C) STRANDEDNESS: single
            (D) TOPOLOGY: linear (xi) SEQUENCE DESCRIPTION: SEQ ID NO: 59:

GTTTGTGCCT GCCTGTTG                                                18

(2) INFORMATION FOR SEQ ID NO:60:

(i) SEQUENCE CHARACTERISTICS:
            (A) LENGTH:  18
            (B) TYPE: nucleic acid
            (C) STRANDEDNESS: single
            (D) TOPOLOGY: linear (xi) SEQUENCE DESCRIPTION: SEQ ID NO: 60:

GTCTTGTTTG TGCCTGCC                                                18

(2) INFORMATION FOR SEQ ID NO:61:

(i) SEQUENCE CHARACTERISTICS:
            (A) LENGTH:  18
            (B) TYPE: nucleic acid
            (C) STRANDEDNESS: single
            (D) TOPOLOGY: linear (xi) SEQUENCE DESCRIPTION: SEQ ID NO: 61:

CCACAGACAA CATCAGTC                                                18

(2) INFORMATION FOR SEQ ID NO:62:

(i) SEQUENCE CHARACTERISTICS:
            (A) LENGTH:  18
            (B) TYPE: nucleic acid
            (C) STRANDEDNESS: single
            (D) TOPOLOGY: linear (xi) SEQUENCE DESCRIPTION: SEQ ID NO: 62:

CTGGGGACCA CAGACAAC                                                18

(2) INFORMATION FOR SEQ ID NO:63:

(i) SEQUENCE CHARACTERISTICS:
            (A) LENGTH:  18
            (B) TYPE: nucleic acid
            (C) STRANDEDNESS: single
            (D) TOPOLOGY: linear (xi) SEQUENCE DESCRIPTION: SEQ ID NO: 63:

TCAGCCGATC CTGGGGAC                                                18

(2) INFORMATION FOR SEQ ID NO:64:

(i) SEQUENCE CHARACTERISTICS:
            (A) LENGTH:  18
            (B) TYPE: nucleic acid
```

(C) STRANDEDNESS: single
        (D) TOPOLOGY: linear (xi) SEQUENCE DESCRIPTION: SEQ ID NO: 64:

CACCACCAGG GCTCTCAG                                                 18

(2) INFORMATION FOR SEQ ID NO:65:

(i) SEQUENCE CHARACTERISTICS:
        (A) LENGTH:  18
        (B) TYPE: nucleic acid
        (C) STRANDEDNESS: single
        (D) TOPOLOGY: linear (xi) SEQUENCE DESCRIPTION: SEQ ID NO: 65:

GGGATCACCA CCAGGGCT                                                 18

(2) INFORMATION FOR SEQ ID NO:66:

(i) SEQUENCE CHARACTERISTICS:
        (A) LENGTH:  18
        (B) TYPE: nucleic acid
        (C) STRANDEDNESS: single
        (D) TOPOLOGY: linear (xi) SEQUENCE DESCRIPTION: SEQ ID NO: 66:

GAGGATGGCA AACAGGAT                                                 18

(2) INFORMATION FOR SEQ ID NO:67:

(i) SEQUENCE CHARACTERISTICS:
        (A) LENGTH:  18
        (B) TYPE: nucleic acid
        (C) STRANDEDNESS: single
        (D) TOPOLOGY: linear (xi) SEQUENCE DESCRIPTION: SEQ ID NO: 67:

ACCAGCACCA AGAGGATG                                                 18

(2) INFORMATION FOR SEQ ID NO:68:

(i) SEQUENCE CHARACTERISTICS:
        (A) LENGTH:  18
        (B) TYPE: nucleic acid
        (C) STRANDEDNESS: single
        (D) TOPOLOGY: linear (xi) SEQUENCE DESCRIPTION: SEQ ID NO: 68:

TTTTGATAAA GACCAGCA                                                 18

(2) INFORMATION FOR SEQ ID NO:69:

(i) SEQUENCE CHARACTERISTICS:
        (A) LENGTH:  18
        (B) TYPE: nucleic acid
        (C) STRANDEDNESS: single
        (D) TOPOLOGY: linear (xi) SEQUENCE DESCRIPTION: SEQ ID NO: 69:

TATTGGTTGG CTTCTTGG                                                 18

(2) INFORMATION FOR SEQ ID NO:70:

(i) SEQUENCE CHARACTERISTICS:
        (A) LENGTH:  18
        (B) TYPE: nucleic acid
        (C) STRANDEDNESS: single

```
        (D) TOPOLOGY: linear (xi) SEQUENCE DESCRIPTION: SEQ ID NO: 70:

GGGTTCCTGC TTGGGGTG                                                 18

(2) INFORMATION FOR SEQ ID NO:71:

(i) SEQUENCE CHARACTERISTICS:
        (A) LENGTH:  18
        (B) TYPE: nucleic acid
        (C) STRANDEDNESS: single
        (D) TOPOLOGY: linear (xi) SEQUENCE DESCRIPTION: SEQ ID NO: 71:

GTCGGGAAAA TTGATCTC                                                 18

(2) INFORMATION FOR SEQ ID NO:72:

(i) SEQUENCE CHARACTERISTICS:
        (A) LENGTH:  18
        (B) TYPE: nucleic acid
        (C) STRANDEDNESS: single
        (D) TOPOLOGY: linear (xi) SEQUENCE DESCRIPTION: SEQ ID NO: 72:

GATCGTCGGG AAAATTGA                                                 18

(2) INFORMATION FOR SEQ ID NO:73:

(i) SEQUENCE CHARACTERISTICS:
        (A) LENGTH:  18
        (B) TYPE: nucleic acid
        (C) STRANDEDNESS: single
        (D) TOPOLOGY: linear (xi) SEQUENCE DESCRIPTION: SEQ ID NO: 73:

GGAGCCAGGA AGATCGTC                                                 18

(2) INFORMATION FOR SEQ ID NO:74:

(i) SEQUENCE CHARACTERISTICS:
        (A) LENGTH:  18
        (B) TYPE: nucleic acid
        (C) STRANDEDNESS: single
        (D) TOPOLOGY: linear (xi) SEQUENCE DESCRIPTION: SEQ ID NO: 74:

TGGAGCCAGG AAGATCGT                                                 18

(2) INFORMATION FOR SEQ ID NO:75:

(i) SEQUENCE CHARACTERISTICS:
        (A) LENGTH:  18
        (B) TYPE: nucleic acid
        (C) STRANDEDNESS: single
        (D) TOPOLOGY: linear (xi) SEQUENCE DESCRIPTION: SEQ ID NO: 75:

TGGAGCAGCA GTGTTGGA                                                 18

(2) INFORMATION FOR SEQ ID NO:76:

(i) SEQUENCE CHARACTERISTICS:
        (A) LENGTH:  18
        (B) TYPE: nucleic acid
        (C) STRANDEDNESS: single
        (D) TOPOLOGY: linear
```

(xi) SEQUENCE DESCRIPTION: SEQ ID NO: 76:

GTAAAGTCTC CTGCACTG                                               18

(2) INFORMATION FOR SEQ ID NO:77:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 77:

TGGCATCCAT GTAAAGTC                                               18

(2) INFORMATION FOR SEQ ID NO:78:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 78:

CGGTTGGCAT CCATGTAA                                               18

(2) INFORMATION FOR SEQ ID NO:79:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 79:

CTCTTTGCCA TCCTCCTG                                               18

(2) INFORMATION FOR SEQ ID NO:80:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 80:

CTGTCTCTCC TGCACTGA                                               18

(2) INFORMATION FOR SEQ ID NO:81:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 81:

GGTGCAGCCT CACTGTCT                                               18

(2) INFORMATION FOR SEQ ID NO:82:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 82:

AACTGCCTGT TTGCCCAC                                                         18

(2) INFORMATION FOR SEQ ID NO:83:

(i) SEQUENCE CHARACTERISTICS:
                (A) LENGTH: 18
                (B) TYPE: nucleic acid
                (C) STRANDEDNESS: single
                (D) TOPOLOGY: linear (xi) SEQUENCE DESCRIPTION: SEQ ID NO: 83:

CTTCTGCCTG CACCCCTG                                                         18

(2) INFORMATION FOR SEQ ID NO:84:

(i) SEQUENCE CHARACTERISTICS:
                (A) LENGTH: 18
                (B) TYPE: nucleic acid
                (C) STRANDEDNESS: single
                (D) TOPOLOGY: linear (xi) SEQUENCE DESCRIPTION: SEQ ID NO: 84:

ACTGACTGGG CATAGCTC                                                         18

(2) INFORMATION FOR SEQ ID NO: 85:

(i) SEQUENCE CHARACTERISTICS:
                (A) LENGTH: 1004 base pairs
                (B) TYPE: nucleic acid
                (C) STRANDEDNESS: single
                (D) TOPOLOGY: linear (xi) SEQUENCE DESCRIPTION: SEQ ID NO: 85:

GCCTCGCTCG GGCGCCCAGT GGTCCTGCCG CCTGGTCTCA CCTCGCCATG       50

GTTCGTCTGC CTCTGCAGTG CGTCCTCTGG GGCTGCTTGC TGACCGCTGT       100

CCATCCAGAA CCACCCACTG CATGCAGAGA AAAACAGTAC CTAATAAACA       150

GTCAGTGCTG TTCTTTGTGC CAGCCAGGAC AGAAACTGGT GAGTGACTGC       200

ACAGAGTTCA CTGAAACGGA ATGCCTTCCT TGCGGTGAAA GCGAATTCCT       250

AGACACCTGG AACAGAGAGA CACACTGCCA CCAGCACAAA TACTGCGACC       300

CCAACCTAGG GCTTCGGGTC CAGCAGAAGG GCACCTCAGA AACAGACACC       350

ATCTGCACCT GTGAAGAAGG CTGGCACTGT ACGAGTGAGG CCTGTGAGAG       400

CTGTGTCCTG CACCGCTCAT GCTCGCCCGG CTTTGGGGTC AAGCAGATTG       450

CTACAGGGGT TTCTGATACC ATCTGCGAGC CCTGCCCAGT CGGCTTCTTC       500

TCCAATGTGT CATCTGCTTT CGAAAAATGT CACCCTTGGA CAAGCTGTGA       550

GACCAAAGAC CTGGTTGTGC AACAGGCAGG CACAAACAAG ACTGATGTTG       600

TCTGTGGTCC CCAGGATCGG CTGAGAGCCC TGGTGGTGAT CCCCATCATC       650

TTCGGGATCC TGTTTGCCAT CCTCTTGGTG CTGGTCTTTA TCAAAAAGGT       700

GGCCAAGAAG CCAACCAATA AGGCCCCCCA CCCCAAGCAG GAACCCCAGG       750

AGATCAATTT TCCCGACGAT CTTCCTGGCT CCAACACTGC TGCTCCAGTG       800

CAGGAGACTT TACATGGATG CCAACCGGTC ACCCAGGAGG ATGGCAAAGA       850

GAGTCGCATC TCAGTGCAGG AGAGACAGTG AGGCTGCACC CACCCAGGAG       900

TGTGGCCACG TGGGCAAACA GGCAGTTGGC CAGAGAGCCT GGTGCTGCTG       950

| | |
|---|---|
| CTGCAGGGGT GCAGGCAGAA GCGGGGAGCT ATGCCCAGTC AGTGCCAGCC | 1000 |
| CCTC | 1004 |

(2) INFORMATION FOR SEQ ID NO: 86:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 86:

| | |
|---|---|
| CAGAGTTCAC TGAAACGGAA TGC | 23 |

(2) INFORMATION FOR SEQ ID NO: 87:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 87:

| | |
|---|---|
| GGTGGCAGTG TGTCTCTCTG TTC | 23 |

(2) INFORMATION FOR SEQ ID NO: 88:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 88:

| | |
|---|---|
| TTCCTTGCGG TGAAAGCGAA TTCCT | 25 |

(2) INFORMATION FOR SEQ ID NO: 89:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 89:

| | |
|---|---|
| GAAGGTGAAG GTCGGAGTC | 19 |

(2) INFORMATION FOR SEQ ID NO: 90:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 90:

| | |
|---|---|
| GAAGATGGTG ATGGGATTTC | 20 |

(2) INFORMATION FOR SEQ ID NO: 91:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 91:

CAAGCTTCCC GTTCTCAGCC 20

(2) INFORMATION FOR SEQ ID NO: 92:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 92:

AGTGGTCCTG CCGCCTGGTC 20

(2) INFORMATION FOR SEQ ID NO:93:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 93:

GAACAGCACT GACTGTTT 18

(2) INFORMATION FOR SEQ ID NO:94:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 94:

AGAACAGCAC TGACTGTT 18

(2) INFORMATION FOR SEQ ID NO:95:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 95:

AAGAACAGCA CTGACTGT 18

(2) INFORMATION FOR SEQ ID NO:96:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 96:

AAAGAACAGC ACTGACTG 18

(2) INFORMATION FOR SEQ ID NO:97:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 97:

| | |
|---|---|
| CAAAGAACAG CACTGACT | 18 |

(2) INFORMATION FOR SEQ ID NO:98:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 98:

| | |
|---|---|
| ACAAAGAACA GCACTGAC | 18 |

(2) INFORMATION FOR SEQ ID NO:99:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 99:

| | |
|---|---|
| CACAAAGAAC AGCACTGA | 18 |

(2) INFORMATION FOR SEQ ID NO:100:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 100:

| | |
|---|---|
| GCACAAAGAA CAGCACTG | 18 |

(2) INFORMATION FOR SEQ ID NO:101:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 101:

| | |
|---|---|
| GGCACAAAGA ACAGCACT | 18 |

(2) INFORMATION FOR SEQ ID NO:102:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 102:

| | |
|---|---|
| TGGCACAAAG AACAGCAC | 18 |

(2) INFORMATION FOR SEQ ID NO:103:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 103:

| | |
|---|---|
| GCTGGCACAA AGAACAGC | 18 |

(2) INFORMATION FOR SEQ ID NO:104:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 104:

GGCTGGCACA AAGAACAG                                                    18

(2) INFORMATION FOR SEQ ID NO:105:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 105:

TGGCTGGCAC AAAGAACA                                                    18

(2) INFORMATION FOR SEQ ID NO:106:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 106:

CTGGCTGGCA CAAAGAAC                                                    18

(2) INFORMATION FOR SEQ ID NO:107:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 107:

CCTGGCTGGC ACAAAGAA                                                    18

(2) INFORMATION FOR SEQ ID NO:108:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 108:

TCCTGGCTGG CACAAAGA                                                    18

(2) INFORMATION FOR SEQ ID NO:109:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 109:

GTCCTGGCTG GCACAAAG                                                    18

```
(2) INFORMATION FOR SEQ ID NO:110:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 110:

TGTCCTGGCT GGCACAAA                                                           18

(2) INFORMATION FOR SEQ ID NO:111:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 111:

CTGTCCTGGC TGGCACAA                                                           18

(2) INFORMATION FOR SEQ ID NO:112:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 112:

TCTGTCCTGG CTGGCACA                                                           18
```